US007408060B2

(12) United States Patent
Schmees et al.

(10) Patent No.: US 7,408,060 B2
(45) Date of Patent: Aug. 5, 2008

(54) NONSTEROIDAL PROGESTERONE RECEPTOR MODULATORS

(75) Inventors: Norbert Schmees, Berlin (DE); Ulrich Bothe, Berlin (DE); Wolfgang Schwede, Glienicke (DE); Carsten Moeller, Berlin (DE); Ulrike Fuhrmann, Berlin (DE); Anja Schmidt, Berlin (DE)

(73) Assignee: Schering AG, Berlin (DE)

( * ) Notice: Subject to any disclaimer, the term of this patent is extended or adjusted under 35 U.S.C. 154(b) by 125 days.

(21) Appl. No.: 11/473,336

(22) Filed: Jun. 23, 2006

(65) Prior Publication Data

US 2007/0142464 A1 Jun. 21, 2007

Related U.S. Application Data

(60) Provisional application No. 60/693,404, filed on Jun. 24, 2005.

(51) Int. Cl.
*C07D 265/02* (2006.01)
*C07D 265/00* (2006.01)
*C07D 305/12* (2006.01)

(52) U.S. Cl. ............................ 544/92; 544/63; 549/307

(58) Field of Classification Search ................... 544/63, 544/92; 549/307

See application file for complete search history.

(56) References Cited

U.S. PATENT DOCUMENTS

| | | | | |
|---|---|---|---|---|
| 6,777,409 | B2 * | 8/2004 | Jaroch et al. | 514/230.5 |
| 7,112,584 | B2 * | 9/2006 | Schmees et al. | 514/230.5 |
| 7,129,270 | B2 * | 10/2006 | JaRoch et al. | 514/470 |
| 7,166,592 | B2 * | 1/2007 | Jaroch et al. | 514/230.5 |
| 2003/0203902 | A1 | 10/2003 | Lehmann | |
| 2005/0090559 | A1 | 4/2005 | Berger | |

FOREIGN PATENT DOCUMENTS

| | | | |
|---|---|---|---|
| DE | 19723722 | A1 | 5/1997 |
| DE | 10346939 | A1 | 5/2005 |
| WO | WO 98/54159 | | 12/1998 |
| WO | WO 03/059899 | A1 | 7/2003 |
| WO | WO 03/075915 | A1 | 9/2003 |

OTHER PUBLICATIONS

Jurisson et al. Chemical Reviews, 1999, vol. 99, No. 9, p. 2210.*

* cited by examiner

*Primary Examiner*—D. Margaret Seaman
*Assistant Examiner*—Nizal S Chandrakumar
(74) *Attorney, Agent, or Firm*—Millen, White, Zelano & Branigan, P.C.

(57) ABSTRACT

This invention relates to nonsteroidal progesterone receptor modulators of general formula I,

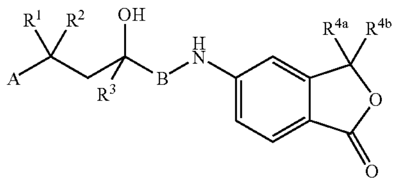

(I)

a process for their production, the use of progesterone receptor modulators for the production of pharmaceutical agents as well as pharmaceutical compositions that contain these compounds.

The compounds according to the invention are suitable for therapy and prophylaxis of gynecological diseases, such as endometriosis, leiomyomas of the uterus, dysfunctional bleeding and dysmenorrhea, as well as for the therapy and prophylaxis of hormone-dependent tumors and for use for female birth control as well as for hormone replacement therapy.

26 Claims, No Drawings

NONSTEROIDAL PROGESTERONE RECEPTOR MODULATORS

This application claims the benefit of the filing date of U.S. Provisional Application Ser. No. 60/693,404 filed Jun. 24, 2005.

This invention relates to nonsteroidal progesterone receptor modulators, a process for their production, the use of progesterone receptor modulators for the production of pharmaceutical agents as well as pharmaceutical compositions that contain these compounds.

The steroid hormone progesterone regulates the reproductive process in the female organism in a decisive way. During the cycle and in pregnancy, progesterone is secreted in large amounts from the ovary or the placenta. By interaction with estrogens, progesterone produces cyclic changes of the uterine mucous membrane (endometrium) in the menstrual cycle. Under the influence of elevated progesterone levels after ovulation, the uterine mucous membrane is converted into a state that allows the nidation of an embryo (blastocyte). In pregnancy, progesterone controls the relaxation of the myometrium and retains the function of the decidual tissue.

In addition, it is known that progesterone inhibits the endometrial proliferation by the suppression of the estrogen-mediated mitosis in the uterus tissue (K. Chwalisz, R. M. Brenner, U. Fuhrmann, H. Hess-Stumpp, W. Elger, Steroids 65, 2000, 741-751).

An important role of the progesterone and the progesterone receptors is also known in pathophysiological processes. Progesterone receptors are detected in foci of endometriosis, but also in tumors of the uterus, the breast and the CNS. In addition, it is known that uterus leiomyomas grow in a progesterone-dependent manner.

The actions of progesterone in the tissues of genital organs and in other tissues are carried out by interactions with progesterone receptors, which are responsible for the cellular effects.

Progesterone receptor modulators are either pure agonists or partially or completely inhibit the action of progesterone. Consequently, substances are defined as pure agonists, partial agonists (SPRMS) and pure antagonists.

According to the ability of the progesterone receptor modulators to influence the action of the progesterone receptor, these compounds have a considerable potential as therapeutic agents for gynecological and oncological indications as well as for obstetrics and birth control.

Pure progesterone receptor antagonists completely inhibit the action of progesterone in the progesterone receptor. They have antiovulatory properties as well as the ability to inhibit estrogen effects in the endometrium up to full atrophy. They are therefore especially suitable for intervening in the female reproductive process, e.g., in post-ovulation, to prevent nidation; in pregnancy, to increase the reactivity of the uterus to prostaglandins or oxytocin or to ensure the opening and softening ("maturation") of the cervix as well as to make the myometrium highly prepared for labor.

In foci of endometriosis or in tumor tissue, which are (is) equipped with progesterone receptors, an advantageous influence of the disease process is expected after application of pure progesterone receptor antagonists. Special advantages for influencing pathologic conditions, such as endometriosis or uterus leiomyomas, could then be given if in addition an inhibition of the ovulation can be achieved by the progesterone receptor antagonists. When ovulation is inhibited, a portion of the ovarian hormone production and thus the stimulative effect that is due to this portion are also due to the pathologically altered tissue.

A large number of analogs with varying degrees of progesterone receptor-antagonistic activity followed the first described progesterone receptor antagonist RU 486 (also mifepristone). While RU 486, in addition to the progesterone receptor-antagonistic action, also shows an antiglucocorticoidal action, compounds synthesized later are distinguished primarily by a more selective action than progesterone receptor antagonists.

From the literature, in addition to steroidal compounds such as onapristone or lilopristone, which are distinguished from progesterone-receptor-antagonistic action to antiglucorticoidal action relative to RU 486 by a better dissociation of action, various nonsteroidal structures, whose antagonistic action on the progesterone receptor is examined, are also known [see, e.g., S. A. Leonhardt and D. P. Edwards, Exp. Biol. Med. 227: 969-980 (2002) and R. Winneker, A. Fensome, J. E. Wrobel, Z. Zhang, P. Zhang, Seminars in Reproductive Medicine, Volume 23: 46-57 (2005)]. Previously known compounds, however, have only moderately antagonistic activity compared to the known steroidal structures. The most effective nonsteroidal compounds are described as having in vitro activities of 10% of the activity of RU 486.

The antiglucocorticoidal activity is disadvantageous for a therapeutic application in which the inhibition of the progesterone receptors is a primary focus of therapy. An antiglucocorticoidal activity causes undesirable side effects in the case of therapeutically necessary dosages. This can prevent the application of a therapeutically useful dose or lead to termination of the treatment.

The partial or complete reduction of the antiglucocorticoidal properties is therefore an important requirement for the therapy with progesterone receptor antagonists, in particular for those indications that require a treatment lasting weeks or months.

In contrast to the pure antagonists, progesterone receptor partial agonists (SPRMs) show a residual agonistic property, which can be strongly pronounced to different degrees. This leads to the fact that these substances show potential agonistic actions of the progesterone receptor in specific organ systems (D. DeManno, W. Elger, R. Garg, R. Lee, B. Schneider, H. Hess-Stumpp, G. Schuber, K. Chwalisz, Steroids 68, 2003, 1019-1032). Such an organ-specific and dissociated action can be of therapeutic use for the indications described.

It is therefore the object of this invention to make available additional nonsteroidal progesterone receptor modulators. These compounds are to have a reduced antiglucocorticoidal action and are therefore suitable for the therapy and prophylaxis of gynecological diseases such as endometriosis, leiomyomas of the uterus, dysfunctional bleeding and dysmenorrhea. In addition, the compounds according to the invention are to be suitable for the therapy and prophylaxis of hormone-dependent tumors, for example breast, endometrial, ovarian and prostate cancers. In addition, the compounds are to be suitable for use in female birth control and for female hormone replacement therapy.

The object is achieved according to this invention by the preparation of non-steroidal compounds of general formula I (I)

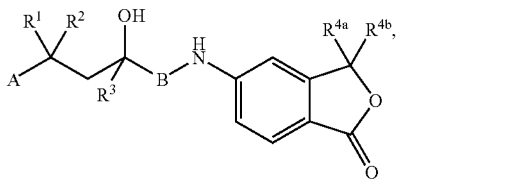

in which $R^1$ and $R^2$, independently of one another, mean a hydrogen atom, a straight or nonstraight, branched or unbranched $C_1$-$C_5$-alkyl group, also together with the C atom of the chain forming a ring with a total of 3-7 members, $R^3$ means a radical C≡C—$R^a$, whereby $R^a$ means a hydrogen or a $C_1$-$C_8$-alkyl, $C_2$-$C_8$-alkenyl, $C_2$-$C_8$-alkinyl, $C_3$-$C_{10}$-cycloalkyl, or heterocycloalkyl that optionally is substituted in one or more places, in the same way or differently, with K, or an aryl or heteroaryl that optionally is substituted in one or more places, in the same way or differently, with L, K is a cyano, halogen, hydroxy, nitro, —C(O)$R^b$, $CO_2R^b$, —O—$R^b$, —S—$R^b$, $SO_2NR^cR^d$, —C(O)—$NR^cR^d$, —OC(O)—$NR^cR^d$, or —C═$NOR^b$—$NR^cR^d$ or a $C_3$-$C_{10}$-cycloalkyl that optionally is substituted in one or more places, in the same way or differently, with M, heterocycloalkyl, or aryl or heteroaryl that optionally is substituted in one or more places with L, L means $C_1$-$C_8$-alkyl, $C_2$-$C_8$-alkenyl, $C_2$-$C_8$-alkinyl, $C_1$-$C_6$-perfluoroalkyl, $C_1$-$C_6$-perfluoroalkoxy, $C_1$-$C_6$-alkoxy-$C_1$-$C_6$-alkoxy, $(CH_2)_p$—$C_3$-$C_{10}$-cycloalkyl, $(CH_2)_p$-heterocycloalkyl, $(CH_2)_pCN$, $(CH_2)_pHal$, $(CH_2)_pNO_2$, $(CH_2)_p$—$C_6$-$C_{12}$-aryl, $(CH_2)_p$-heteroaryl, —$(CH_2)_pPO_3(R^b)_2$, —$(CH_2)_pNR^cR^d$, —$(CH_2)_pNR^eCOR^b$, —$(CH_2)_pNR^eCSR^b$, —$(CH_2)_pNR^eS(O)R^b$, —$(CH_2)_pNR^eS(O)_2R^b$, —$(CH_2)_pNR^eCONR^cR^d$, —$(CH_2)_pNR^eCOOR^b$, —$(CH_2)_pNR^eC(NH)NR^cR^d$, —$(CH_2)_pNR^eCSNR^cR^d$, —$(CH_2)_pNR^eS(O)NR^cR^d$, —$(CH_2)_pNR^eS(O)_2NR^cR^d$, —$(CH_2)_pCOR^b$, —$(CH_2)_pCSR^b$, —$(CH_2)_pS(O)R^b$, —$(CH_2)_pS(O)(NH)R^b$, —$(CH_2)_pS(O)_2R^b$, —$(CH_2)_pS(O)_2NR^cR^d$, —$(CH_2)_pSO_2OR^b$, —$(CH_2)_pCO_2R^b$, —$(CH_2)_pCONR^cR^d$, —$(CH_2)_pCSNR^cR^d$, —$(CH_2)_pOR^b$, —$(CH_2)_pSR^b$, —$(CH_2)_pCR^b(OH)$—$R^e$, —$(CH_2)_p$—C═$NOR^b$, —O—$(CH_2)_n$—O—, —O—$(CH_2)_n$—$CH_2$—, —O—CH═CH— or —$(CH_2)_{n+2}$—, whereby n=1 or 2, and the terminal oxygen atoms and/or carbon atoms are linked to directly adjacent ring-carbon atoms, M means $C_1$-$C_6$-alkyl or a group —$COR^b$, $CO_2R^b$, —O—$R^b$, or —$NR^cR^d$, whereby $R^b$ means a hydrogen or a $C_1$-$C_6$-alkyl, $C_2$-$C_8$-alkenyl, $C_2$-$C_8$-alkinyl, $C_3$-$C_{10}$-cycloalkyl, $C_6$-$C_{12}$-aryl or $C_1$-$C_3$-perfluoroalkyl, and $R^c$ and $R^d$, independently of one another, mean a hydrogen, $C_1$-$C_6$-alkyl, $C_2$-$C_8$-alkenyl, $C_2$-$C_8$-alkinyl, $C_3$-$C_{10}$-cycloalkyl, $C_6$-$C_{12}$-aryl, $C(O)R^b$ or a hydroxy group, whereby if $R^c$ is a hydroxy group, $R^d$ can be only one hydrogen, a $C_1$-$C_6$-alkyl, $C_2$-$C_8$-alkenyl, $C_2$-$C_8$-alkinyl, $C_3$-$C_{10}$-cycloalkyl or $C_6$-$C_{12}$-aryl and vice versa, and $R^e$ means a hydrogen, $C_1$-$C_6$-alkyl, $C_2$-$C_8$-alkenyl, $C_2$-$C_8$-alkinyl, $C_3$-$C_{10}$-cycloalkyl or $C_6$-$C_{12}$-aryl, and p can be a number from 0-6, or $R^3$ is a radical C═C—$R^gR^h$, whereby $R^g$ and $R^h$, independently of one another, are a hydrogen or a $C_1$-$C_8$-alkyl, $C_2$-$C_8$-alkenyl or $C_2$-$C_8$-alkinyl that optionally is substituted in one or more places, in the same way or differently, with X, in which X is a cyano, halogen, hydroxy, nitro, —C(O)$R^b$, $CO_2R^b$, —O—$R^b$, —C(O)—$NR^cR^d$, —$NR^cR^d$ with the meanings already further mentioned above for $R^b$, $R^c$ and $R^d$, and $R^{4a}$ and $R^{4b}$, independently of one another, mean a hydrogen atom, a $C_1$-$C_4$-alkyl, a $C_2$-$C_4$-alkenyl or together with the ring-carbon atom forming a 3- to 6-membered ring, A means a monocyclic or bicyclic, carbocyclic or heterocyclic aromatic ring, which optionally can be substituted in one or more places with $C_1$-$C_8$-alkyl, $C_2$-$C_8$-alkenyl, $C_2$-$C_8$-alkinyl, $C_1$-$C_6$-perfluoroalkyl, $C_1$-$C_6$-perfluoroalkoxy, $C_1$-$C_6$-alkoxy-$C_1$-$C_6$-alkyl, $C_1$-$C_6$-alkoxy-$C_1$-$C_6$-alkoxy, $(CH_2)_p$—$C_3$-$C_{10}$-cycloalkyl, $(CH_2)_p$-heterocycloalkyl, $(CH_2)_pCN$, $(CH_2)_pHal$, $(CH_2)_pNO_2$, $(CH_2)_p$—$C_6$-$C_{12}$-aryl, $(CH_2)_p$-heteroaryl, —$(CH_2)_pPO_3(R^b)_2$, —$(CH_2)_pNR^cR^d$, —$(CH_2)_pNR^eCOR^b$, —$(CH_2)_pNR^eCSR^b$, —$(CH_2)_pNR_eS(O)R^b$, —$(CH_2)NR^eS(O)_2R^b$, —$(CH_2)_pNR^eCONR^cR^d$, —$(CH_2)_pNR^e$-$COOR^b$, —$(CH_2)_pNR^eC(NH)NR^cR^d$, —$(CH_2)_pNR^eCSNR^cR^d$, —$(CH_2)_pNR^eS(O)NR^cR^d$, —$(CH_2)_pNR^eS(O)_2NR^cR^d$, —$(CH_2)_pCOR^b$, —$(CH_2)_pCSR^b$, —$(CH_2)_pS(O)R^b$, —$(CH_2)_pS(O)(NH)R^b$, $(CH_2)_pS(O)_2R^b$, —$(CH_2)_pS(O)_2NR^cR^d$, —$(CH_2)_pSO_2OR^b$, —$(CH_2)_pCO_2R^b$, —$(CH_2)_pCONR^cR^d$, —$(CH_2)_pCSNR^cR^d$, —$(CH_2)_pOR^b$, —$(CH_2)_pSR^b$, —$(CH_2)_pCR^b(OH)$—$R^d$, —$(CH_2)_p$—C═$NOR^b$, —O—$(CH_2)_n$—O—, —O—$(CH_2)_n$—$CH_2$—, —O—CH═CH— or —$(CH_2)_{n+2}$—, whereby n=1 or 2, and the terminal oxygen atoms and/or carbon atoms are linked to directly adjacent ring-carbon atoms, or A means a radical —$CO_2R^b$, $C(O)NR^cR^d$, $COR^b$, or A means an alkenyl group —$CR^5$═$CR^6R^7$, whereby $R^5$, $R^6$ and $R^7$ are the same or different and, independently of one another, mean hydrogen atoms, halogen atoms, aryl radicals or an unsubstituted or partially or completely fluorinated $C_1$-$C_5$-alkyl group, or A means an alkinyl group —C≡$CR^5$, with the meaning cited above for $R^5$ and B means a carbonyl group or a $CH_2$ group as well as their pharmaceutically acceptable salts.

The compounds of general formula I according to the invention can be present as different stereoisomers because of the presence of asymmetry centers. Both the racemates and the separately present stereoisomers are part of the subject of this invention.

In addition, this invention comprises the new compounds as pharmaceutical active ingredients, their production, their therapeutic application and pharmaceutical dispensing forms that contain the new substances.

The compounds of general formula (I) according to the invention or their pharmaceutically acceptable salts can be used for the production of a pharmaceutical agent, especially for treatment and prophylaxis of gynecological diseases, such as endometriosis, leiomyomas of the uterus, dysfunctional bleeding and dysmenorrhea. In addition, the compounds according to the invention can be used for the treatment and prophylaxis of hormone-dependent tumors, such as, for example, for breast, prostate and endometrial cancers.

The compounds of general formula (I) according to the invention or their pharmaceutically acceptable salts are suitable for use for female birth control or for female hormone replacement therapy.

A process for the production of the compounds of general formula (I), moreover, is also a subject of this invention. Substituent $R^3$ is introduced to a keto group by selective addition reaction of organometallic compounds such as lithium alkinylene or magnesium haloalkinylene. This results, either directly or after implementing additional modifications, in the compounds of general formula (I) according to the invention.

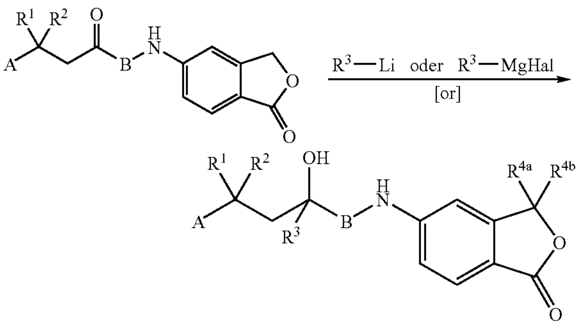

The production of the compounds according to the invention is carried out by selective addition of organometallic compounds to ketoamides, which were described in, e.g., laid-open specifications WO 200375915 and WO 9854159. The organometallic compounds can be, for example, lithium alkinyl compounds or magnesium haloalkinyl compounds. The latter are produced by, e.g., reaction of the corresponding alkines with butyllithium or Grignard compounds. Analogously to this, the corresponding organometallic alkenyl compounds can also be produced. The reactivity of the keto group in comparison to amidocarbonyl or to phthalide is in this case significantly higher, such that with suitable selection of the reaction conditions, a selective addition is achieved. As an alternative, the alkinyl or alkenyl radicals that are introduced as $R^3$ can also be further modified later. For these modifications, reactions that have become known to one skilled in the art, such as oxidation, reduction, substitution, alkylation, or palladium-catalyzed reaction, are suitable. Optionally present protective groups are cleaved off at a suitable time.

The nonsteroidal compounds of general formula I according to the invention have a strongly antagonistic or strongly partially agonistic action on the progesterone receptor. They exhibit a strong dissociation of action with respect to their bonding strength on the progesterone receptor and on the glucocorticoid receptor. While known progesterone receptor antagonists, such as Mifepristone (RU 486), in addition to the desired high binding affinity for the progesterone receptor likewise show a high affinity for the glucocorticoid receptor, the compounds according to the invention are distinguished by a very low glutocorticoid receptor bond with simultaneously present high progesterone receptor affinity.

The substituents of the compounds of general formula I according to the invention that are defined as groups can have the meanings below in each case:

$C_1$-$C_5$—, $C_1$-$C_6$— or $C_1$-$C_8$-alkyl groups are defined as straight or nonstraight, branched or unbranched alkyl radicals. In this case, for example, this is a methyl, ethyl, n-propyl, iso-propyl, n-, iso-, tert-butyl, an n-pentyl, 2,2-dimethylpropyl, 3-methylbutyl, hexyl, heptyl or octyl group.

In terms of $R^a$, in this case, the methyl, ethyl, n-propyl or n-butyl group as well as an n-pentyl group are preferred.

In terms of $R^1$ and $R^2$, methyl or ethyl is preferred.

According to the invention, a hydrogen is preferred for $R4^a$ and $R4^b$.

Alkenyl is defined as straight or nonstraight, branched or unbranched alkenyl radicals. In terms of the invention, a $C_2$-$C_8$-alkenyl group is defined, for example, as follows: vinyl, allyl, 3-buten-1-yl- or 2,3-dimethyl-2-propenyl. If aromatic compound A is substituted with a $C_2$-$C_8$-alkenyl radical, this is preferably a vinyl group.

Alkinyl is defined as straight or nonstraight, branched or unbranched alkinyl radicals. For example, an ethinyl, propinyl, butinyl, pentinyl, hexinyl or octinyl group, but preferably an ethinyl or propinyl group, is to stand for a $C_2$-$C_8$-alkinyl radical.

For $C_3$-$C_{10}$-cycloalkyl, for example, cyclopropane, cyclobutane, cyclopentane and cyclohexane can be mentioned. Cyclopropyl, cyclopentyl and cyclohexyl are preferred.

In terms of $R^a$, K or L, heterocycloalkyl is defined as 3- to 8-membered heterocycloalkyl radicals. Examples of heterocycloalkyl are morpholine, tetrahydrofuran, pyran, piperazine, piperidine, pyrrolidine, oxirane, oxetane, aziridine, dioxolane and dioxane. In this case, the position of the heteroatom in relation to the point of linkage can be any chemically possible position.

For example, methoxymethoxy, ethoxymethoxy or 2-methoxyethoxy can stand for a $C_1$-$C_6$-alkoxyl-$C_1$-$C_6$-alkoxy group.

In terms of the invention, a radical $OR^b$ is a hydroxy, methoxy, ethoxy, n-propoxy, iso-propoxy, n-, iso-, or tert-butoxy group, or an n-pentoxy, 2,2-dimethylpropoxy or 3-methylbutoxy group. Hydroxy, methoxy and ethoxy are preferred.

For a partially or completely fluorinated $C_1$-$C_5$-alkyl group, the perfluorinated alkyl groups that appear above are considered. Of the latter, primarily the trifluoromethyl group or the pentafluoroethyl group as well as as partially fluorinated alkyl groups, for example the 5,5,4,4-pentafluoropentyl group or the 5,5,5,4,4,3,3-heptafluoropentyl group, are preferred.

A fluorine, chlorine, bromine or iodine atom can stand for a halogen atom. Preferred here is fluorine, chlorine or bromine.

If $R^1$ and $R^2$ together with the C atom of the chain form a 3- to 7-membered ring, this is, for example, a cyclopropyl, cyclobutyl, cyclopentyl or cyclohexyl ring. The cyclopropyl ring as well as the cyclopentyl ring are preferred.

The monocyclic or bicyclic carbocyclic aromatic ring A, which can be substituted in several places, is a carbocyclic or heterocyclic aryl radical.

In the first case, it is, for example, a phenyl or naphthyl radical, preferably a phenyl radical.

As a heterocyclic radical, for example, a monocyclic heterocyclic radical, for example the thienyl, furyl, pyranyl, pyrrolyl, imidazolyl, pyrazolyl, pyridyl, pyrazinyl, pyrimidinyl, pyridazinyl, thiazolyl, oxazolyl, furazanyl, pyrrolinyl, imidazolinyl, pyrazolinyl, thiazolinyl, triazolyl, or tetrazolyl radical, and specifically all possible isomers relative to the positions of the heteroatoms, can be used.

In terms of $R^3$, an aryl radical is an optionally substituted phenyl, 1- or 2-naphthyl radical, whereby the phenyl radical is preferred. Examples of a heteroaryl radical are the 2-, 3- or 4-pyridinyl radical, the 2- or 3-furyl radical, the 2- or 3-thienyl radical, the 2- or 3-pyrrolyl radical, the 2-, 4- or 5-imidazolyl radical, the pyrazinyl radical, the 2-, 4- or 5-pyrimidinyl radical or the 3- or 4-pyridazinyl radical.

The number p for the $(CH_2)_p$ radical can be a number from 0 to 6, preferably 0 to 2. "Radicals" are defined according to the invention as all functional groups that are presented in connection with $(CH_2)_p$.

In the case that the compounds of general formula I (B=—$CH_2$—) are present as salts, this can be, for example, in the form of hydrochloride, sulfate, nitrate, tartrate, citrate, fumarate, succinate or benzoate.

If the compounds according to the invention are present as racemic mixtures, they can be separated into pure, optically active forms according to methods of racemate separation that are familiar to one skilled in the art. For example, the racemic mixtures can be separated into pure isomers by chromatography on an even optically active carrier material (CHIRALPAK AD®). It is also possible to esterify the free hydroxy group in a racemic compound of general formula I with an optically active acid and to separate the diastereomeric esters that are obtained by fractionated crystallization or by chromatography and to saponify the separated esters in each case to form the optically pure isomers. As an optically active acid, for example, mandelic acid, camphorsulfonic acid or tartaric acid can be used.

The compounds that are mentioned below as well as the use thereof are preferred according to the invention:

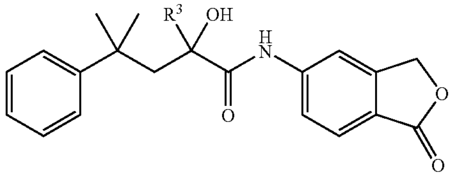

| No. | Racemic or Enantiomer | R3 |
|---|---|---|
| 1 | rac | 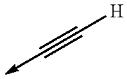 |
| 2 | + | |
| 3 | – | |
| 4 | rac | 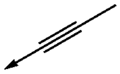 |
| 5 | + | |
| 6 | – | |
| 7 | rac | 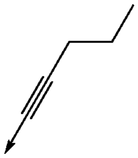 |
| 8 | + | |
| 9 | – | |
| 10 | rac | 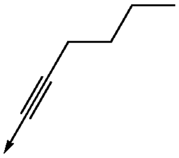 |
| 11 | + | |
| 12 | – | |
| 13 | rac | 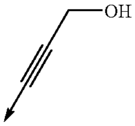 |
| 14 | + | |
| 15 | – | |
| 16 | rac | 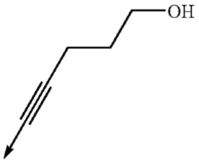 |
| 17 | + | |
| 18 | – | |
| 19 | rac | 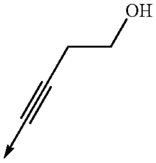 |
| 20 | + | |
| 21 | – | |

-continued

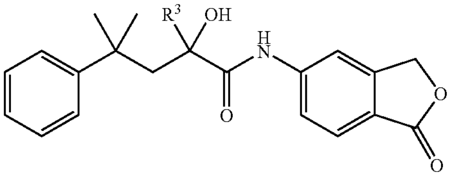

| No. | Racemic or Enantiomer | R3 |
|---|---|---|
| 22 | rac | 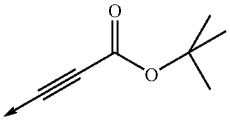 |
| 23 | + | |
| 24 | – | |
| 25 | rac | 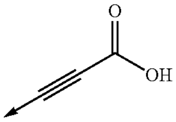 |
| 26 | + | |
| 27 | – | |
| 28 | rac | 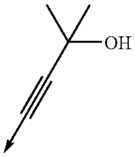 |
| 29 | + | |
| 30 | – | |
| 31 | rac | 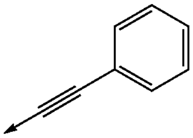 |
| 32 | + | |
| 33 | – | |
| 34 | rac | 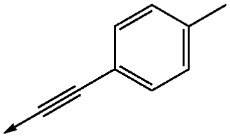 |
| 35 | + | |
| 36 | – | |
| 37 | rac | 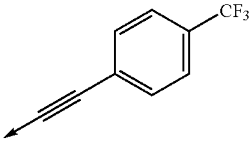 |
| 38 | + | |
| 39 | – | |
| 40 | rac | 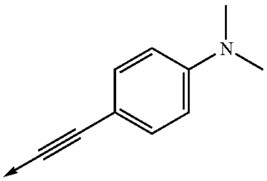 |
| 41 | + | |
| 42 | – | |
| 43 | rac | 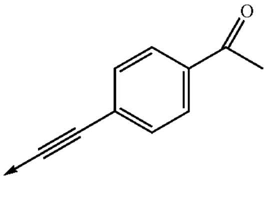 |
| 44 | + | |
| 45 | – | |

-continued
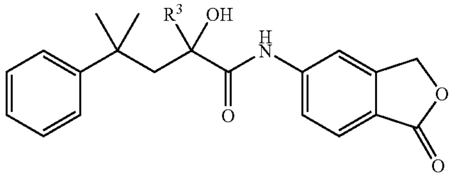
| No. | Racemic or Enantiomer | R3 |
|---|---|---|
| 46 | rac | 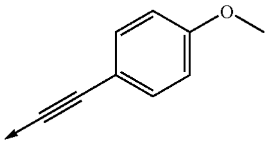 |
| 47 | + | |
| 48 | − | |
| 49 | rac | 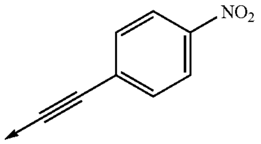 |
| 50 | + | |
| 51 | − | |
| 52 | rac | 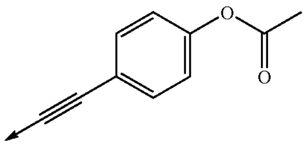 |
| 53 | + | |
| 54 | − | |
| 55 | rac | 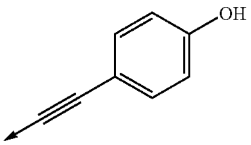 |
| 56 | + | |
| 57 | − | |
| 58 | rac | 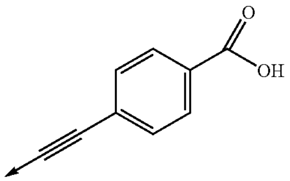 |
| 59 | + | |
| 60 | − | |
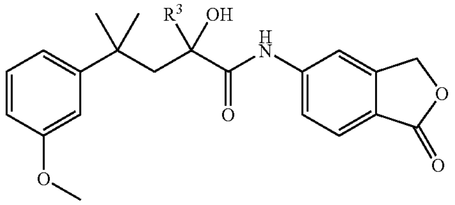
| No. | Racemic or Enantiomer | R3 |
|---|---|---|
| 61 | rac | 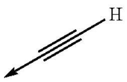 |
| 62 | + | |
| 63 | − | |
| 64 | rac | 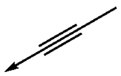 |
| 65 | + | |
| 66 | − | |
-continued
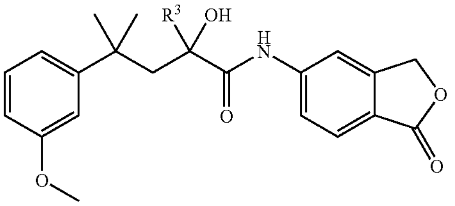
| No. | Racemic or Enantiomer | R3 |
|---|---|---|
| 67 | rac | 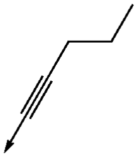 |
| 68 | + | |
| 69 | − | |
| 70 | rac | 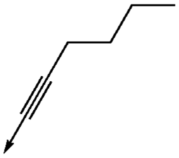 |
| 71 | + | |
| 72 | − | |
| 73 | rac | 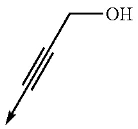 |
| 74 | + | |
| 75 | − | |
| 76 | rac | 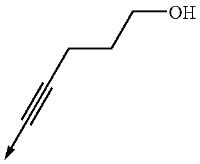 |
| 77 | + | |
| 78 | − | |
| 79 | rac | 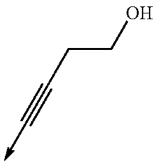 |
| 80 | + | |
| 81 | − | |
| 82 | rac | 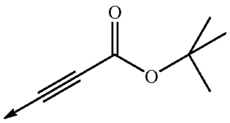 |
| 83 | + | |
| 84 | − | |
| 85 | rac | 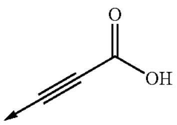 |
| 86 | + | |
| 87 | − | |
| 88 | rac | 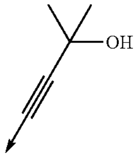 |
| 89 | + | |
| 90 | − | |

-continued
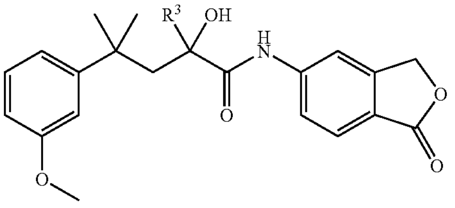
| No. | Racemic or Enantiomer | R3 |
|---|---|---|
| 91 | rac | 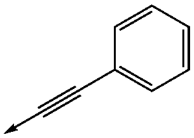 |
| 92 | + | |
| 93 | − | |
| 94 | rac | 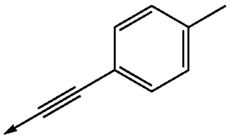 |
| 95 | + | |
| 96 | − | |
| 97 | rac | 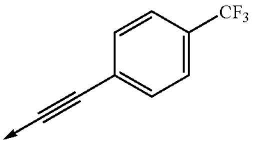 |
| 98 | + | |
| 99 | − | |
| 100 | rac | 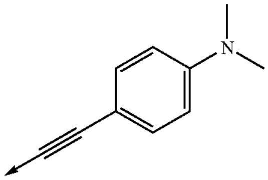 |
| 101 | + | |
| 102 | − | |
| 103 | rac | 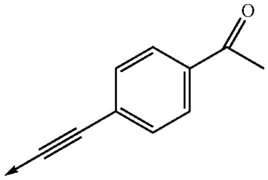 |
| 104 | + | |
| 105 | − | |
| 106 | rac | 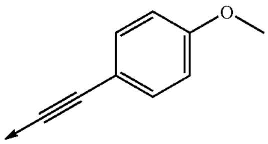 |
| 107 | + | |
| 108 | − | |
| 109 | rac | 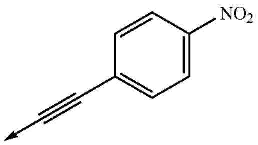 |
| 110 | + | |
| 111 | − | |
| 112 | rac | 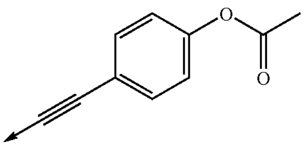 |
| 113 | + | |
| 114 | − | |
-continued
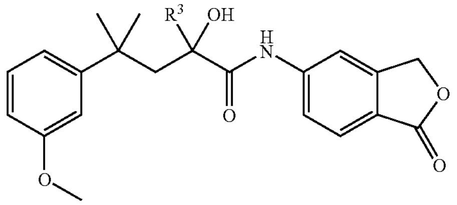
| No. | Racemic or Enantiomer | R3 |
|---|---|---|
| 115 | rac | 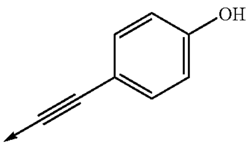 |
| 116 | + | |
| 117 | − | |
| 118 | rac | 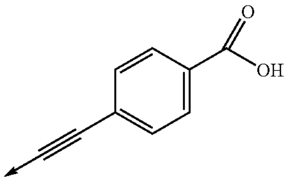 |
| 119 | + | |
| 120 | − | |
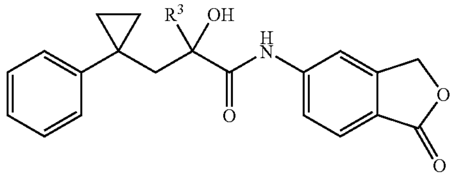
| No. | Racemic or Enantiomer | R3 |
|---|---|---|
| 121 | rac | 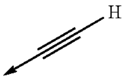 |
| 122 | + | |
| 123 | − | |
| 124 | rac | 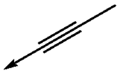 |
| 125 | + | |
| 126 | − | |
| 127 | rac | 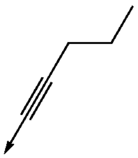 |
| 128 | + | |
| 129 | − | |
| 130 | rac | 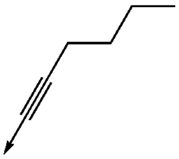 |
| 131 | + | |
| 132 | − | |

-continued
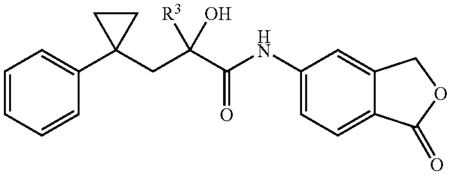
| No. | Racemic or Enantiomer | R3 |
|---|---|---|
| 133 | rac | 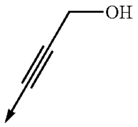 |
| 134 | + | |
| 135 | – | |
| 136 | rac | 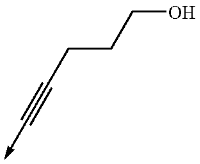 |
| 137 | + | |
| 138 | – | |
| 139 | rac | 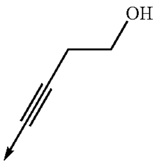 |
| 140 | + | |
| 141 | – | |
| 142 | rac | 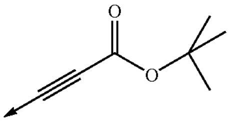 |
| 143 | + | |
| 144 | – | |
| 145 | rac | 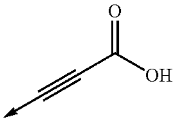 |
| 146 | + | |
| 147 | – | |
| 148 | rac | 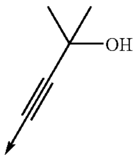 |
| 149 | + | |
| 150 | – | |
| 151 | rac | 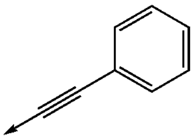 |
| 152 | + | |
| 153 | – | |
| 154 | rac | 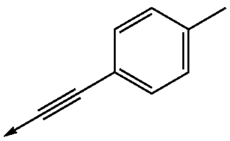 |
| 155 | + | |
| 156 | – | |
-continued
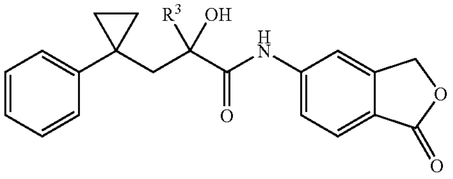
| No. | Racemic or Enantiomer | R3 |
|---|---|---|
| 157 | rac | 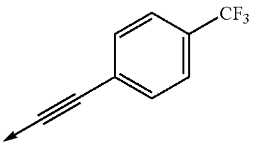 |
| 158 | + | |
| 159 | – | |
| 160 | rac | 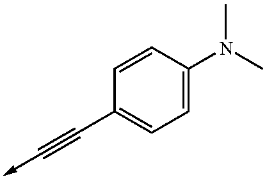 |
| 161 | + | |
| 162 | – | |
| 163 | rac | 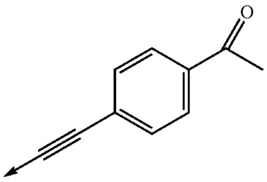 |
| 164 | + | |
| 165 | – | |
| 166 | rac | 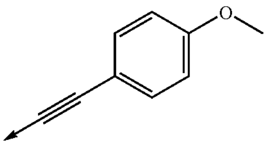 |
| 167 | + | |
| 168 | – | |
| 169 | rac | 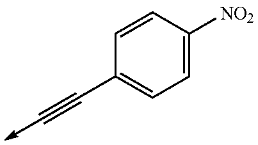 |
| 170 | + | |
| 171 | – | |
| 172 | rac | 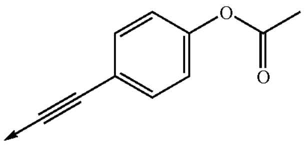 |
| 173 | + | |
| 174 | – | |
| 175 | rac | 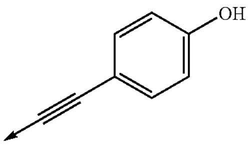 |
| 176 | + | |
| 177 | – | |

-continued
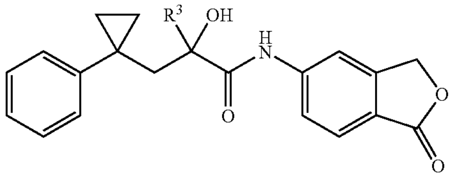
| No. | Racemic or Enantiomer | R3 |
|---|---|---|
| 178 | rac | 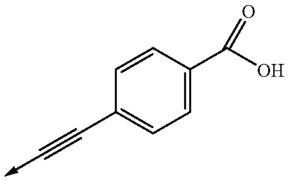 |
| 179 | + | |
| 180 | − | |
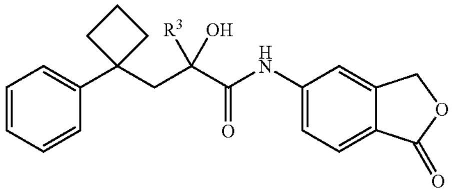
| No. | Racemic or Enantiomer | R3 |
|---|---|---|
| 181 | rac | 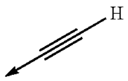 |
| 182 | + | |
| 183 | − | |
| 184 | rac | 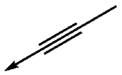 |
| 185 | + | |
| 186 | − | |
| 187 | rac | 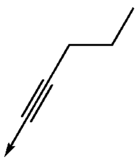 |
| 188 | + | |
| 189 | − | |
| 190 | rac | 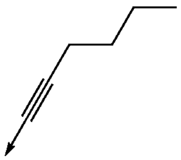 |
| 191 | + | |
| 192 | − | |
| 193 | rac | 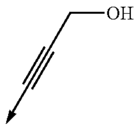 |
| 194 | + | |
| 195 | − | |
-continued
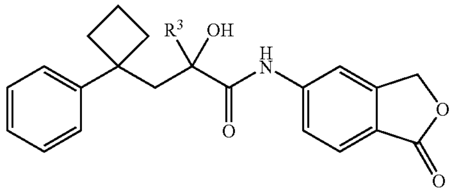
| No. | Racemic or Enantiomer | R3 |
|---|---|---|
| 196 | rac | 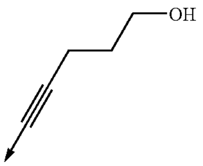 |
| 197 | + | |
| 198 | − | |
| 199 | rac | 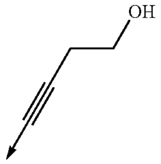 |
| 200 | + | |
| 201 | − | |
| 202 | rac | 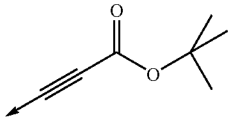 |
| 203 | + | |
| 204 | − | |
| 205 | rac | 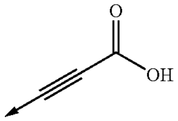 |
| 206 | + | |
| 207 | − | |
| 208 | rac | 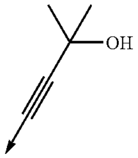 |
| 209 | + | |
| 210 | − | |
| 211 | rac | 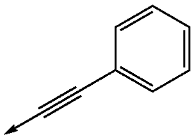 |
| 212 | + | |
| 213 | − | |
| 214 | rac | 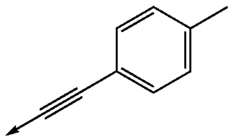 |
| 215 | + | |
| 216 | − | |
| 217 | rac | 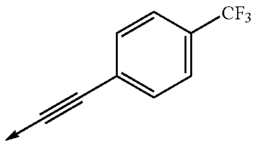 |
| 218 | + | |
| 219 | − | |

-continued
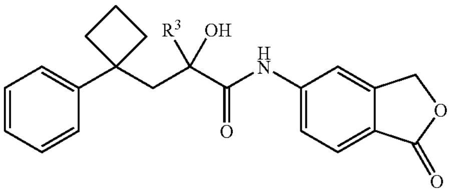
| No. | Racemic or Enantiomer | R3 |
|---|---|---|
| 220 | rac | 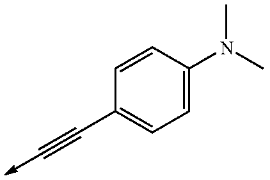 |
| 221 | + | |
| 222 | − | |
| 223 | rac | 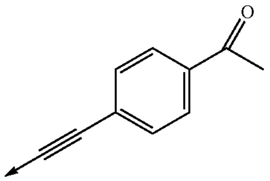 |
| 224 | + | |
| 225 | − | |
| 226 | rac | 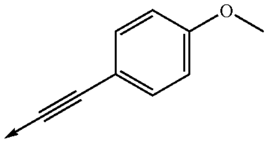 |
| 227 | + | |
| 228 | − | |
| 229 | rac | 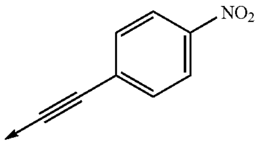 |
| 230 | + | |
| 231 | − | |
| 232 | rac | 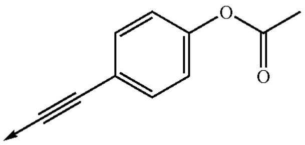 |
| 233 | + | |
| 234 | − | |
| 235 | rac | 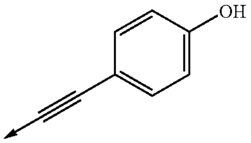 |
| 236 | + | |
| 237 | − | |
| 238 | rac | 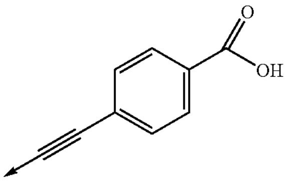 |
| 239 | + | |
| 240 | − | |
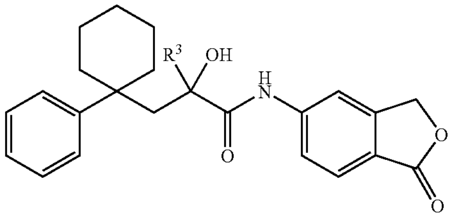
| No. | Racemic or Enantiomer | R3 |
|---|---|---|
| 241 | rac | 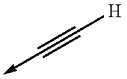 |
| 242 | + | |
| 243 | − | |
| 244 | rac | 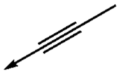 |
| 245 | + | |
| 246 | − | |
| 247 | rac | 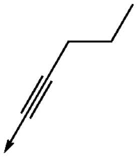 |
| 248 | + | |
| 249 | − | |
| 250 | rac | 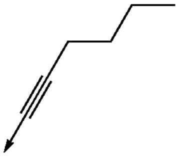 |
| 251 | + | |
| 252 | − | |
| 253 | rac | 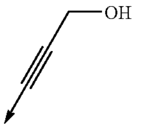 |
| 254 | + | |
| 255 | − | |
| 256 | rac | 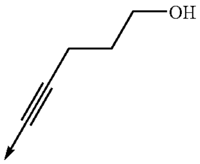 |
| 257 | + | |
| 258 | − | |
| 259 | rac | 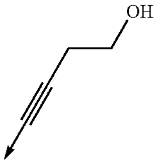 |
| 260 | + | |
| 261 | − | |
| 262 | rac | 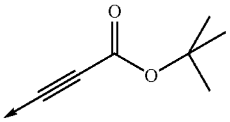 |
| 263 | + | |
| 264 | − | |
| 265 | rac | 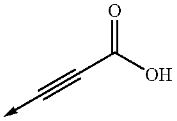 |
| 266 | + | |
| 267 | − | |

-continued
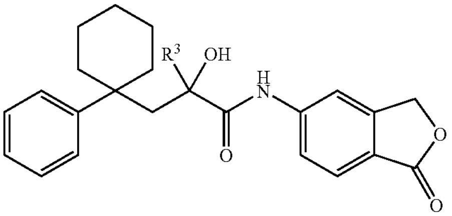
| No. | Racemic or Enantiomer | R3 |
|---|---|---|
| 268 | rac | 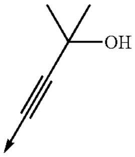 |
| 269 | + | |
| 270 | − | |
| 271 | rac | 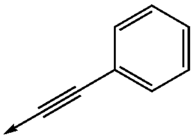 |
| 272 | + | |
| 273 | − | |
| 274 | rac | 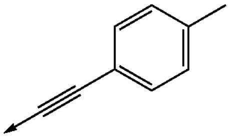 |
| 275 | + | |
| 276 | − | |
| 277 | rac | 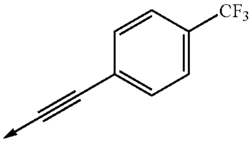 |
| 278 | + | |
| 279 | − | |
| 280 | rac | 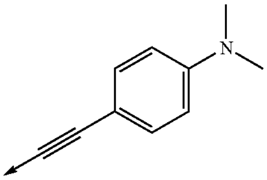 |
| 281 | + | |
| 282 | − | |
| 283 | rac | 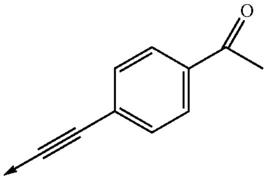 |
| 284 | + | |
| 285 | − | |
| 286 | rac | 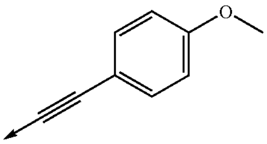 |
| 287 | + | |
| 288 | − | |
| 289 | rac | 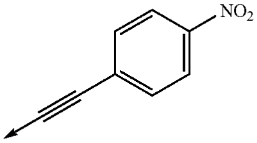 |
| 290 | + | |
| 291 | − | |
-continued
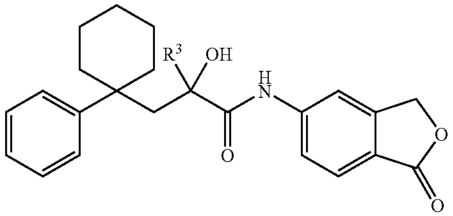
| No. | Racemic or Enantiomer | R3 |
|---|---|---|
| 292 | rac | 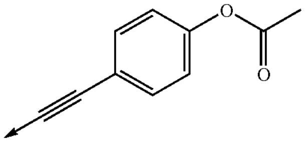 |
| 293 | + | |
| 294 | − | |
| 295 | rac | 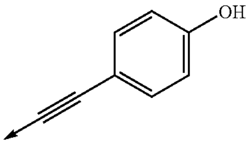 |
| 296 | + | |
| 297 | − | |
| 298 | rac | 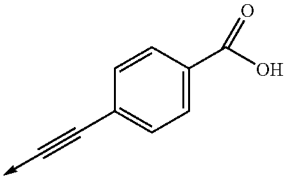 |
| 299 | + | |
| 300 | − | |
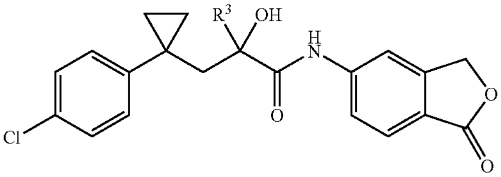
| No. | Racemic or Enantiomer | R3 |
|---|---|---|
| 301 | rac | 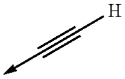 |
| 302 | + | |
| 303 | − | |
| 304 | rac | 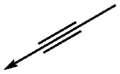 |
| 305 | + | |
| 306 | − | |
| 307 | rac | 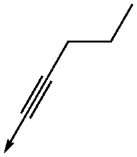 |
| 308 | + | |
| 309 | − | |

-continued
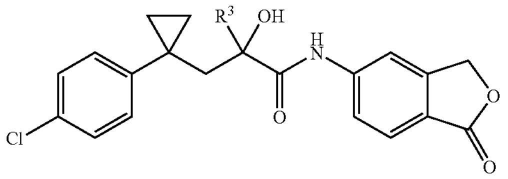
| No. | Racemic or Enantiomer | R3 |
|---|---|---|
| 310 | rac | 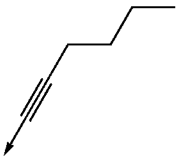 |
| 311 | + | |
| 312 | − | |
| 313 | rac | 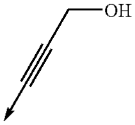 |
| 314 | + | |
| 315 | − | |
| 316 | rac | 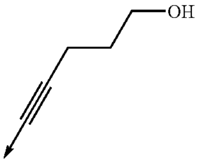 |
| 317 | + | |
| 318 | − | |
| 319 | rac | 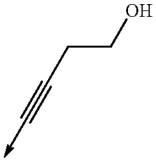 |
| 320 | + | |
| 321 | − | |
| 322 | rac | 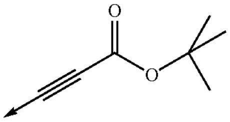 |
| 323 | + | |
| 324 | − | |
| 325 | rac | 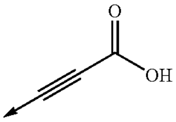 |
| 326 | + | |
| 327 | − | |
| 328 | rac | 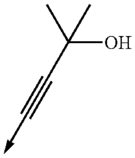 |
| 329 | + | |
| 330 | − | |
| 331 | rac | 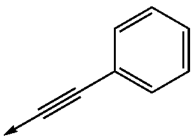 |
| 332 | + | |
| 333 | − | |
-continued
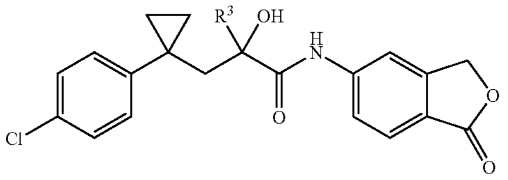
| No. | Racemic or Enantiomer | R3 |
|---|---|---|
| 334 | rac | 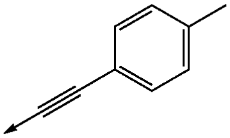 |
| 335 | + | |
| 336 | − | |
| 337 | rac | 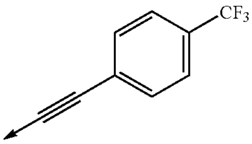 |
| 338 | + | |
| 339 | − | |
| 340 | rac | 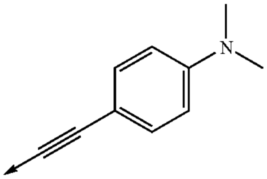 |
| 341 | + | |
| 342 | − | |
| 343 | rac | 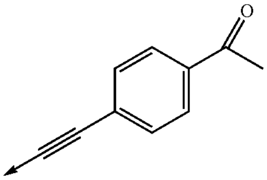 |
| 344 | + | |
| 345 | − | |
| 346 | rac | 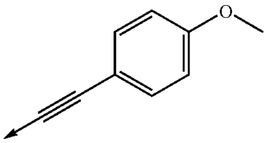 |
| 347 | + | |
| 348 | − | |
| 349 | rac | 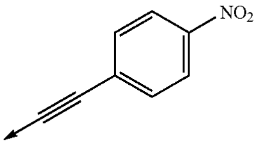 |
| 350 | + | |
| 351 | − | |
| 352 | rac | 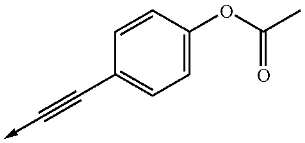 |
| 353 | + | |
| 354 | − | |
| 355 | rac | 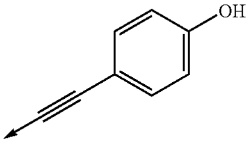 |
| 356 | + | |
| 357 | − | |

-continued

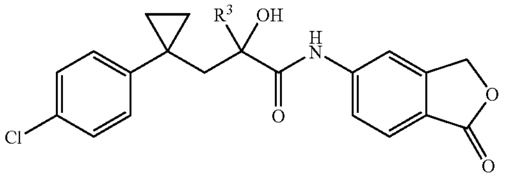

| No. | Racemic or Enantiomer | R3 |
|---|---|---|
| 358<br>359<br>360 | rac<br>+<br>− | 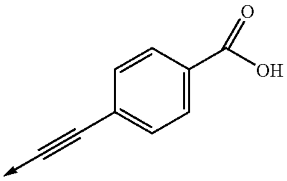 |

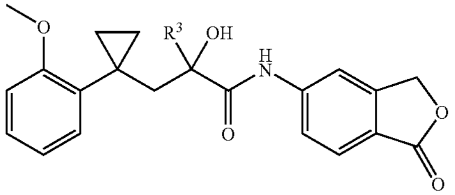

| No. | Racemic or Enantiomer | R3 |
|---|---|---|
| 361<br>362<br>363 | rac<br>+<br>− | 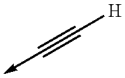 |
| 364<br>365<br>366 | rac<br>+<br>− | 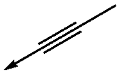 |
| 367<br>368<br>369 | rac<br>+<br>− | 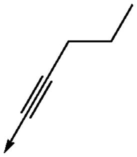 |
| 370<br>371<br>372 | rac<br>+<br>− | 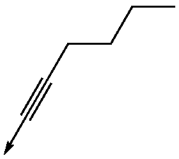 |
| 373<br>374<br>375 | rac<br>+<br>− | 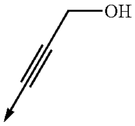 |

-continued

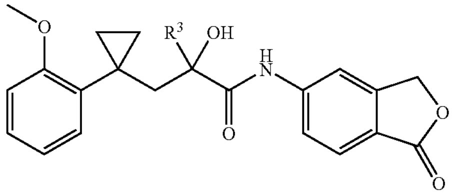

| No. | Racemic or Enantiomer | R3 |
|---|---|---|
| 376<br>377<br>378 | rac<br>+<br>− | 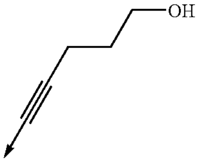 |
| 379<br>380<br>381 | rac<br>+<br>− | 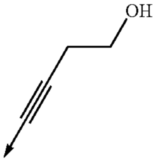 |
| 382<br>383<br>384 | rac<br>+<br>− | 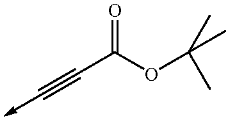 |
| 385<br>386<br>387 | rac<br>+<br>− | 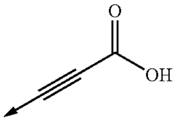 |
| 388<br>389<br>390 | rac<br>+<br>− | 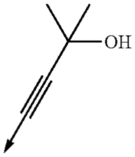 |
| 391<br>392<br>393 | rac<br>+<br>− | 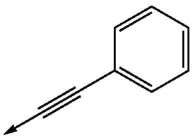 |
| 394<br>395<br>396 | rac<br>+<br>− | 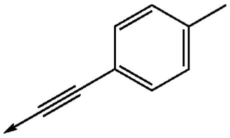 |
| 397<br>398<br>399 | rac<br>+<br>− | 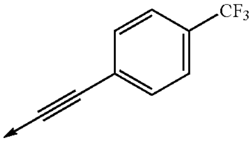 |

-continued
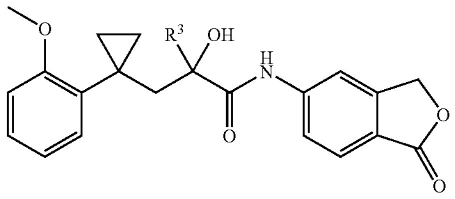
| No. | Racemic or Enantiomer | R3 |
|---|---|---|
| 400 | rac | 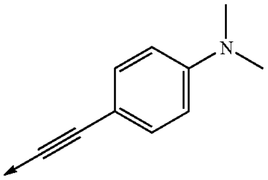 |
| 401 | + | |
| 402 | − | |
| 403 | rac | 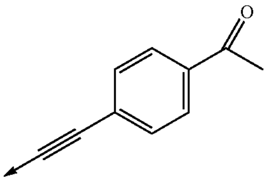 |
| 404 | + | |
| 405 | − | |
| 406 | rac | 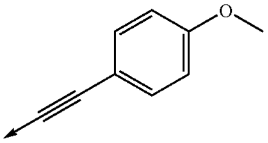 |
| 407 | + | |
| 408 | − | |
| 409 | rac | 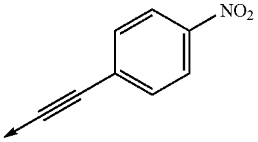 |
| 410 | + | |
| 411 | − | |
| 412 | rac | 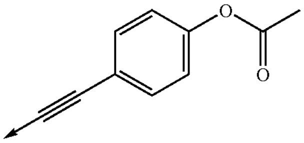 |
| 413 | + | |
| 414 | − | |
| 415 | rac | 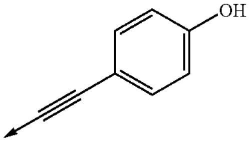 |
| 416 | + | |
| 417 | − | |
| 418 | rac | 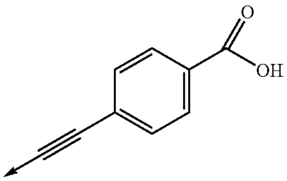 |
| 419 | + | |
| 420 | − | |
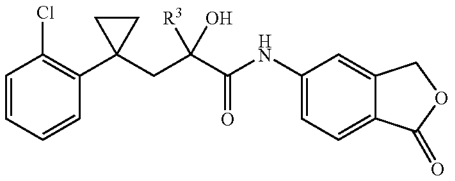
| No. | Racemic or Enantiomer | R3 |
|---|---|---|
| 421 | rac | 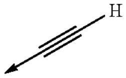 |
| 422 | + | |
| 423 | − | |
| 424 | rac | 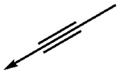 |
| 425 | + | |
| 426 | − | |
| 427 | rac | 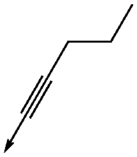 |
| 428 | + | |
| 429 | − | |
| 430 | rac | 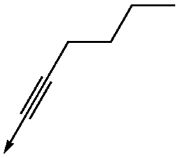 |
| 431 | + | |
| 432 | − | |
| 433 | rac | 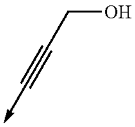 |
| 434 | + | |
| 435 | − | |
| 436 | rac | 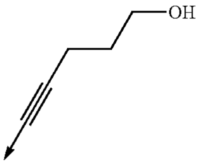 |
| 437 | + | |
| 438 | − | |
| 439 | rac | 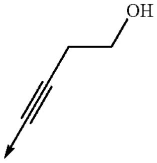 |
| 440 | + | |
| 441 | − | |
| 442 | rac | 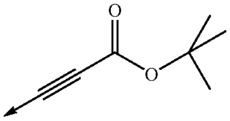 |
| 443 | + | |
| 444 | − | |
| 445 | rac | 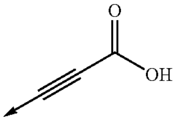 |
| 446 | + | |
| 447 | − | |

-continued
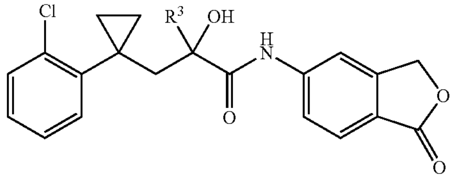
| No. | Racemic or Enantiomer | R3 |
|---|---|---|
| 448 | rac | 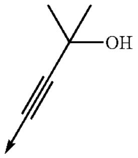 |
| 449 | + | |
| 450 | – | |
| 451 | rac | 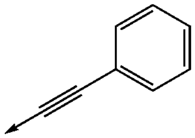 |
| 452 | + | |
| 453 | – | |
| 454 | rac | 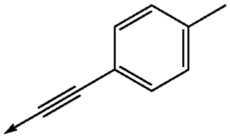 |
| 455 | + | |
| 456 | – | |
| 457 | rac | 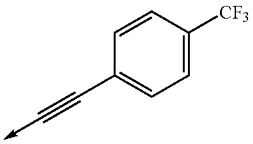 |
| 458 | + | |
| 459 | – | |
| 460 | rac | 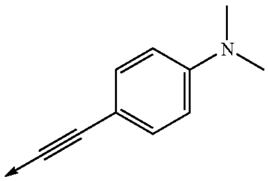 |
| 461 | + | |
| 462 | – | |
| 463 | rac | 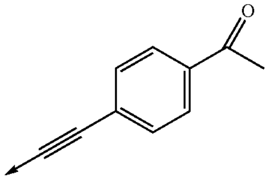 |
| 464 | + | |
| 465 | – | |
| 466 | rac | 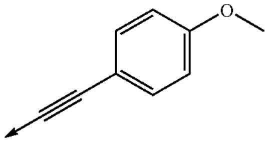 |
| 467 | + | |
| 468 | – | |
| 469 | rac | 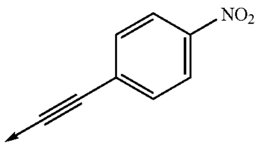 |
| 470 | + | |
| 471 | – | |
-continued
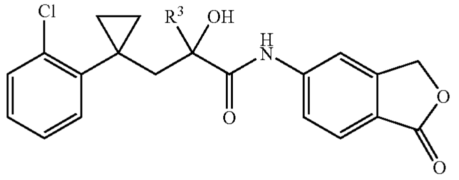
| No. | Racemic or Enantiomer | R3 |
|---|---|---|
| 472 | rac | 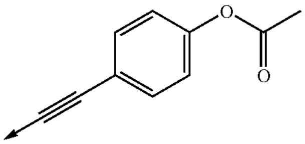 |
| 473 | + | |
| 474 | – | |
| 475 | rac | 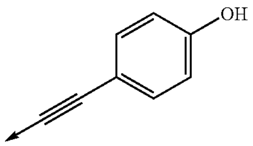 |
| 476 | + | |
| 477 | – | |
| 478 | rac | 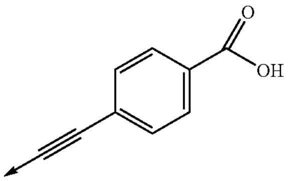 |
| 479 | + | |
| 480 | – | |
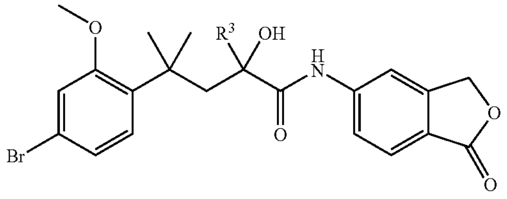
| No. | Racemic or Enantiomer | R3 |
|---|---|---|
| 481 | rac | 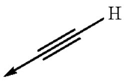 |
| 482 | + | |
| 483 | – | |
| 484 | rac | 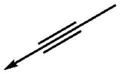 |
| 485 | + | |
| 486 | – | |
| 487 | rac | 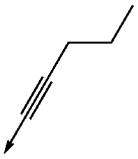 |
| 488 | + | |
| 489 | – | |

-continued
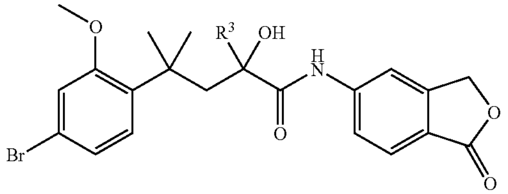
| No. | Racemic or Enantiomer | R3 |
|---|---|---|
| 490 | rac | 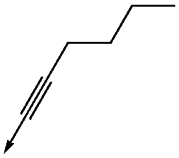 |
| 491 | + | |
| 492 | − | |
| 493 | rac | 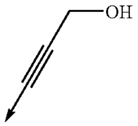 |
| 494 | + | |
| 495 | − | |
| 496 | rac | 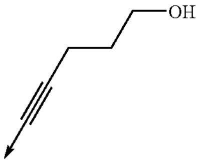 |
| 497 | + | |
| 498 | − | |
| 499 | rac | 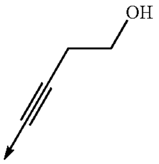 |
| 500 | + | |
| 501 | − | |
| 502 | rac | 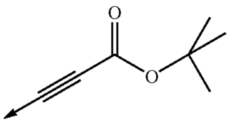 |
| 503 | + | |
| 504 | − | |
| 505 | rac | 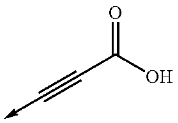 |
| 506 | + | |
| 507 | − | |
| 508 | rac | 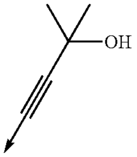 |
| 509 | + | |
| 510 | − | |
| 511 | rac | 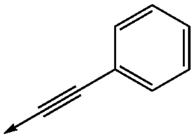 |
| 512 | + | |
| 513 | − | |
-continued
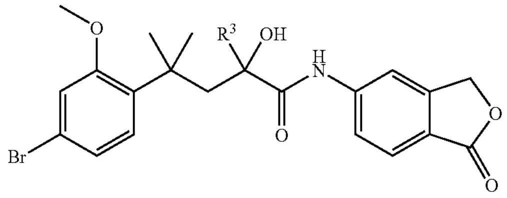
| No. | Racemic or Enantiomer | R3 |
|---|---|---|
| 214 | rac | 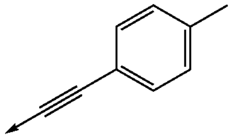 |
| 515 | + | |
| 516 | − | |
| 517 | rac | 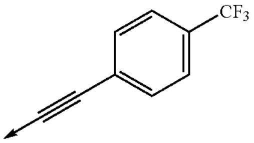 |
| 518 | + | |
| 519 | − | |
| 520 | rac | 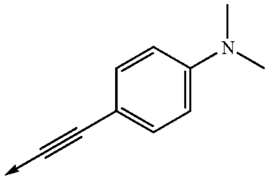 |
| 521 | + | |
| 522 | − | |
| 523 | rac | 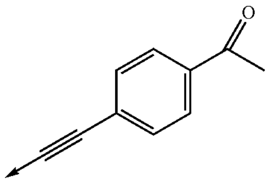 |
| 524 | + | |
| 525 | − | |
| 526 | rac | 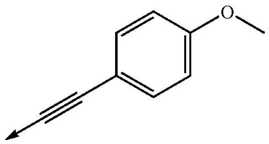 |
| 227 | + | |
| 528 | − | |
| 529 | rac | 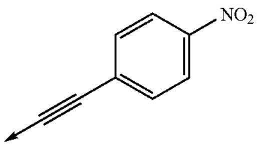 |
| 530 | + | |
| 531 | − | |
| 532 | rac | 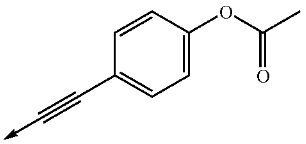 |
| 533 | + | |
| 534 | − | |
| 535 | rac | 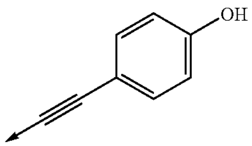 |
| 536 | + | |
| 537 | − | |

-continued
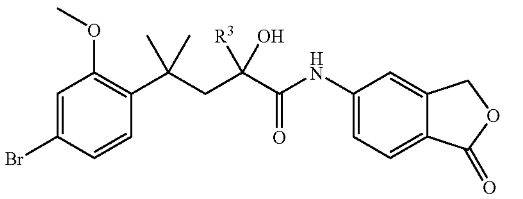
| No. | Racemic or Enantiomer | R3 |
| --- | --- | --- |
| 538 | rac | 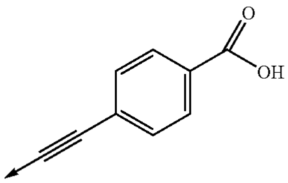 |
| 539 | + | |
| 540 | − | |
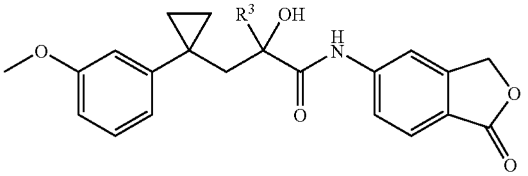
| No. | Racemic or Enantiomer | R3 |
| --- | --- | --- |
| 541 | rac | 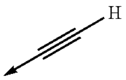 |
| 542 | + | |
| 543 | − | |
| 544 | rac | 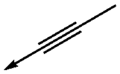 |
| 545 | + | |
| 546 | − | |
| 547 | rac | 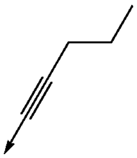 |
| 548 | + | |
| 549 | − | |
| 550 | rac | 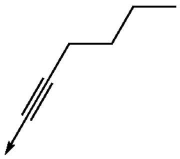 |
| 551 | + | |
| 552 | − | |
| 553 | rac | 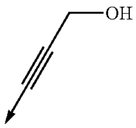 |
| 554 | + | |
| 555 | − | |
-continued
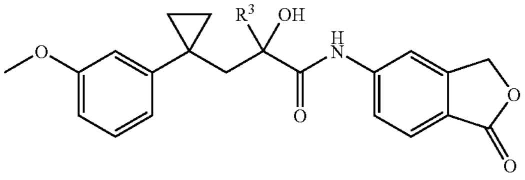
| No. | Racemic or Enantiomer | R3 |
| --- | --- | --- |
| 556 | rac | 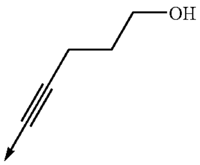 |
| 557 | + | |
| 558 | − | |
| 559 | rac | 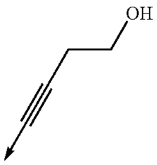 |
| 560 | + | |
| 561 | − | |
| 562 | rac | 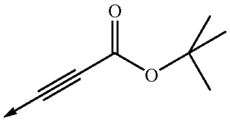 |
| 563 | + | |
| 564 | − | |
| 565 | rac | 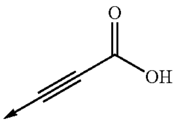 |
| 566 | + | |
| 567 | − | |
| 568 | rac | 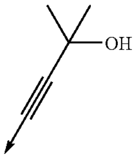 |
| 569 | + | |
| 570 | − | |
| 571 | rac | 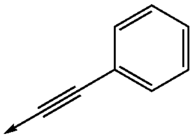 |
| 572 | + | |
| 573 | − | |
| 574 | rac | 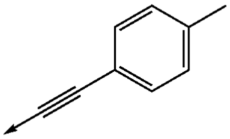 |
| 575 | + | |
| 576 | − | |
| 577 | rac | 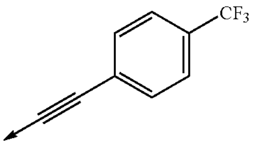 |
| 578 | + | |
| 579 | − | |

-continued
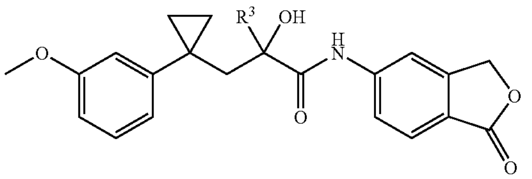
| No. | Racemic or Enantiomer | R3 |
|---|---|---|
| 580 | rac | 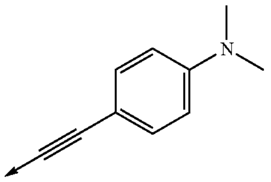 |
| 581 | + | |
| 582 | − | |
| 583 | rac | 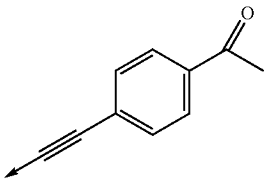 |
| 584 | + | |
| 585 | − | |
| 586 | rac | 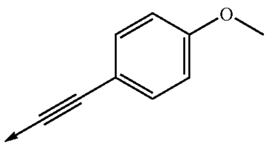 |
| 587 | + | |
| 588 | − | |
| 589 | rac | 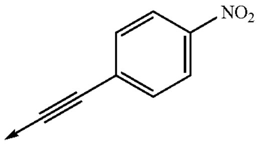 |
| 590 | + | |
| 591 | − | |
| 592 | rac | 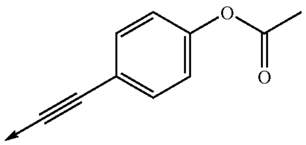 |
| 593 | + | |
| 594 | − | |
| 595 | rac | 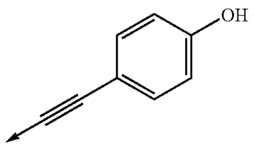 |
| 596 | + | |
| 597 | − | |
| 598 | rac | 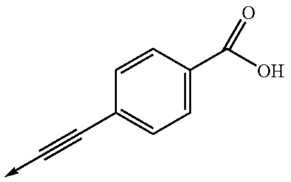 |
| 599 | + | |
| 600 | − | |
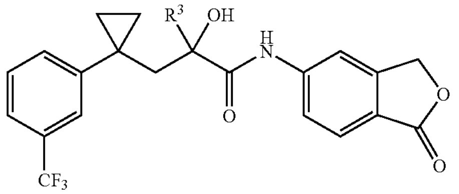
| No. | Racemic or Enantiomer | R3 |
|---|---|---|
| 601 | rac | 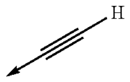 |
| 602 | + | |
| 603 | − | |
| 604 | rac | 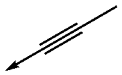 |
| 605 | + | |
| 606 | − | |
| 607 | rac | 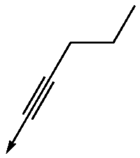 |
| 608 | + | |
| 609 | − | |
| 610 | rac | 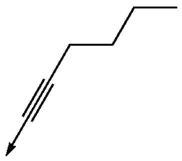 |
| 611 | + | |
| 612 | − | |
| 613 | rac | 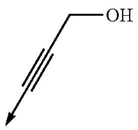 |
| 614 | + | |
| 615 | − | |
| 616 | rac | 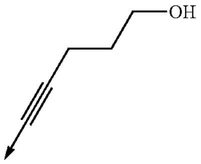 |
| 617 | + | |
| 618 | − | |
| 619 | rac | 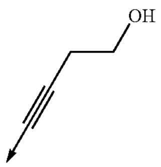 |
| 620 | + | |
| 621 | − | |
| 622 | rac | 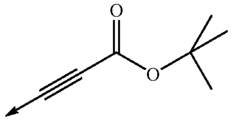 |
| 623 | + | |
| 624 | − | |
| 625 | rac | 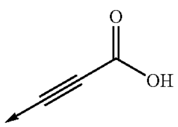 |
| 626 | + | |
| 627 | − | |

-continued

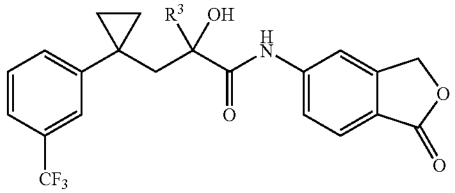

| No. | Racemic or Enantiomer | R3 |
|---|---|---|
| 628<br>629<br>630 | rac<br>+<br>− | 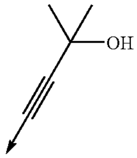 |
| 631<br>632<br>633 | rac<br>+<br>− | 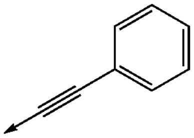 |
| 634<br>635<br>636 | rac<br>+<br>− | 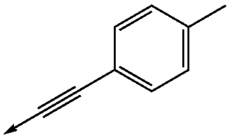 |
| 637<br>638<br>639 | rac<br>+<br>− | 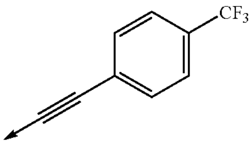 |
| 640<br>641<br>642 | rac<br>+<br>− | 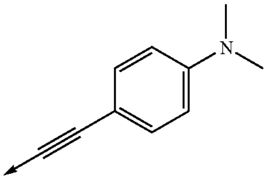 |
| 643<br>644<br>645 | rac<br>+<br>− | 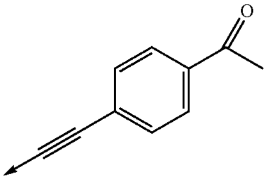 |
| 646<br>647<br>648 | rac<br>+<br>− | 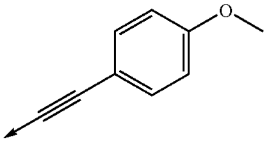 |
| 649<br>650<br>651 | rac<br>+<br>− | 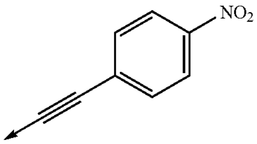 |

-continued

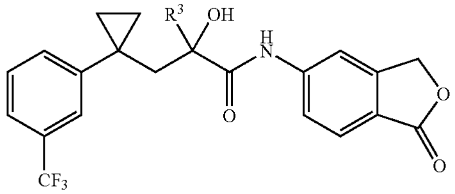

| No. | Racemic or Enantiomer | R3 |
|---|---|---|
| 652<br>653<br>654 | rac<br>+<br>− | 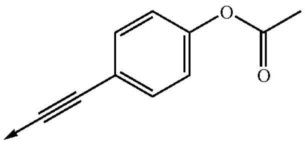 |
| 655<br>656<br>657 | rac<br>+<br>− | 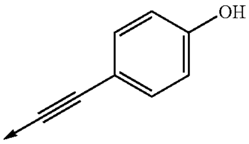 |
| 658<br>659<br>660 | rac<br>+<br>− | 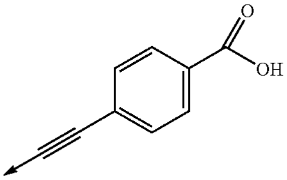 |

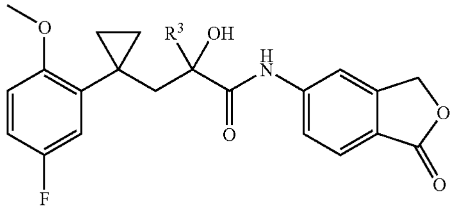

| No. | Racemic or Enantiomer | R3 |
|---|---|---|
| 661<br>662<br>663 | rac<br>+<br>− | 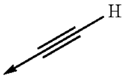 |
| 664<br>665<br>666 | rac<br>+<br>− | 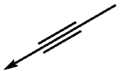 |
| 667<br>668<br>669 | rac<br>+<br>− | 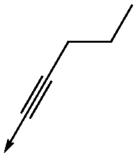 |

-continued
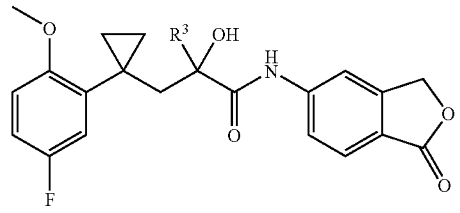
| No. | Racemic or Enantiomer | R3 |
|---|---|---|
| 670 | rac | 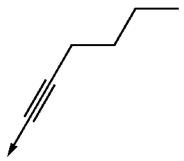 |
| 671 | + | |
| 672 | − | |
| 673 | rac | 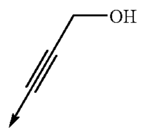 |
| 674 | + | |
| 675 | − | |
| 676 | rac | 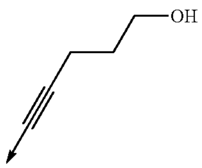 |
| 677 | + | |
| 678 | − | |
| 679 | rac | 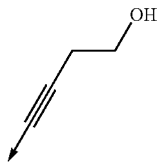 |
| 680 | + | |
| 681 | − | |
| 682 | rac | 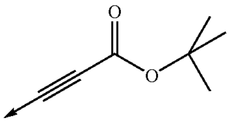 |
| 683 | + | |
| 684 | − | |
| 685 | rac | 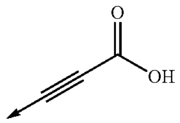 |
| 686 | + | |
| 687 | − | |
| 688 | rac | 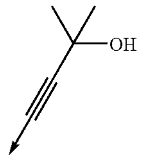 |
| 689 | + | |
| 690 | − | |
| 691 | rac | 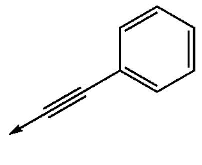 |
| 692 | + | |
| 693 | − | |
-continued
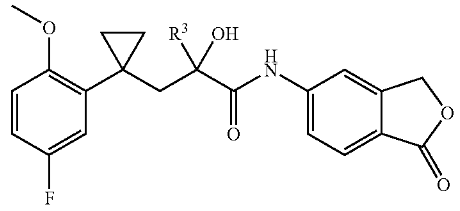
| No. | Racemic or Enantiomer | R3 |
|---|---|---|
| 694 | rac | 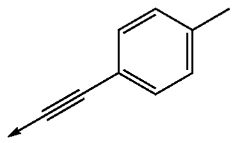 |
| 695 | + | |
| 696 | − | |
| 697 | rac | 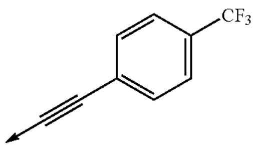 |
| 698 | + | |
| 699 | − | |
| 700 | rac | 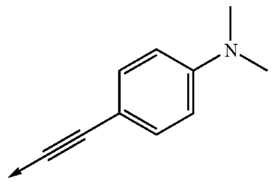 |
| 701 | + | |
| 702 | − | |
| 703 | rac | 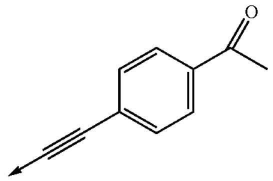 |
| 704 | + | |
| 705 | − | |
| 706 | rac | 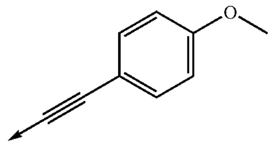 |
| 707 | + | |
| 708 | − | |
| 709 | rac | 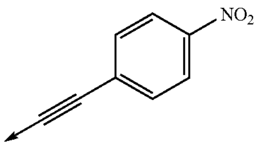 |
| 710 | + | |
| 711 | − | |
| 712 | rac | 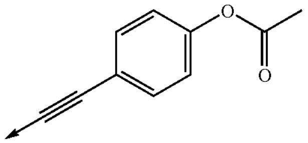 |
| 713 | + | |
| 714 | − | |
| 715 | rac | 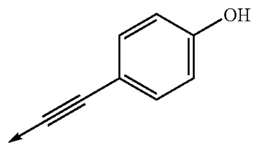 |
| 716 | + | |
| 717 | − | |

-continued
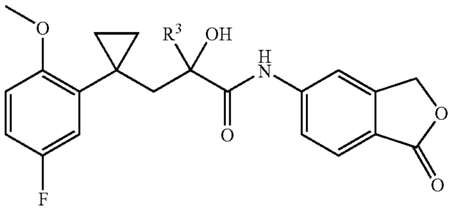
| No. | Racemic or Enantiomer | R3 |
|---|---|---|
| 718 | rac | 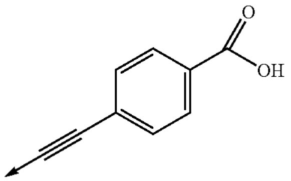 |
| 719 | + | |
| 720 | − | |
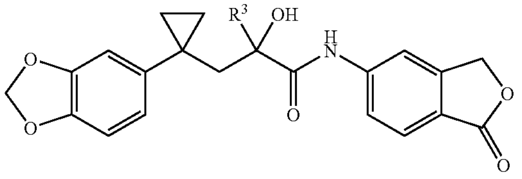
| No. | Racemic or Enantiomer | R3 |
|---|---|---|
| 721 | rac | 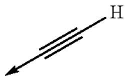 |
| 722 | + | |
| 723 | − | |
| 724 | rac | 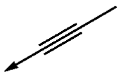 |
| 725 | + | |
| 726 | − | |
| 727 | rac | 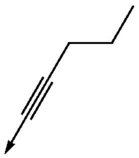 |
| 728 | + | |
| 729 | − | |
| 730 | rac | 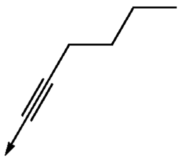 |
| 731 | + | |
| 732 | − | |
| 733 | rac | 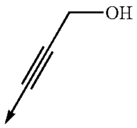 |
| 734 | + | |
| 735 | − | |
-continued
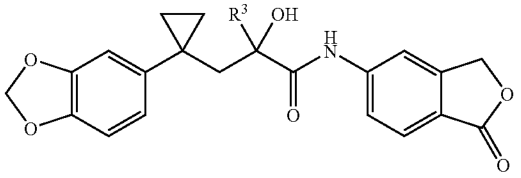
| No. | Racemic or Enantiomer | R3 |
|---|---|---|
| 736 | rac | 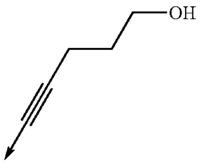 |
| 737 | + | |
| 738 | − | |
| 739 | rac | 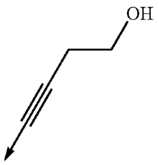 |
| 740 | + | |
| 741 | − | |
| 742 | rac | 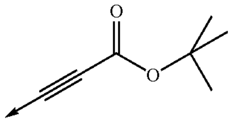 |
| 743 | + | |
| 744 | − | |
| 745 | rac | 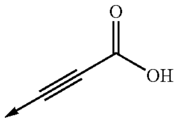 |
| 746 | + | |
| 747 | − | |
| 748 | rac | 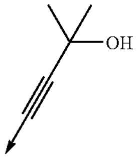 |
| 749 | + | |
| 750 | − | |
| 751 | rac | 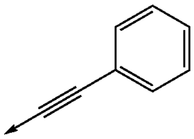 |
| 752 | + | |
| 753 | − | |
| 754 | rac | 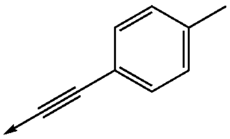 |
| 755 | + | |
| 756 | − | |
| 757 | rac | 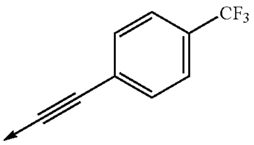 |
| 758 | + | |
| 759 | − | |

-continued
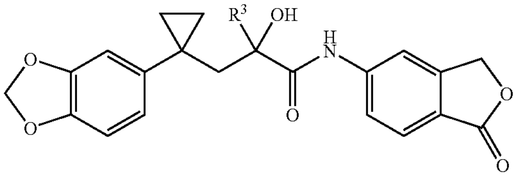
| No. | Racemic or Enantiomer | R3 |
|---|---|---|
| 760 | rac | 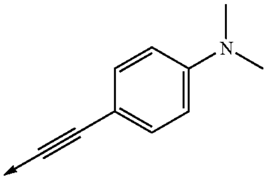 |
| 761 | + | |
| 762 | − | |
| 763 | rac | 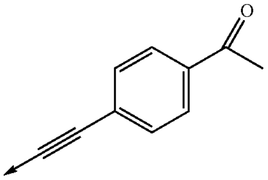 |
| 764 | + | |
| 765 | − | |
| 766 | rac | 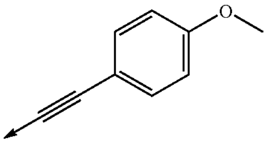 |
| 767 | + | |
| 768 | − | |
| 769 | rac | 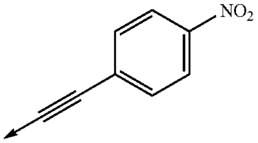 |
| 770 | + | |
| 771 | − | |
| 772 | rac | 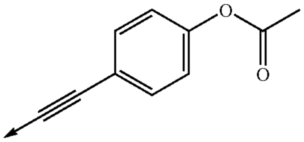 |
| 773 | + | |
| 774 | − | |
| 775 | rac | 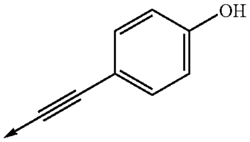 |
| 776 | + | |
| 777 | − | |
| 778 | rac | 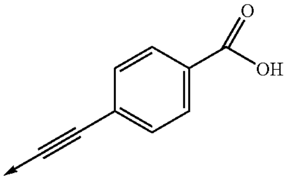 |
| 779 | + | |
| 780 | − | |
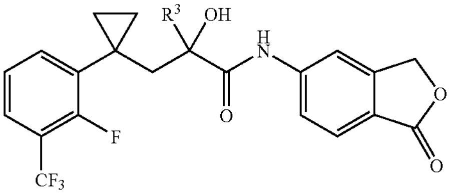
| No. | Racemic or Enantiomer | R3 |
|---|---|---|
| 781 | rac | 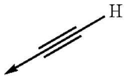 |
| 782 | + | |
| 783 | − | |
| 784 | rac | 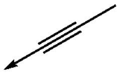 |
| 785 | + | |
| 786 | − | |
| 787 | rac | 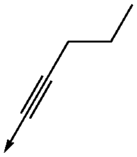 |
| 788 | + | |
| 789 | − | |
| 790 | rac | 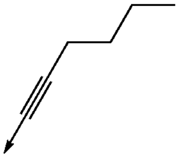 |
| 791 | + | |
| 792 | − | |
| 793 | rac | 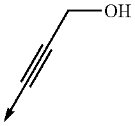 |
| 794 | + | |
| 795 | − | |
| 796 | rac | 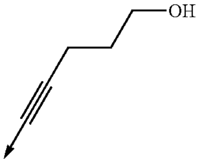 |
| 797 | + | |
| 798 | − | |
| 799 | rac | 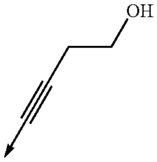 |
| 800 | + | |
| 801 | − | |
| 802 | rac | 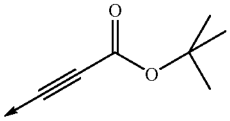 |
| 803 | + | |
| 804 | − | |
| 805 | rac | 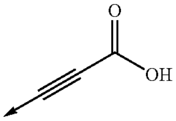 |
| 806 | + | |
| 807 | − | |

-continued
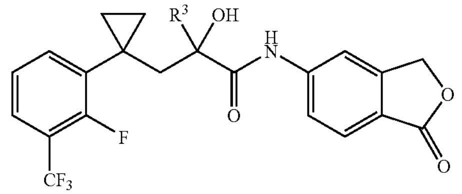
| No. | Racemic or Enantiomer | R3 |
|---|---|---|
| 808 | rac | 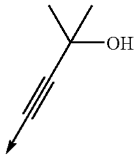 |
| 809 | + | |
| 810 | − | |
| 811 | rac | 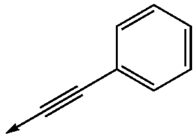 |
| 812 | + | |
| 813 | − | |
| 814 | rac | 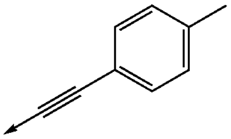 |
| 815 | + | |
| 816 | − | |
| 817 | rac | 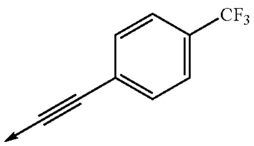 |
| 818 | + | |
| 819 | − | |
| 820 | rac | 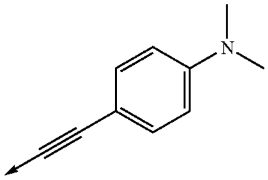 |
| 821 | + | |
| 822 | − | |
| 823 | rac | 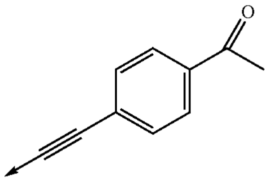 |
| 824 | + | |
| 825 | − | |
| 826 | rac | 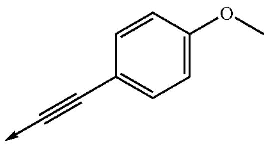 |
| 827 | + | |
| 828 | − | |
| 829 | rac | 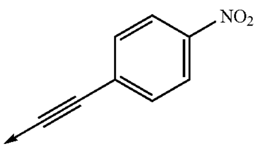 |
| 830 | + | |
| 831 | − | |
-continued
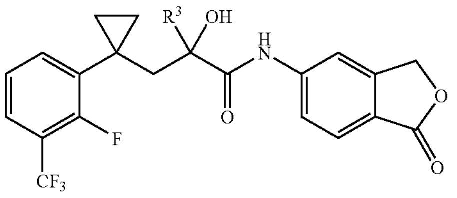
| No. | Racemic or Enantiomer | R3 |
|---|---|---|
| 832 | rac | 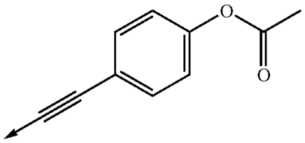 |
| 833 | + | |
| 834 | − | |
| 835 | rac | 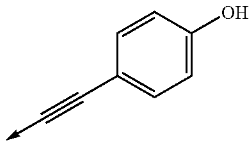 |
| 836 | + | |
| 837 | − | |
| 838 | rac | 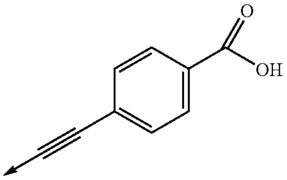 |
| 839 | + | |
| 840 | − | |
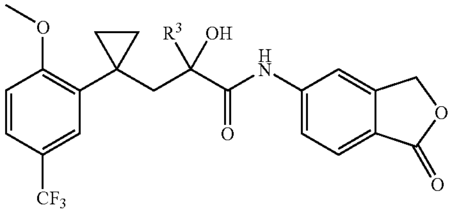
| No. | Racemic or Enantiomer | R3 |
|---|---|---|
| 841 | rac | 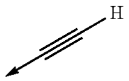 |
| 842 | + | |
| 843 | − | |
| 844 | rac | 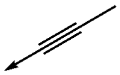 |
| 845 | + | |
| 846 | − | |
| 847 | rac | 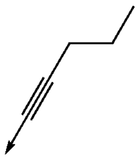 |
| 848 | + | |
| 849 | − | |

-continued
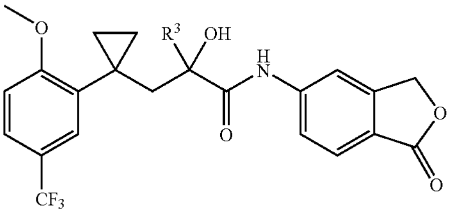
| No. | Racemic or Enantiomer | R3 |
|---|---|---|
| 850 | rac | 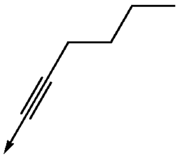 |
| 851 | + | |
| 852 | − | |
| 853 | rac | 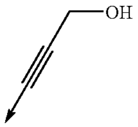 |
| 854 | + | |
| 855 | − | |
| 856 | rac | 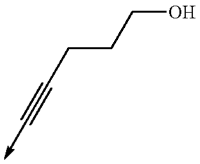 |
| 857 | + | |
| 858 | − | |
| 859 | rac | 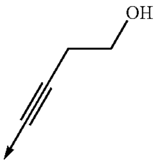 |
| 860 | + | |
| 861 | − | |
| 862 | rac | 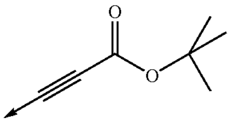 |
| 863 | + | |
| 864 | − | |
| 865 | rac | 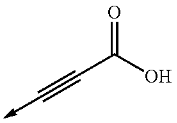 |
| 866 | + | |
| 867 | − | |
| 868 | rac | 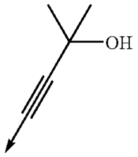 |
| 869 | + | |
| 870 | − | |
| 871 | rac | 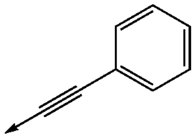 |
| 872 | + | |
| 873 | − | |
-continued
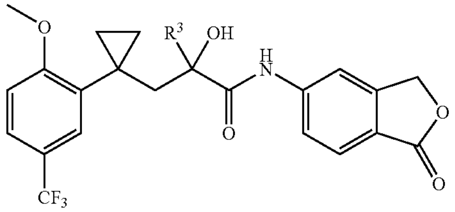
| No. | Racemic or Enantiomer | R3 |
|---|---|---|
| 874 | rac | 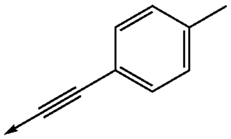 |
| 875 | + | |
| 876 | − | |
| 877 | rac | 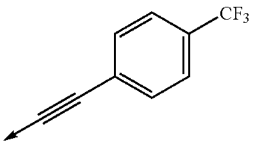 |
| 878 | + | |
| 879 | − | |
| 880 | rac | 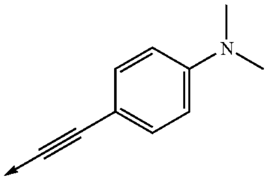 |
| 881 | + | |
| 882 | − | |
| 883 | rac | 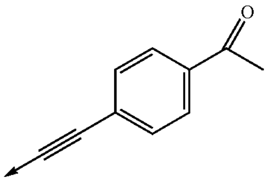 |
| 884 | + | |
| 885 | − | |
| 886 | rac | 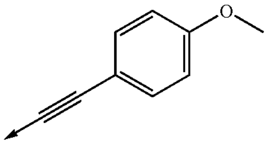 |
| 887 | + | |
| 888 | − | |
| 889 | rac | 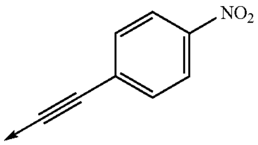 |
| 890 | + | |
| 891 | − | |
| 892 | rac | 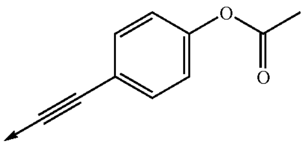 |
| 893 | + | |
| 894 | − | |
| 895 | rac | 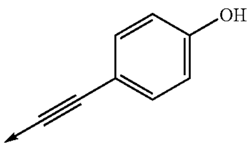 |
| 896 | + | |
| 897 | − | |

-continued
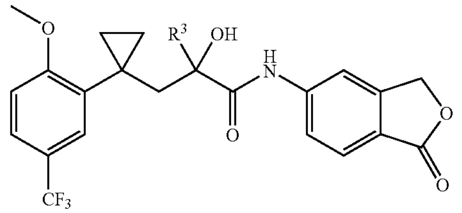
| No. | Racemic or Enantiomer | R3 |
|---|---|---|
| 898 | rac | 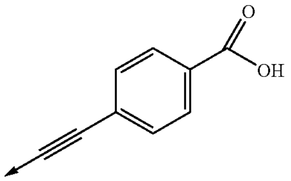 |
| 899 | + | |
| 900 | − | |
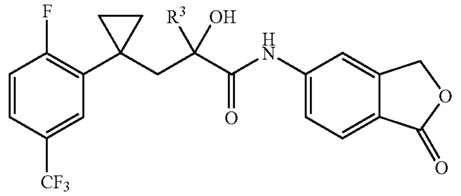
| No. | Racemic or Enantiomer | R3 |
|---|---|---|
| 901 | rac | 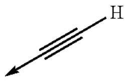 |
| 902 | + | |
| 903 | − | |
| 904 | rac | 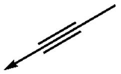 |
| 905 | + | |
| 906 | − | |
| 907 | rac | 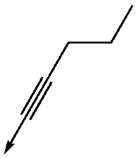 |
| 908 | + | |
| 909 | − | |
| 910 | rac | 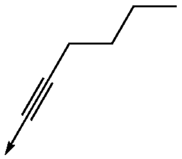 |
| 911 | + | |
| 912 | − | |
| 913 | rac | 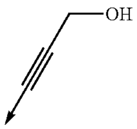 |
| 914 | + | |
| 915 | − | |
-continued
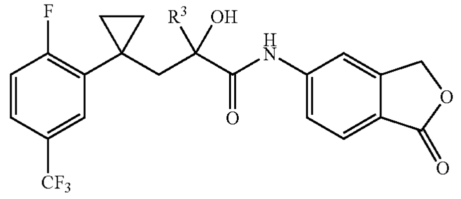
| No. | Racemic or Enantiomer | R3 |
|---|---|---|
| 916 | rac | 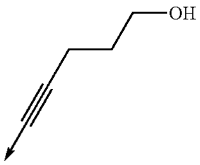 |
| 917 | + | |
| 918 | − | |
| 919 | rac | 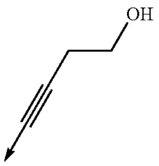 |
| 920 | + | |
| 921 | − | |
| 922 | rac | 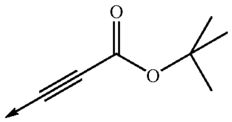 |
| 923 | + | |
| 924 | − | |
| 925 | rac | 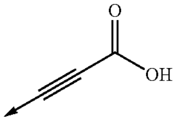 |
| 926 | + | |
| 927 | − | |
| 928 | rac | 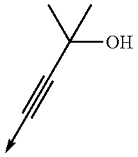 |
| 929 | + | |
| 930 | − | |
| 931 | rac | 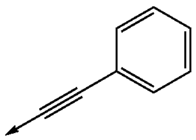 |
| 932 | + | |
| 933 | − | |
| 934 | rac | 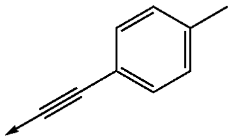 |
| 935 | + | |
| 936 | − | |
| 937 | rac | 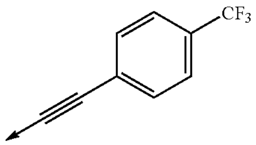 |
| 938 | + | |
| 939 | − | |

-continued

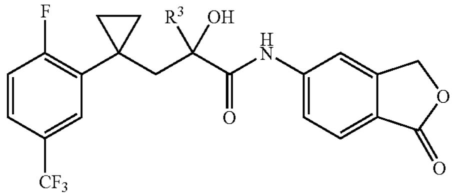

| No. | Racemic or Enantiomer | R3 |
|---|---|---|
| 940<br>941<br>942 | rac<br>+<br>− | 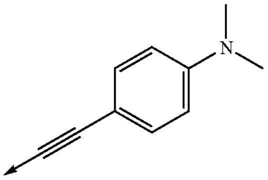 |
| 943<br>944<br>945 | rac<br>+<br>− | 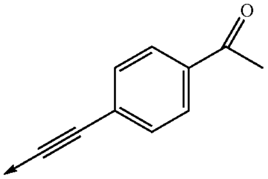 |
| 946<br>947<br>948 | rac<br>+<br>− | 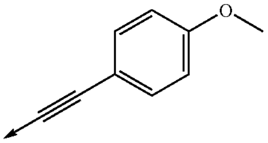 |
| 949<br>950<br>951 | rac<br>+<br>− | 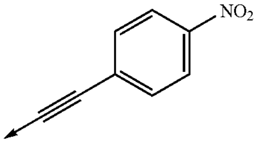 |
| 952<br>953<br>954 | rac<br>+<br>− | 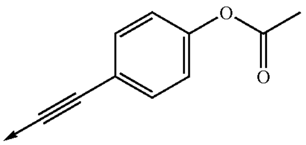 |
| 955<br>956<br>957 | rac<br>+<br>− | 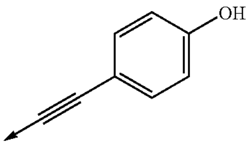 |
| 958<br>959<br>960 | rac<br>+<br>− | 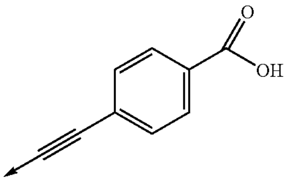 |

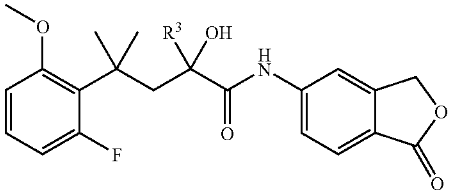

| No. | Racemic or Enantiomer | R3 |
|---|---|---|
| 961<br>962<br>963 | rac<br>+<br>− | 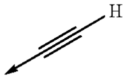 |
| 964<br>965<br>966 | rac<br>+<br>− | 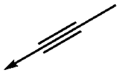 |
| 967<br>968<br>969 | rac<br>+<br>− | 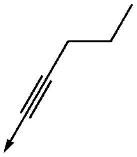 |
| 970<br>971<br>972 | rac<br>+<br>− | 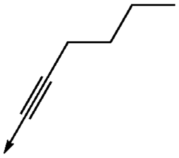 |
| 973<br>974<br>975 | rac<br>+<br>− | 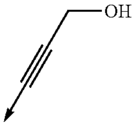 |
| 976<br>977<br>978 | rac<br>+<br>− | 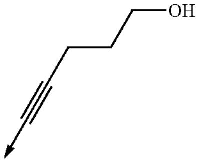 |
| 979<br>980<br>981 | rac<br>+<br>− | 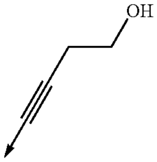 |
| 982<br>983<br>984 | rac<br>+<br>− | 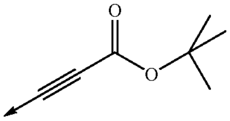 |
| 985<br>986<br>987 | rac<br>+<br>− | 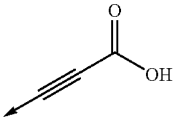 |

-continued
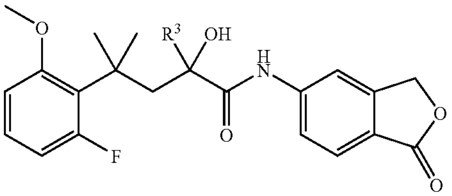
| No. | Racemic or Enantiomer | R3 |
| --- | --- | --- |
| 988 | rac | 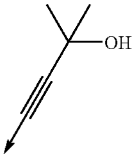 |
| 989 | + | |
| 990 | − | |
| 991 | rac | 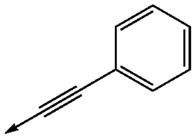 |
| 992 | + | |
| 993 | − | |
| 994 | rac | 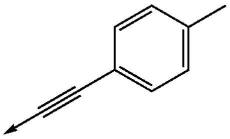 |
| 995 | + | |
| 996 | − | |
| 997 | rac | 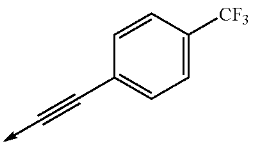 |
| 998 | + | |
| 999 | − | |
| 1000 | rac | 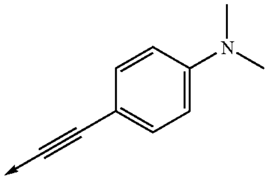 |
| 1001 | + | |
| 1002 | − | |
| 1003 | rac | 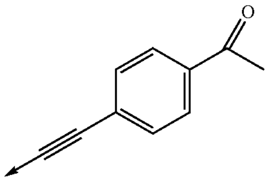 |
| 1004 | + | |
| 1005 | − | |
| 1006 | rac | 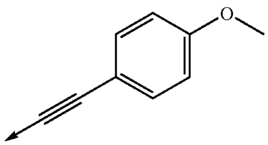 |
| 1007 | + | |
| 1008 | − | |
| 1009 | rac | 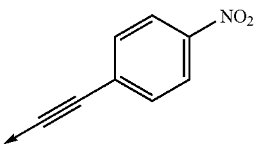 |
| 1010 | + | |
| 1011 | − | |
-continued
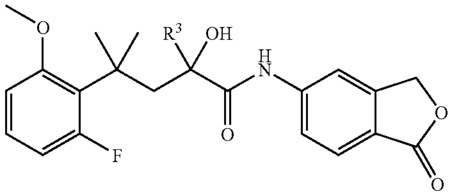
| No. | Racemic or Enantiomer | R3 |
| --- | --- | --- |
| 1012 | rac | 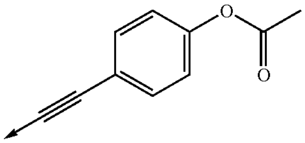 |
| 1013 | + | |
| 1014 | − | |
| 1015 | rac | 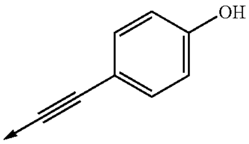 |
| 1016 | + | |
| 1017 | − | |
| 1018 | rac | 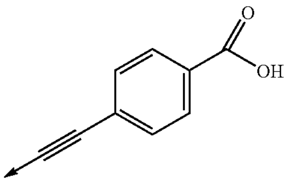 |
| 1019 | + | |
| 1020 | − | |
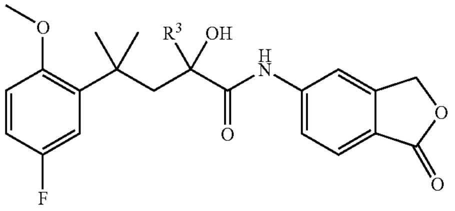
| No. | Racemic or Enantiomer | R3 |
| --- | --- | --- |
| 1021 | rac | 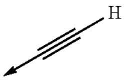 |
| 1022 | + | |
| 1023 | − | |
| 1024 | rac | 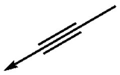 |
| 1025 | + | |
| 1026 | − | |
| 1027 | rac | 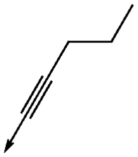 |
| 1028 | + | |
| 1029 | − | |

-continued
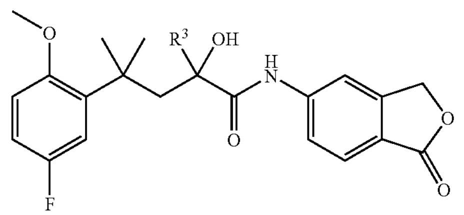
| No. | Racemic or Enantiomer | R3 |
|---|---|---|
| 1030 | rac | 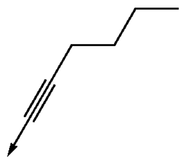 |
| 1031 | + | |
| 1032 | − | |
| 1033 | rac | 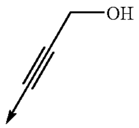 |
| 1034 | + | |
| 1035 | − | |
| 1036 | rac | 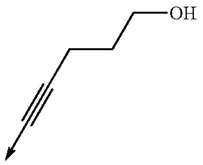 |
| 1037 | + | |
| 1038 | − | |
| 1039 | rac | 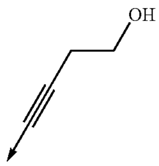 |
| 1040 | + | |
| 1041 | − | |
| 1042 | rac | 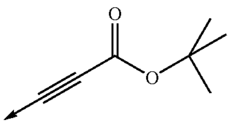 |
| 1043 | + | |
| 1044 | − | |
| 1045 | rac | 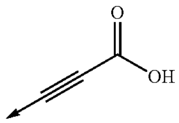 |
| 1046 | + | |
| 1047 | − | |
| 1048 | rac | 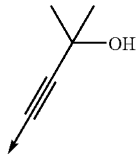 |
| 1049 | + | |
| 1050 | − | |
| 1051 | rac | 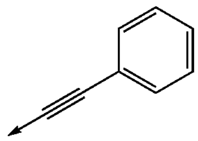 |
| 1052 | + | |
| 1053 | − | |
-continued
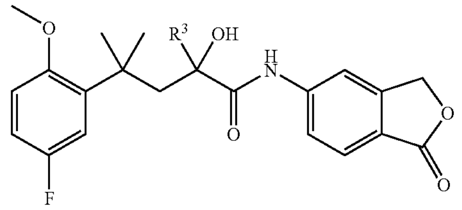
| No. | Racemic or Enantiomer | R3 |
|---|---|---|
| 1054 | rac | 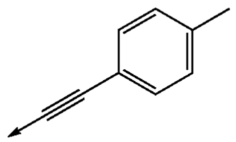 |
| 1055 | + | |
| 1056 | − | |
| 1057 | rac | 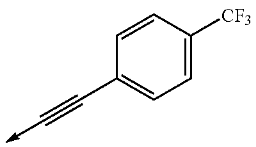 |
| 1058 | + | |
| 1059 | − | |
| 1060 | rac | 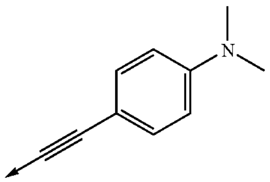 |
| 1061 | + | |
| 1062 | − | |
| 1063 | rac | 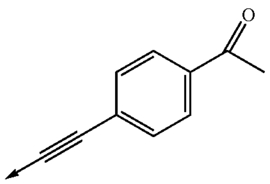 |
| 1064 | + | |
| 1065 | − | |
| 1066 | rac | 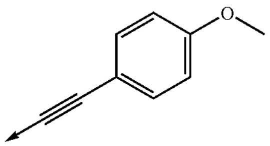 |
| 1067 | + | |
| 1068 | − | |
| 1069 | rac | 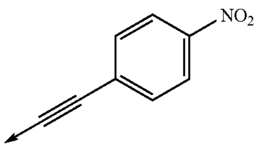 |
| 1070 | + | |
| 1071 | − | |
| 1072 | rac | 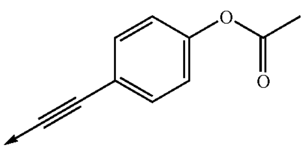 |
| 1073 | + | |
| 1074 | − | |
| 1075 | rac | 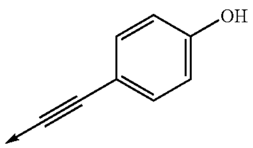 |
| 1076 | + | |
| 1077 | − | |

-continued

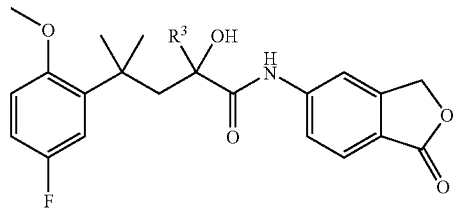

| No. | Racemic or Enantiomer | R3 |
|---|---|---|
| 1078<br>1079<br>1080 | rac<br>+<br>− | 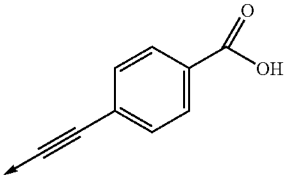 |

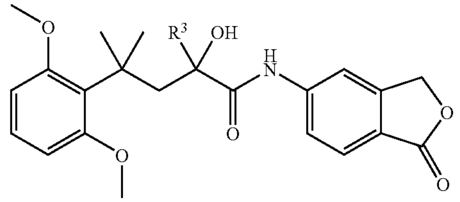

| No. | Racemic or Enantiomer | R3 |
|---|---|---|
| 1081<br>1082<br>1083 | rac<br>+<br>− | 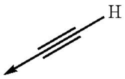 |
| 1084<br>1085<br>1086 | rac<br>+<br>− | 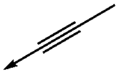 |
| 1087<br>1088<br>1089 | rac<br>+<br>− | 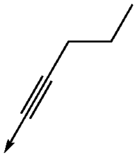 |
| 1090<br>1091<br>1092 | rac<br>+<br>− | 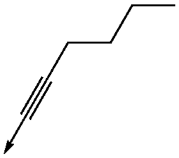 |
| 1093<br>1094<br>1095 | rac<br>+<br>− | 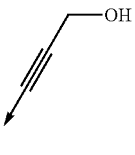 |

-continued

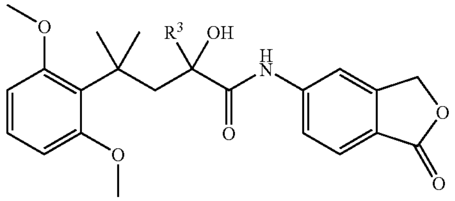

| No. | Racemic or Enantiomer | R3 |
|---|---|---|
| 1096<br>1097<br>1098 | rac<br>+<br>− | 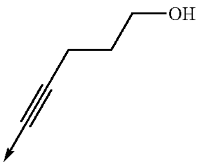 |
| 1099<br>1100<br>1101 | rac<br>+<br>− | 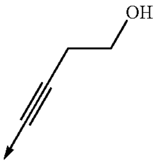 |
| 1102<br>1103<br>1104 | rac<br>+<br>− | 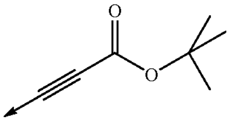 |
| 1105<br>1106<br>1107 | rac<br>+<br>− | 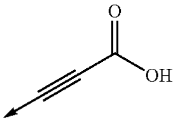 |
| 1108<br>1109<br>1110 | rac<br>+<br>− | 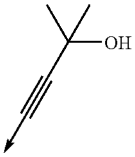 |
| 1111<br>1112<br>1113 | rac<br>+<br>− | 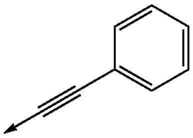 |
| 1114<br>1115<br>1116 | rac<br>+<br>− | 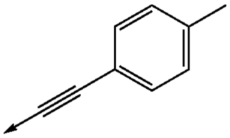 |
| 1117<br>1118<br>1119 | rac<br>+<br>− | 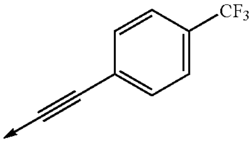 |

-continued
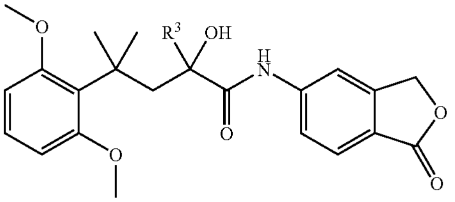
| No. | Racemic or Enantiomer | R3 |
|---|---|---|
| 1120 | rac | 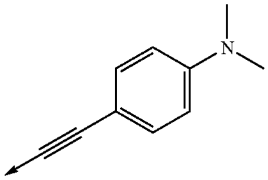 |
| 1121 | + | |
| 1122 | − | |
| 1123 | rac | 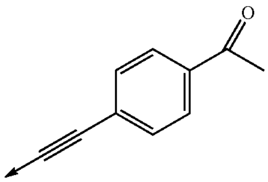 |
| 1124 | + | |
| 1125 | − | |
| 1126 | rac | 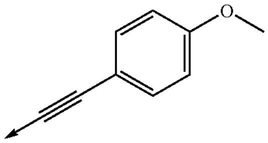 |
| 1127 | + | |
| 1128 | − | |
| 1129 | rac | 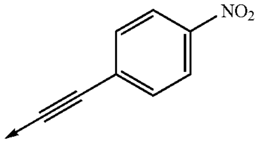 |
| 1130 | + | |
| 1131 | − | |
| 1132 | rac | 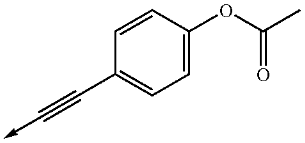 |
| 1133 | + | |
| 1134 | − | |
| 1135 | rac | 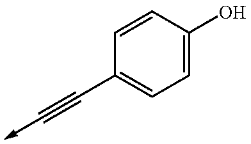 |
| 1136 | + | |
| 1137 | − | |
| 1138 | rac | 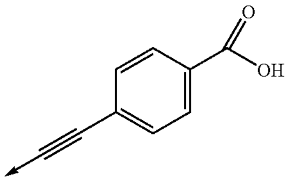 |
| 1139 | + | |
| 1140 | − | |
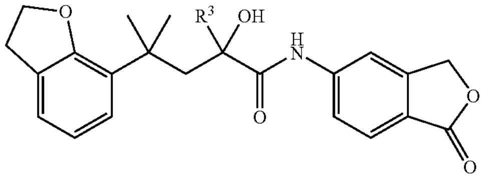
| No. | Racemic or Enantiomer | R3 |
|---|---|---|
| 1141 | rac | 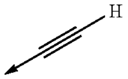 |
| 1142 | + | |
| 1143 | − | |
| 1144 | rac | 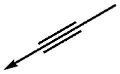 |
| 1145 | + | |
| 1146 | − | |
| 1147 | rac | 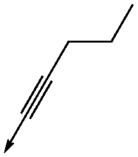 |
| 1148 | + | |
| 1149 | − | |
| 1150 | rac | 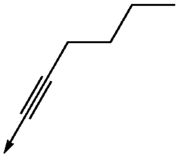 |
| 1151 | + | |
| 1152 | − | |
| 1153 | rac | 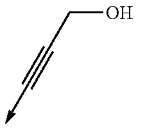 |
| 1154 | + | |
| 1155 | − | |
| 1156 | rac | 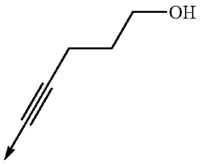 |
| 1157 | + | |
| 1158 | − | |
| 1159 | rac | 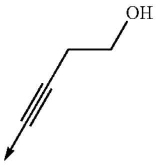 |
| 1160 | + | |
| 1161 | − | |
| 1162 | rac | 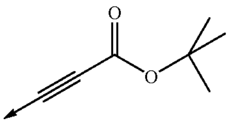 |
| 1163 | + | |
| 1164 | − | |
| 1165 | rac | 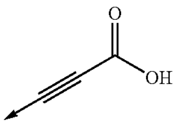 |
| 1166 | + | |
| 1167 | − | |

-continued
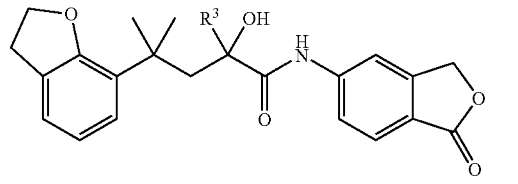
| No. | Racemic or Enantiomer | R3 |
|---|---|---|
| 1168 | rac | 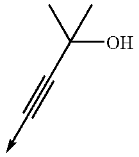 |
| 1169 | + | |
| 1170 | − | |
| 1171 | rac | 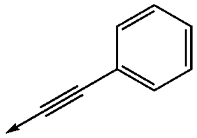 |
| 1172 | + | |
| 1173 | − | |
| 1174 | rac | 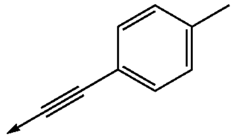 |
| 1175 | + | |
| 1176 | − | |
| 1177 | rac | 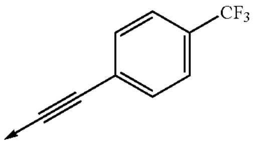 |
| 1178 | + | |
| 1179 | − | |
| 1180 | rac | 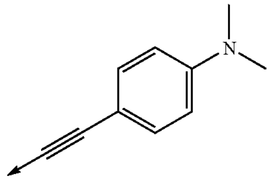 |
| 1181 | + | |
| 1182 | − | |
| 1183 | rac | 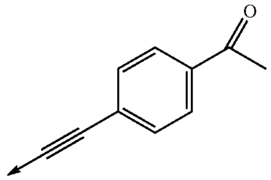 |
| 1184 | + | |
| 1185 | − | |
| 1186 | rac | 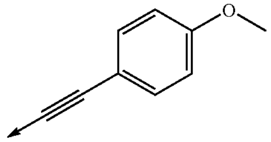 |
| 1187 | + | |
| 1188 | − | |
| 1189 | rac | 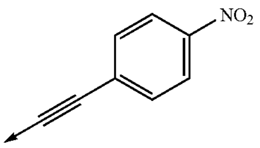 |
| 1190 | + | |
| 1191 | − | |
-continued
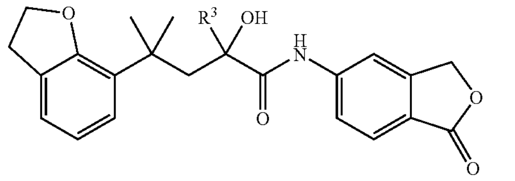
| No. | Racemic or Enantiomer | R3 |
|---|---|---|
| 1192 | rac | 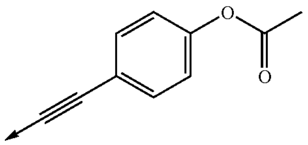 |
| 1193 | + | |
| 1194 | − | |
| 1195 | rac | 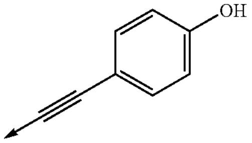 |
| 1196 | + | |
| 1197 | − | |
| 1198 | rac | 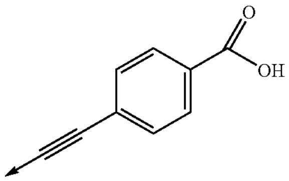 |
| 1199 | + | |
| 1200 | − | |
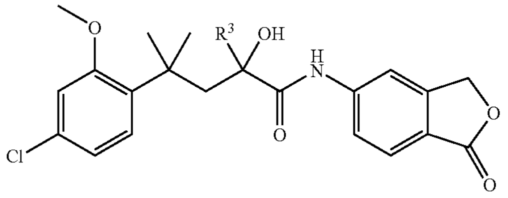
| No. | Racemic or Enantiomer | R3 |
|---|---|---|
| 1201 | rac | 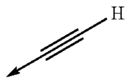 |
| 1202 | + | |
| 1203 | − | |
| 1204 | rac | 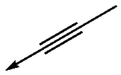 |
| 1205 | + | |
| 1206 | − | |
| 1207 | rac | 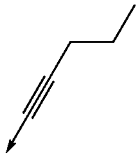 |
| 1208 | + | |
| 1209 | − | |

-continued
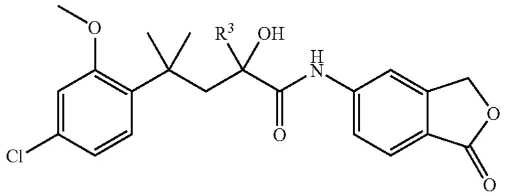
| No. | Racemic or Enantiomer | R3 |
|---|---|---|
| 1210 | rac | 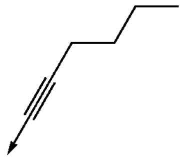 |
| 1211 | + | |
| 1212 | − | |
| 1213 | rac | 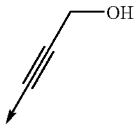 |
| 1214 | + | |
| 1215 | − | |
| 1216 | rac | 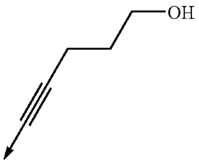 |
| 1217 | + | |
| 1218 | − | |
| 1219 | rac | 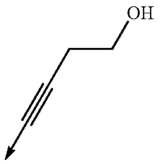 |
| 1220 | + | |
| 1221 | − | |
| 1222 | rac | 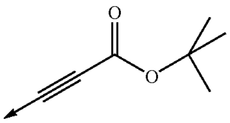 |
| 1223 | + | |
| 1224 | − | |
| 1225 | rac | 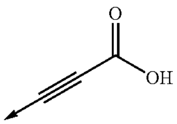 |
| 1226 | + | |
| 1227 | − | |
| 1228 | rac | 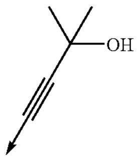 |
| 1229 | + | |
| 1230 | − | |
| 1231 | rac | 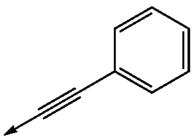 |
| 1232 | + | |
| 1233 | − | |
-continued
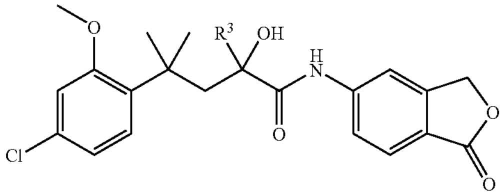
| No. | Racemic or Enantiomer | R3 |
|---|---|---|
| 1234 | rac | 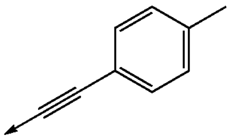 |
| 1235 | + | |
| 1236 | − | |
| 1237 | rac | 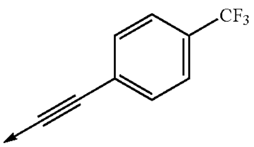 |
| 1238 | + | |
| 1239 | − | |
| 1240 | rac | 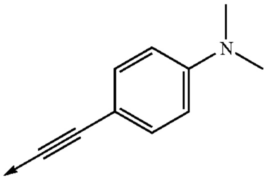 |
| 1241 | + | |
| 1242 | − | |
| 1243 | rac | 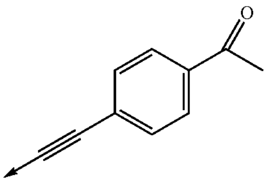 |
| 1244 | + | |
| 1245 | − | |
| 1246 | rac | 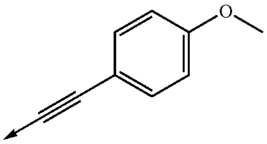 |
| 1247 | + | |
| 1248 | − | |
| 1249 | rac | 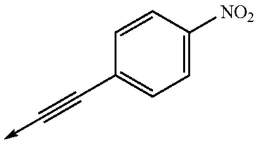 |
| 1250 | + | |
| 1251 | − | |
| 1252 | rac | 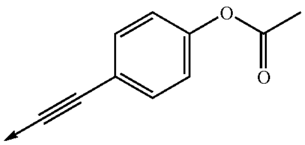 |
| 1253 | + | |
| 1254 | − | |
| 1255 | rac | 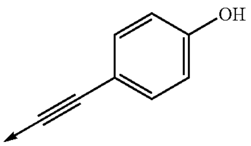 |
| 1256 | + | |
| 1257 | − | |

-continued
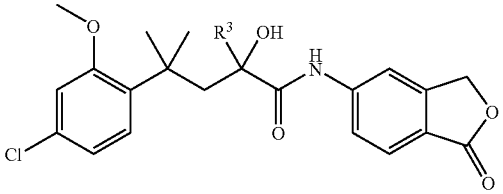
| No. | Racemic or Enantiomer | R3 |
|---|---|---|
| 1258 | rac | 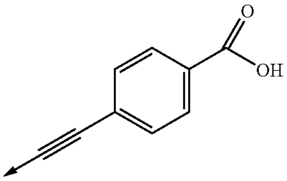 |
| 1259 | + | |
| 1260 | − | |
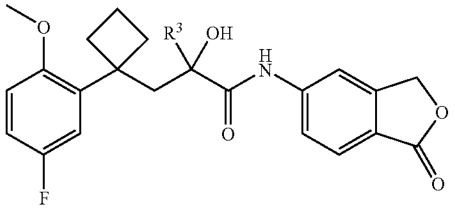
| No. | Racemic or Enantiomer | R3 |
|---|---|---|
| 1261 | rac | 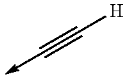 |
| 1262 | + | |
| 1263 | − | |
| 1264 | rac | 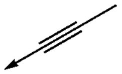 |
| 1265 | + | |
| 1266 | − | |
| 1267 | rac | 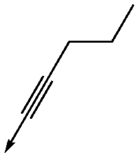 |
| 1268 | + | |
| 1269 | − | |
| 1270 | rac | 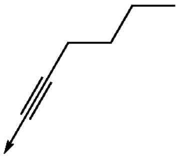 |
| 1271 | + | |
| 1272 | − | |
| 1273 | rac | 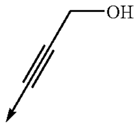 |
| 1274 | + | |
| 1275 | − | |
-continued
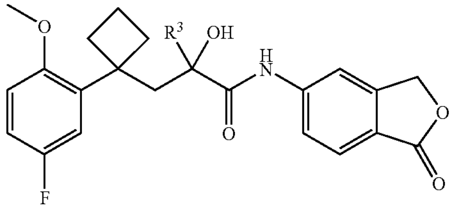
| No. | Racemic or Enantiomer | R3 |
|---|---|---|
| 1276 | rac | 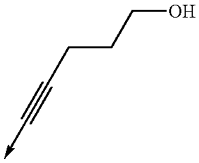 |
| 1277 | + | |
| 1278 | − | |
| 1279 | rac | 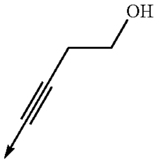 |
| 1280 | + | |
| 1281 | − | |
| 1282 | rac | 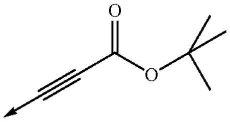 |
| 1283 | + | |
| 1284 | − | |
| 1285 | rac | 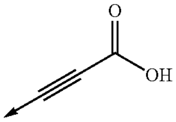 |
| 1286 | + | |
| 1287 | − | |
| 1288 | rac | 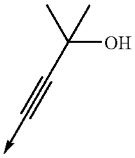 |
| 1289 | + | |
| 1290 | − | |
| 1291 | rac | 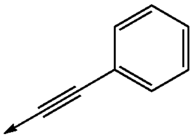 |
| 1292 | + | |
| 1293 | − | |
| 1294 | rac | 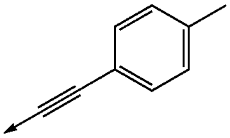 |
| 1295 | + | |
| 1296 | − | |
| 1297 | rac | 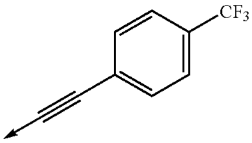 |
| 1298 | + | |
| 1299 | − | |

-continued
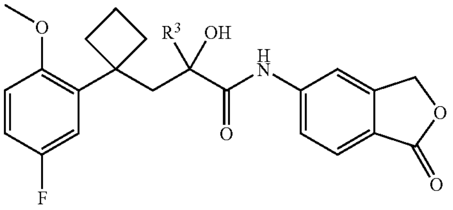
| No. | Racemic or Enantiomer | R3 |
|---|---|---|
| 1300 | rac | 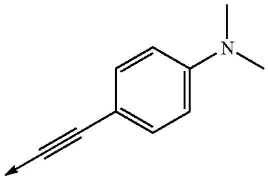 |
| 1301 | + | |
| 1302 | – | |
| 1303 | rac | 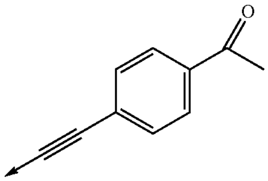 |
| 1304 | + | |
| 1305 | – | |
| 1306 | rac | 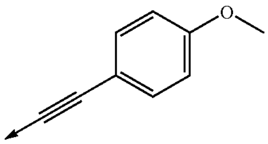 |
| 1307 | + | |
| 1308 | – | |
| 1309 | rac | 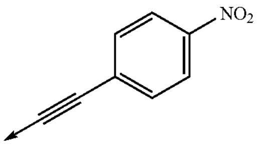 |
| 1310 | + | |
| 1311 | – | |
| 1312 | rac | 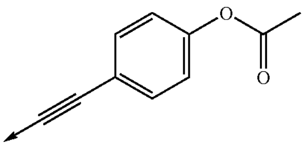 |
| 1313 | + | |
| 1314 | – | |
| 1315 | rac | 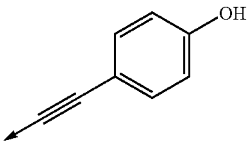 |
| 1316 | + | |
| 1317 | – | |
| 1318 | rac | 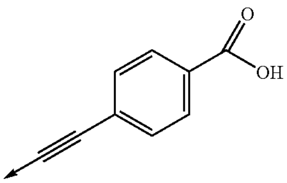 |
| 1319 | + | |
| 1320 | – | |
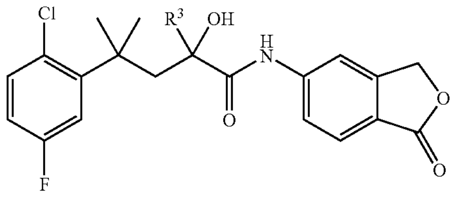
| No. | Racemic or Enantiomer | R3 |
|---|---|---|
| 1321 | rac | 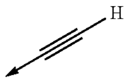 |
| 1322 | + | |
| 1323 | – | |
| 1324 | rac | 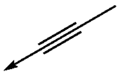 |
| 1325 | + | |
| 1326 | – | |
| 1327 | rac | 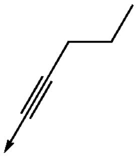 |
| 1328 | + | |
| 1329 | – | |
| 1330 | rac | 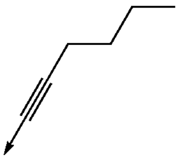 |
| 1331 | + | |
| 1332 | – | |
| 1333 | rac | 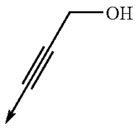 |
| 1334 | + | |
| 1335 | – | |
| 1336 | rac | 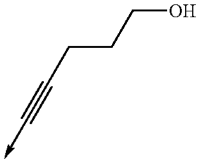 |
| 1337 | + | |
| 1338 | – | |
| 1339 | rac | 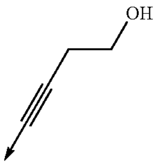 |
| 1340 | + | |
| 1341 | – | |
| 1342 | rac | 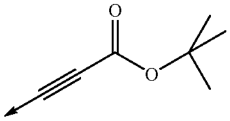 |
| 1343 | + | |
| 1344 | – | |
| 1345 | rac | 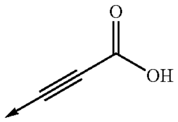 |
| 1346 | + | |
| 1347 | – | |

-continued
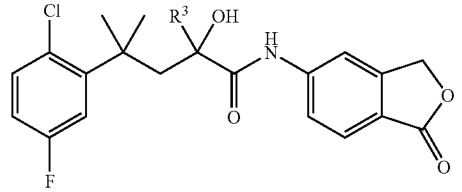
| No. | Racemic or Enantiomer | R3 |
|---|---|---|
| 1348 | rac | 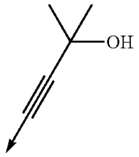 |
| 1349 | + | |
| 1350 | – | |
| 1351 | rac | 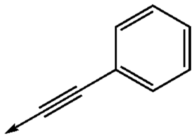 |
| 1352 | + | |
| 1353 | – | |
| 1354 | rac | 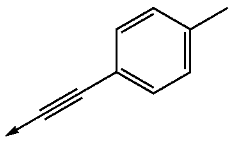 |
| 1355 | + | |
| 1356 | – | |
| 1357 | rac | 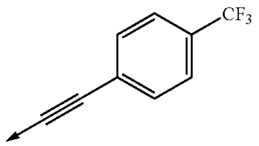 |
| 1358 | + | |
| 1359 | – | |
| 1360 | rac | 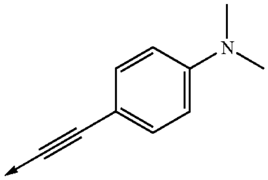 |
| 1361 | + | |
| 1362 | – | |
| 1363 | rac | 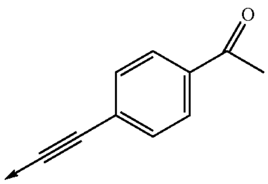 |
| 1364 | + | |
| 1365 | – | |
| 1366 | rac | 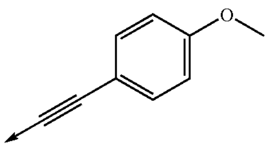 |
| 1367 | + | |
| 1368 | – | |
| 1369 | rac | 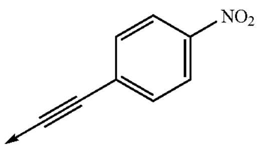 |
| 1370 | + | |
| 1371 | – | |
-continued
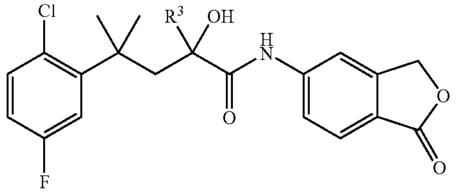
| No. | Racemic or Enantiomer | R3 |
|---|---|---|
| 1372 | rac | 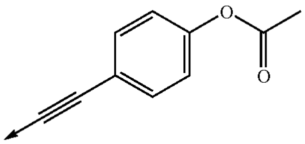 |
| 1373 | + | |
| 1374 | – | |
| 1375 | rac | 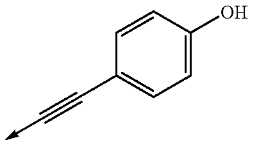 |
| 1376 | + | |
| 1377 | – | |
| 1378 | rac | 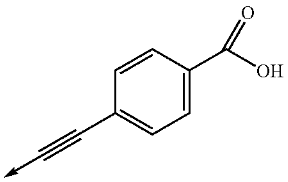 |
| 1379 | + | |
| 1380 | – | |
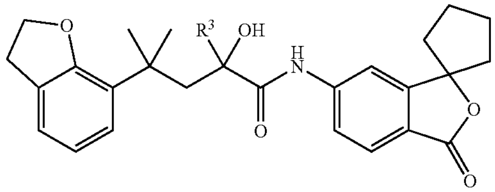
| No. | Racemic or Enantiomer | R3 |
|---|---|---|
| 1381 | rac | 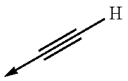 |
| 1382 | + | |
| 1383 | – | |
| 1384 | rac | 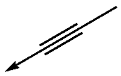 |
| 1385 | + | |
| 1386 | – | |
| 1387 | rac | 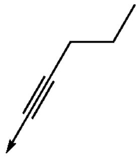 |
| 1388 | + | |
| 1389 | – | |

-continued
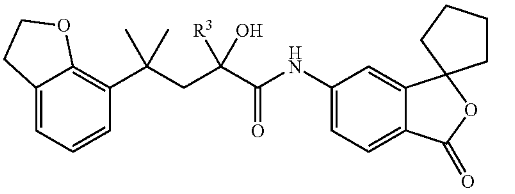
| No. | Racemic or Enantiomer | R3 |
|---|---|---|
| 1390 | rac | 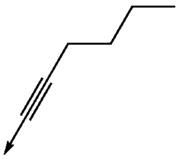 |
| 1391 | + | |
| 1392 | − | |
| 1393 | rac | 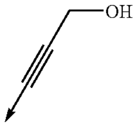 |
| 1394 | + | |
| 1395 | − | |
| 1396 | rac | 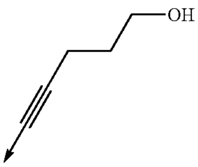 |
| 1397 | + | |
| 1398 | − | |
| 1399 | rac | 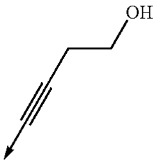 |
| 1400 | + | |
| 1401 | − | |
| 1402 | rac | 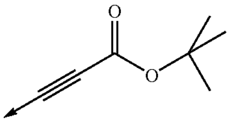 |
| 1403 | + | |
| 1404 | − | |
| 1405 | rac | 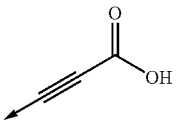 |
| 1406 | + | |
| 1407 | − | |
| 1408 | rac | 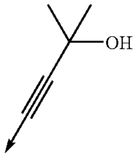 |
| 1409 | + | |
| 1410 | − | |
| 1411 | rac | 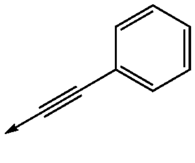 |
| 1412 | + | |
| 1413 | − | |
-continued
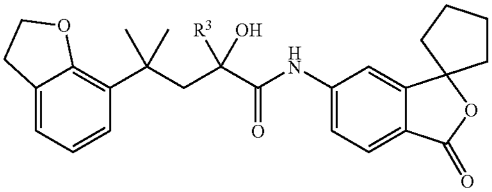
| No. | Racemic or Enantiomer | R3 |
|---|---|---|
| 1414 | rac | 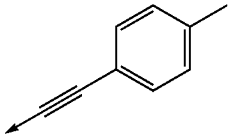 |
| 1415 | + | |
| 1416 | − | |
| 1417 | rac | 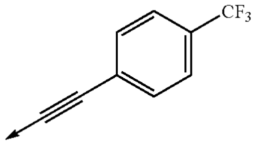 |
| 1418 | + | |
| 1419 | − | |
| 1420 | rac | 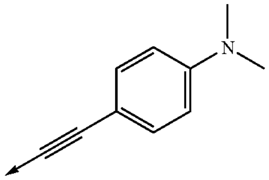 |
| 1421 | + | |
| 1422 | − | |
| 1423 | rac | 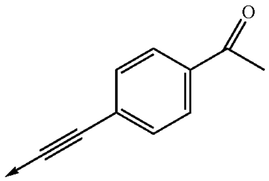 |
| 1424 | + | |
| 1425 | − | |
| 1426 | rac | 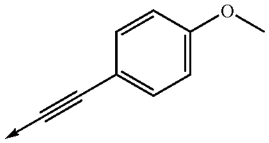 |
| 1427 | + | |
| 1428 | − | |
| 1429 | rac | 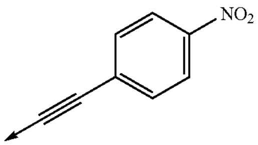 |
| 1430 | + | |
| 1431 | − | |
| 1432 | rac | 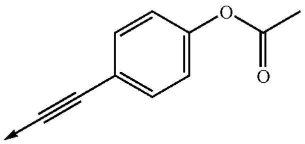 |
| 1433 | + | |
| 1434 | − | |
| 1435 | rac | 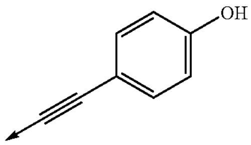 |
| 1436 | + | |
| 1437 | − | |

-continued

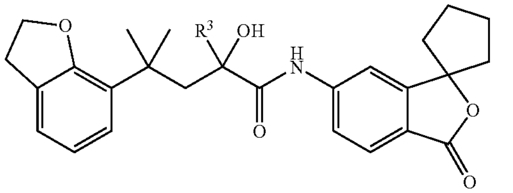

| No. | Racemic or Enantiomer | R3 |
| --- | --- | --- |
| 1438<br>1439<br>1440 | rac<br>+<br>− | 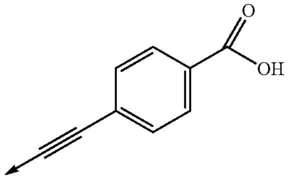 |

-continued

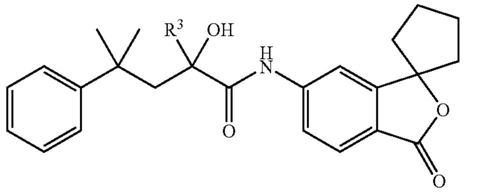

| No. | Racemic or Enantiomer | R3 |
| --- | --- | --- |
| 1441<br>1442<br>1443 | rac<br>+<br>− | 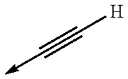 |
| 1444<br>1445<br>1446 | rac<br>+<br>− | 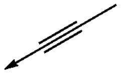 |
| 1447<br>1448<br>1449 | rac<br>+<br>− | 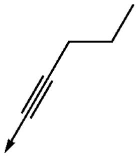 |
| 1450<br>1451<br>1452 | rac<br>+<br>− | 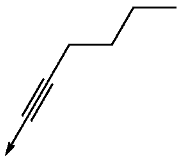 |
| 1453<br>1454<br>1455 | rac<br>+<br>− | 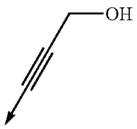 |

-continued

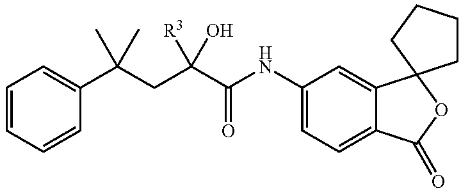

| No. | Racemic or Enantiomer | R3 |
| --- | --- | --- |
| 1456<br>1457<br>1458 | rac<br>+<br>− | 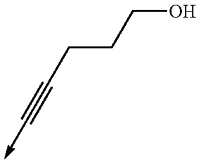 |
| 1459<br>1460<br>1461 | rac<br>+<br>− | 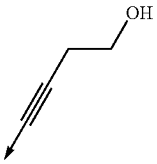 |
| 1462<br>1463<br>1464 | rac<br>+<br>− | 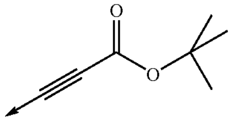 |
| 1465<br>1466<br>1467 | rac<br>+<br>− | 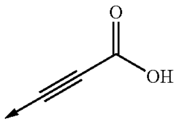 |
| 1468<br>1469<br>1470 | rac<br>+<br>− | 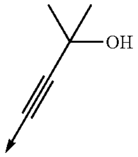 |
| 1471<br>1472<br>1473 | rac<br>+<br>− | 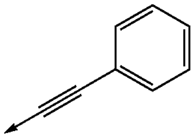 |
| 1474<br>1475<br>1476 | rac<br>+<br>− | 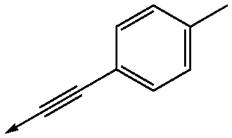 |
| 1477<br>1478<br>1479 | rac<br>+<br>− | 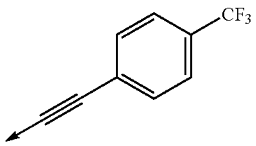 |

-continued
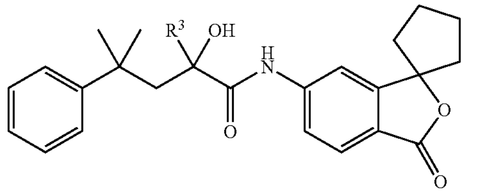
| No. | Racemic or Enantiomer | R3 |
|---|---|---|
| 1480 | rac | 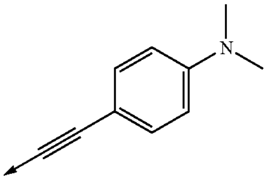 |
| 1481 | + | |
| 1482 | – | |
| 1483 | rac | 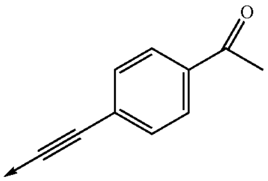 |
| 1484 | + | |
| 1485 | – | |
| 1486 | rac | 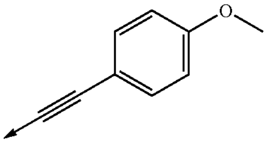 |
| 1487 | + | |
| 1488 | – | |
| 1489 | rac | 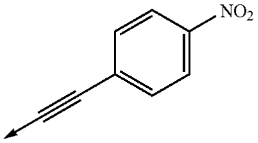 |
| 1490 | + | |
| 1491 | – | |
| 1492 | rac | 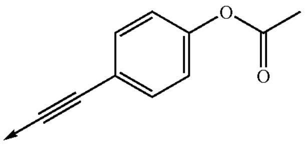 |
| 1493 | + | |
| 1494 | – | |
| 1495 | rac | 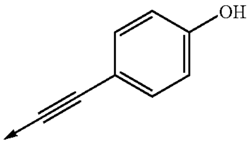 |
| 1496 | + | |
| 1497 | – | |
| 1498 | rac | 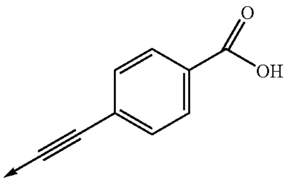 |
| 1499 | + | |
| 1500 | – | |
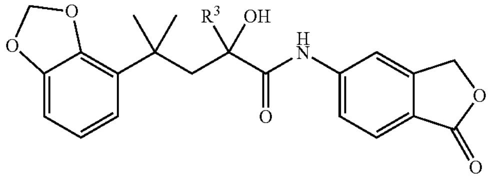
| No. | Racemic or Enantiomer | R3 |
|---|---|---|
| 1501 | rac | 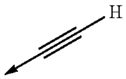 |
| 1502 | + | |
| 1503 | – | |
| 1504 | rac | 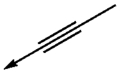 |
| 1505 | + | |
| 1506 | – | |
| 1507 | rac | 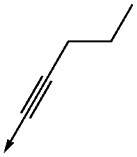 |
| 1508 | + | |
| 1509 | – | |
| 1510 | rac | 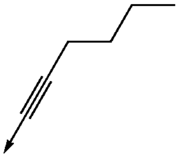 |
| 1511 | + | |
| 1512 | – | |
| 1513 | rac | 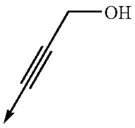 |
| 1514 | + | |
| 1515 | – | |
| 1516 | rac | 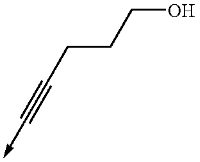 |
| 1517 | + | |
| 1518 | – | |
| 1519 | rac | 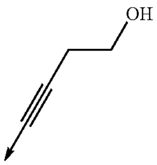 |
| 1520 | + | |
| 1521 | – | |
| 1522 | rac | 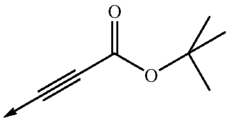 |
| 1523 | + | |
| 1524 | – | |
| 1525 | rac | 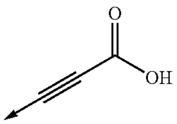 |
| 1526 | + | |
| 1527 | – | |

-continued
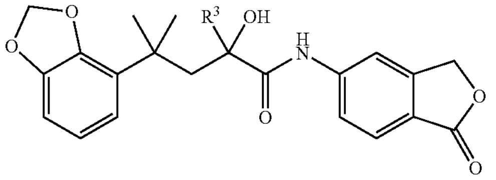
| No. | Racemic or Enantiomer | R3 |
|---|---|---|
| 1528 | rac | 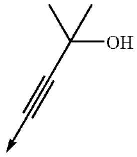 |
| 1529 | + | |
| 1530 | − | |
| 1531 | rac | 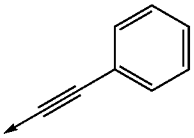 |
| 1532 | + | |
| 1533 | − | |
| 1534 | rac | 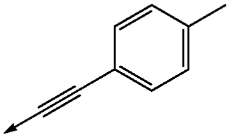 |
| 1535 | + | |
| 1536 | − | |
| 1537 | rac | 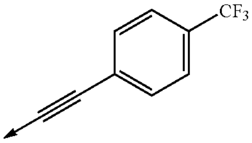 |
| 1538 | + | |
| 1539 | − | |
| 1540 | rac | 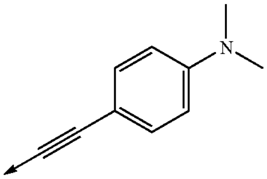 |
| 1541 | + | |
| 1542 | − | |
| 1543 | rac | 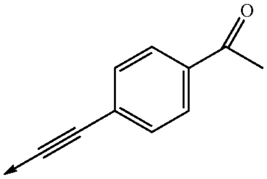 |
| 1544 | + | |
| 1545 | − | |
| 1546 | rac | 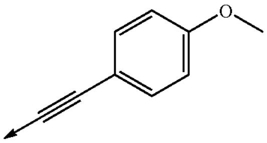 |
| 1547 | + | |
| 1548 | − | |
| 1549 | rac | 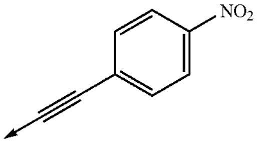 |
| 1550 | + | |
| 1551 | − | |
-continued
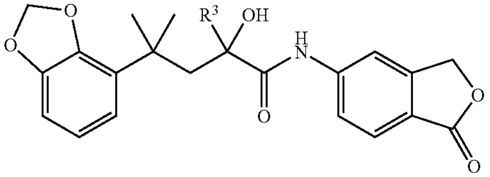
| No. | Racemic or Enantiomer | R3 |
|---|---|---|
| 1552 | rac | 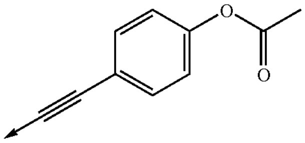 |
| 1553 | + | |
| 1554 | − | |
| 1555 | rac | 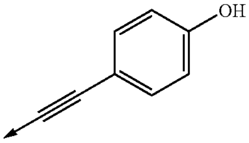 |
| 1556 | + | |
| 1557 | − | |
| 1558 | rac | 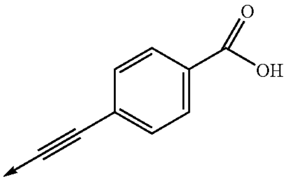 |
| 1559 | + | |
| 1560 | − | |
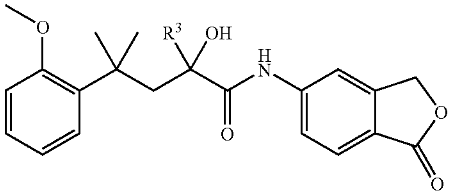
| No. | Racemic or Enantiomer | R3 |
|---|---|---|
| 1561 | rac | 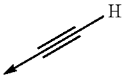 |
| 1562 | + | |
| 1563 | − | |
| 1564 | rac | 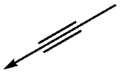 |
| 1565 | + | |
| 1566 | − | |
| 1567 | rac | 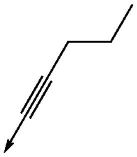 |
| 1568 | + | |
| 1569 | − | |
| 1570 | rac | 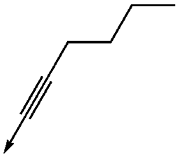 |
| 1571 | + | |
| 1572 | − | |

-continued
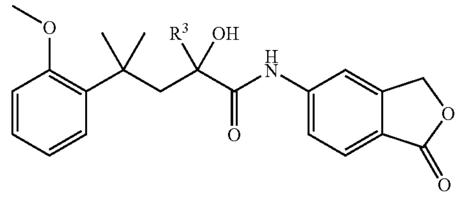
| No. | Racemic or Enantiomer | R3 |
|---|---|---|
| 1573 | rac | 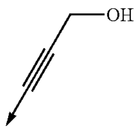 |
| 1574 | + | |
| 1575 | − | |
| 1576 | rac | 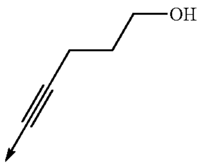 |
| 1577 | + | |
| 1578 | − | |
| 1579 | rac | 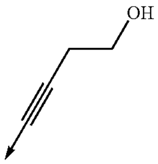 |
| 1580 | + | |
| 1581 | − | |
| 1582 | rac | 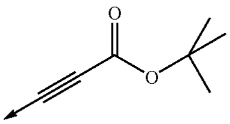 |
| 1583 | + | |
| 1584 | − | |
| 1585 | rac | 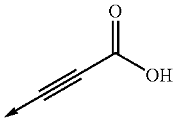 |
| 1586 | + | |
| 1587 | − | |
| 1588 | rac | 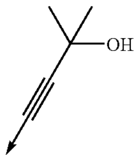 |
| 1589 | + | |
| 1590 | − | |
| 1591 | rac | 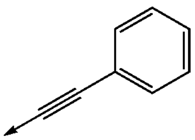 |
| 1592 | + | |
| 1593 | − | |
| 1594 | rac | 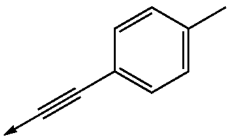 |
| 1595 | + | |
| 1596 | − | |
-continued
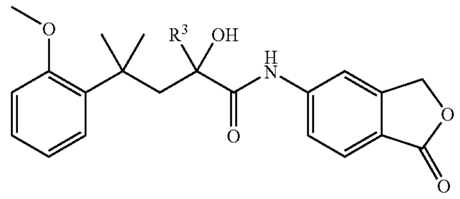
| No. | Racemic or Enantiomer | R3 |
|---|---|---|
| 1597 | rac | 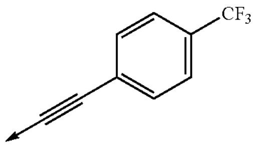 |
| 1598 | + | |
| 1599 | − | |
| 1600 | rac | 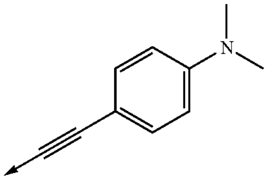 |
| 1601 | + | |
| 1602 | − | |
| 1603 | rac | 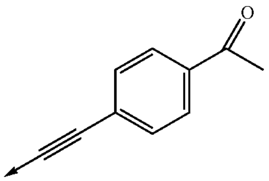 |
| 1604 | + | |
| 1605 | − | |
| 1606 | rac | 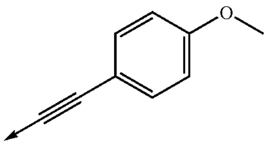 |
| 1607 | + | |
| 1608 | − | |
| 1609 | rac | 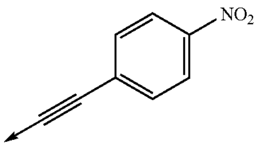 |
| 1610 | + | |
| 1611 | − | |
| 1612 | rac | 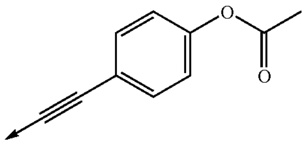 |
| 1613 | + | |
| 1614 | − | |
| 1615 | rac | 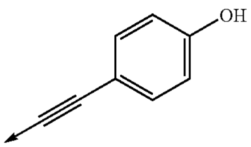 |
| 1616 | + | |
| 1617 | − | |

-continued

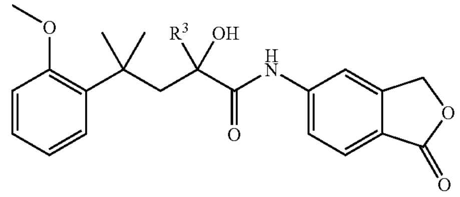

| No. | Racemic or Enantiomer | R3 |
|---|---|---|
| 1618 | rac | 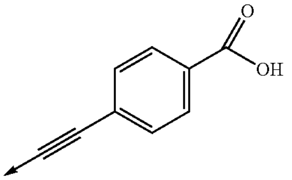 |
| 1619 | + | |
| 1620 | − | |

Biological Characterization of the Compounds According to the Invention

The identification of progesterone receptor modulators can be performed using simple methods, test programs that are known to one skilled in the art. To this end, for example, a compound that is to be tested can be incubated together with a gestagen in a test system for progesterone receptors, and it can be examined whether the progesterone-mediated action in this test system is altered in the presence of modulators.

The substances of general formula I according to the invention were tested in the following models:

Progesterone Receptor Binding Test

Measurement of the Receptor Binding Affinity:

The receptor binding affinity was determined by competitive binding of a specifically binding $^3$H-labeled hormone (tracer) and the compound to be tested on receptors in the cytosol from animal target organs. In this case, receptor saturation and reaction equilibrium were sought.

The tracers and increasing concentrations of the compound to be tested (competitor) were co-incubated with the receptor-containing cytosol fraction at 0-4° C. over 18 hours. After separation of the unbonded tracer with carbon-dextran suspension, the receptor-bonded tracer portion was measured for each concentration, and the $IC_{50}$ was determined from the concentration sequence. As a quotient of the $IC_{50}$ values of the reference substance and the compound to be tested (×100%), the relative molar binding affinity (RBA) was calculated (RBA of the reference substance=100%).

For the receptor types, the following incubation conditions were selected:

Progesterone Receptor:

Uterus cytosol of the estradiol-primed rabbit, homogenized in TED buffer (20 mmol of Tris/HCl, pH 7.4; 1 mmol of ethylenediamine tetraacetate, 2 mmol of dithiothreitol) with 250 mmol of saccharose; stored at −30° C. Tracer: $^3$H—ORG 2058, 5 nmol; reference substance: progesterone.

Glucocorticoid Receptor:

Thymus cytosol of the adrenalectomized rat, thymi stored at −30° C.; buffer: TED. Tracer: $^3$H-Dexamethasone, 20 nmol; reference substance: dexamethasone.

The relative receptor binding affinities (RBA values) of the compounds of general formula (I) according to the invention on the progesterone receptor are between 3 and 100% relative to the progesterone. On the glucocorticoid receptor, the RBA values are in the range of 3 to 30% relative to dexamethasone.

The compounds according to the invention accordingly have a high affinity to the progesterone receptor but only a low affinity to the glucocorticoid receptor.

Antagonism of Progesterone Receptor PR-B

The transactivation assay is performed as described in WO 02/054064.

Agonism of Progesterone Receptor PR-B

The transactivation assay is performed as described in Fuhrmann et al. (Fuhrmann, U.; Hess-Stump, H.; Cleve, A.; Neef, G.; Schwede, W.; Hoffmann, J.; Fritzemeier, K.-H., Chwalisz, K.; Journal of Medicinal Chem., 43, 26, 2000, 5010-5016).

| | Antagonistic activity | | Agonistic activity | |
|---|---|---|---|---|
| No. | $IC_{50}$ [nM] | Efficacy [%] | $EC_{50}$ [nM] | Efficacy [%] |
| 9 | 3 | 96 | n.b. | 3 |
| 13 | 3 | 92 | n.b. | 7 |
| 3b | 0.4 | 97 | n.b. | 2 |
| 7 | 4 | 82 | 2 | 11 |

Dosage

For use according to the invention, the progesterone receptor modulators can be administered orally, enterally, parenterally or transdermally.

In general, satisfactory results can be expected in the treatment of the above-mentioned indications if the daily doses encompass a range of 1 μg to 500 mg of the compound according to the invention.

Suitable dosages of the compounds according to the invention in humans for the treatment of endometriosis, leiomyomas of the uterus and dysfunctional bleeding as well as for use in birth control as well as for hormone replacement therapy are 50 μg to 500 mg per day, depending on age and constitution of the patient, whereby the necessary daily dose can be administered one or more times.

For treatment of breast cancer, the dosage range for the compounds according to the invention comprises 10 mg to 1000 mg daily.

The formulation of the pharmaceutical preparations based on the new compounds is carried out in a way that is known in the art, by the active ingredient being processed with the vehicles, fillers, substances that influence decomposition, binding agents, moisturizers, lubricants, absorbents, diluents, flavoring correctives, dyes, etc., that are commonly used in galenicals and being converted into the desired form of administration. In this case, reference is made to Remington's Pharmaceutical Science, 15$^{th}$ Ed. Mack Publishing Company, East Pennsylvania (1980).

For oral administration, in particular tablets, film tablets, coated tablets, capsules, pills, powders, granulates, lozenges, suspensions, emulsions or solutions are suitable.

For parenteral administration, injection and infusion preparations are possible.

For intraarticulate injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic therapy and for local therapy.

In addition, agents for vaginal application can also be mentioned as preparations.

For pulmonary administration of the new compounds, the latter can be used in the form of aerosols and inhalants.

For transdermal administration, patches are possible, or for topical application, formulations in gels, ointments, fatty ointments, creams, pastes, powders, milk and tinctures are possible. The dosage of the compounds of general formula I should be 0.01%-20% in these preparations to achieve an adequate pharmacological action.

Corresponding tablets can be obtained by, for example, mixing active ingredient with known adjuvants, for example inert diluents such as dextrose, sugar, sorbitol, mannitol, polyvinylpyrrolidone, explosives such as corn starch or alginic acid, binders such as starch or gelatin, lubricants such as magnesium stearate or talc and/or agents for achieving a depot effect such as carboxylpolymethylene, carboxylmethyl cellulose, cellulose acetate phthalate or polyvinyl acetate. The tablets can also consist of several layers.

Accordingly, coated tablets can be produced by coating cores, produced analogously to the tablets, with agents that are commonly used in tablet coatings, for example polyvinylpyrrolidone or shellac, gum arabic, talc, titanium oxide or sugar. In this case, the coated tablet shell can also consist of several layers, whereby the adjuvants that are mentioned above in the tablets can be used.

Solutions or suspensions of the compounds of general formula I according to the invention can contain additional taste-improving agents such as saccharine, cyclamate or sugar, as well as, e.g., flavoring substances, such as vanilla or orange extract. In addition, they can contain suspending adjuvants such as sodium carboxy methyl cellulose or preservatives such as p-hydroxybenzoates.

The capsules that contain compounds of general formula I can be produced by, for example, the compound(s) of general formula I being mixed with an inert vehicle such as lactose or sorbitol and encapsulated in gelatin capsules.

Suitable suppositories can be produced by, for example, mixing with vehicles that are provided for this purpose, such as neutral fats or polyethylene glycol, or derivatives thereof.

The compounds of general formula (I) according to the invention or their pharmaceutically acceptable salts can be used based on their antagonistic or partial agonistic action for the production of a pharmaceutical agent, in particular for treatment and prophylaxis of gynecological diseases, such as endometriosis, leiomyomas of the uterus, dysfunctional bleeding and dysmenorrhea. In addition, they can be used to counteract hormonal irregularities, to trigger menstruation and alone or in combination with prostaglandins and/or oxytocin to induce birth.

In addition, the compounds of general formula (I) according to the invention or their pharmaceutically acceptable salts are suitable for the production of preparations for contraception for women (see also WO 93/23020, WO 93/21927).

In addition, the compounds according to the invention or their pharmaceutically acceptable salts can be used alone or in combination with a Selective Estrogen Receptor Modulator (SERM) for female hormone replacement therapy.

In addition, the above-mentioned compounds exert an antiproliferative action in hormone-dependent tumors. They are therefore suitable for the therapy of hormone-dependent carcinomas, such as, for example, for breast, prostate or endometrial carcinomas.

The compounds according to the invention or their pharmaceutically acceptable salts can be used for the treatment of hormone-dependent carcinomas, both in first-line therapy and in second-line therapy, in particular after tamoxifen failure.

The compounds of general formula (I) according to the invention that have an antagonistic or partial agonistic action or their pharmaceutically acceptable salts can also be used in combination with compounds that have an antiestrogenic action (estrogen receptor antagonists or aromatase inhibitors) or Selective Estrogen Receptor Modulators (SERM) for the production of pharmaceutical preparations for treating hormone-dependent tumors. For the treatment of endometriosis or leiomyomas of the uterus, the compounds according to the invention can also be used in combination with SERMs or an antiestrogen (estrogen receptor antagonists or aromatase inhibitors). In the treatment of hormone-dependent tumors, the progesterone receptor modulator and the antiestrogen (estrogen receptor antagonists or aromatase inhibitors) or the SERM can be provided for simultaneous or else for sequential administration. In sequential administration, preferably first the antiestrogen (estrogen receptor antagonists or aromatase inhibitor) or SERM is administered, and then the progesterone receptor modulator is administered.

In this case, in the combination with the nonsteroidal progesterone receptor modulators according to the invention, for example, the following antiestrogens (estrogen receptor antagonists or aromatase inhibitors) or SERMs are considered:

tamoxifen, 5-(4-{5-[(RS)-(4,4,5,5,5-pentafluoropentyl)sulfinyl]-pentyloxy}phenyl)-6-phenyl-8,9-dihydro-7H-benzocyclohepten-2-ol (WO 00/03979), ICI 182 780 (7alpha-[9-(4,4,5,5-pentafluoropentylsulfinyl)nonyl]estra-1,3,5(10)-triene-3,17-beta-diol), 11beta-fluoro-7alpha-[5-(methyl {3-[(4,4,5,5,5-pentafluoropentyl)sulfanyl]propyl}amino) pentyl]estra-1,3,5(10)-triene-3,17beta-diol (WO98/07740), 11beta-fluoro-7alpha-{5-[methyl(7,7,8,8,9,9,10,10,10-nonafluorodecyl)amino]pentyl}estra-1,3,5(10)-triene-3,17beta-diol (WO 99/33855), 11 beta-fluoro-17alpha-methyl-7alpha-{5-[methyl(8,8,9,9,9-pentafluorononyl)-amino] pentyl}estra-1,3,5(10)-triene-3,17beta-diol (WO 03/045972), clomifene, raloxifene as well as other antiestrogenically active compounds, and aromatase inhibitors, such as, for example, fadrozole, formestane, letrozole, anastrozole or atamestane.

Finally, this invention also relates to the use of the compounds of general formula I, optionally together with an antiestrogen or SERM, for the production of a pharmaceutical agent.

This invention also relates to pharmaceutical compositions that contain at least one compound according to the invention, optionally in the form of a pharmaceutically/pharmacologically compatible salt, without or together with pharmaceutically compatible adjuvants and/or vehicles.

These pharmaceutical compositions and pharmaceutical agents can be provided for oral, rectal, vaginal, subcutaneous, percutaneous, intravenous or intramuscular administration. In addition to commonly used vehicles and/or diluents, they contain at least one compound according to the invention.

The pharmaceutical agents of the invention are produced in a known way with the commonly used solid or liquid vehicles or diluents and the usually used pharmaceutical-technical adjuvants corresponding to the desired type of administration with a suitable dosage. The preferred preparations exist in a dispensing form that is suitable for oral administration. Such dispensing forms are, for example, tablets, film tablets, coated tablets, capsules, pills, powders, solutions or suspensions or else depot forms.

The pharmaceutical compositions that contain at least one of the compounds according to the invention are preferably administered orally.

Parenteral preparations, such as injection solutions, are also considered.

In addition, for example, suppositories and agents for vaginal application can also be mentioned as preparations.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The following examples are used for a more detailed explanation of the subject of the invention, without intending that it be limited to these examples.

The production of the starting compound 5-{3-[1-(2-fluoro-5-trifluoromethylphenyl)-cyclopropyl]-2-oxopropionylamino}phthalide is described in Patent WO 200375915, and the production of 5-{3-[1-phenyl-cyclopropyl]-2-oxopropionylamino}phthalide is described in WO 9854159.

rac-5-{2-Ethinyl-2-hydroxy-3-[1-(2-fluoro-5-trifluoromethylphenyl)-cyclopropyl]-propionylamino}phthalide 1

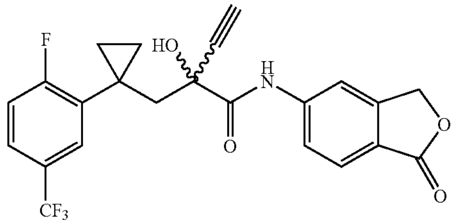

Ethinyl magnesium bromide (6 ml, 0.5 M in tetrahydrofuran) was added to an ice-cold solution that consists of 5-{3-[1-(2-fluoro-5-trifluoromethylphenyl)-cyclopropyl]-2-oxopropionylamino}phthalide (632 mg) in THF (4 ml). The reaction solution under argon was allowed to come to room temperature within 3 hours. Then, the reaction mixture was poured into ice-cold, saturated ammonium chloride solution. It was extracted with ethyl acetate. The combined organic phases were washed with saturated sodium chloride solution and dried on sodium sulfate. The crude product that is obtained was chromatographed on silica gel. 2.2 g of product was obtained.

$^{1}$H-NMR (ppm, $CDCl_3$, 400 MHz): 0.83 (1H), 0.92-1.10 (2H), 2.37 (1H), 2.56 (1H), 2.59 (1H), 3.10 (1H), 5.28 (2H), 7.02 (1H), 7.31 (1H), 7.37 (1H), 7.58 (1H), 7.86 (1H), 7.94 (1H), 8.70 (1H).

rac-5-{2-Hydroxy-3-[1-(2-fluoro-5-trifluoromethylphenyl)-cyclopropyl]-2-propinyl-propionylamino}phthalide 2

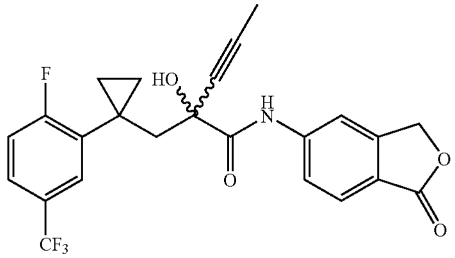

Analogously to Example 1, 145 mg of product was obtained from 1-propinylmagnesium bromide (2 ml of 0.5 M solution in tetrahydrofuran) and 210 mg of 6-[4-(2-chloro-4-fluorophenyl)-4-methyl-2-oxovaleroylamino]-4-methyl-2,3-benzoxazin-1-one.

$^{1}$H-NMR (ppm, $CDCl_3$, 400 MHz): 0.86 (1H), 0.90-1.05 (3H), 1.72 (3H), 2.35 (1H), 2.49 (1H), 2.96 (1H), 5.27 (2H), 7.03 (1H), 7.30 (1H), 7.36 (1H), 7.58 (1H), 7.85 (1H), 7.98 (1H), 8.73 (1H).

(+)-5-{2-Hydroxy-3-[1-(2-fluoro-5-trifluoromethylphenyl)-cyclopropyl]-2-phenyl-propionylamino}phthalide 3a and (−)-5-{2-Hydroxy-3-[1-(2-fluoro-5-trifluoromethylphenyl)-cyclopropyl]-2-(phenylethinyl)-propionylamino}phthalide 3b

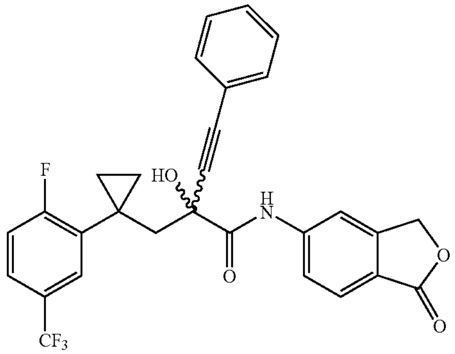

n-Butyllithium (625 μl, 1.6 M in hexane) was added at −78° C. to a solution of 110 μl of phenylacetylene in tetrahydrofuran. Stirring was allowed to continue at this temperature for 30 minutes, and then a solution of 5-{3-[1-(2-fluoro-5-trifluoromethylphenyl)-cyclopropyl]-2-oxopropionylamino}phthalide (210 mg) in 5 ml of tetrahydrofuran was added in drops. Then, it was allowed to come to 23° C. over about 3 hours and then stirred for 10 more hours. Then, the reaction mixture was poured into ice-cold, saturated ammonium chloride solution. It was extracted with ethyl acetate. The combined organic phases were washed with saturated sodium chloride solution and dried on sodium sulfate. The crude product was chromatographed on silica gel. The racemic mixture obtained was then separated by preparative chiral HPLC (Chiralpak AD column, 250×10 mm) into enantiomers 3a (46 mg) and 3b (47 mg).

3a and 3b:

$^{1}$H-NMR (ppm, $CDCl_3$, 300 MHz): 0.88 (1H), 0.95-1.11 (3H), 2.46 (1H), 2.65 (1H), 3.10 (1H), 5.27 (2H), 7.00 (1H), 7.24-7.42 (7H), 7.61 (1H), 7.84 (1H), 7.98 (1H), 8.80 (1H).

3a: $[\alpha]^{D}_{20}$: +12.9° ($CHCl_3$, 1.06 g/100 ml; λ=589 nM)

3b: $[\alpha]^{D}_{20}$: −14.4° ($CHCl_3$, 1.03 g100 ml; λ=589 nM)

Analogously to Example 3, compounds 4 and 5 were produced from 5-{3-[1-(2-fluoro-5-trifluoromethylphenyl)-cyclopropyl]-2-oxopropionylamino}phthalide and the respective lithium aryl acetylide.

rac-5-{2-Hydroxy-3-[1-(2-fluoro-5-trifluoromethylphenyl)-cyclopropyl]-2-[(4-trifluoromethylphenyl)ethinyl]propionylamino}phthalide 4

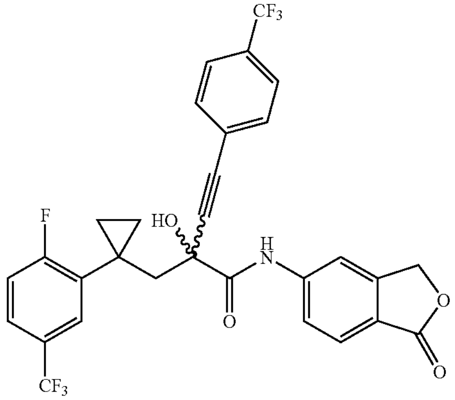

$^1$H-NMR (ppm, $CDCl_3$, 300 MHz): 0.92 (1H), 0.99-1.16 (3H), 2.55 (1H), 2.68 (1H), 3.27 (1H), 5.30 (2H), 7.03 (1H), 7.30-7.52 (4H), 7.55-7.62 (2H), 6.67 (1H), 7.99 (1H), 8.03 (1H), 8.84 (1H).

(+)-5-{2-Hydroxy-3-[1-(2-fluoro-5-trifluormethylphenyl)-cyclopropyl]-2-[(4-trifluormethylphenyl)ethinyl]propionylamino}phthalide 4a and (−)-5-{2-Hydroxy-3-[1-(2-fluoro-5-trifluormethylphenyl)-cyclopropyl]-2-[(4-trifluormethylphenyl)ethinyl]propionylamino}phthalide 4b The racemic mixture (150 mg) which was described in example 4 was separated by preparative chiral HPLC (column Chiralpak AD 250×10 mm) into the enantiomers 4a (51 mg) and 4b (62 mg).

4a: $[\alpha]^{D}_{20}$: +6.3° ($CHCl_3$, 1.07 g/100 ml; λ=589 nM)

4b: $[\alpha]^{D}_{20}$: −5.3° ($CHCl_3$, 1.09 g100 ml; λ=589 nM)

rac-5-{2-Hydroxy-3-[1-(2-fluoro-5-trifluoromethylphenyl)-cyclopropyl]-2-[(4-methylphenyl)ethinyl]propionylamino}phthalide 5

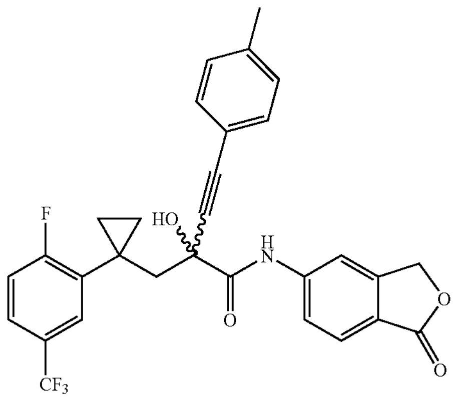

$^1$H-NMR (ppm, $CDCl_3$, 300 MHz): 0.87 (1H), 0.93-1.15 (3H), 2.38 (3H), 2.45 (1H), 2.66 (1H), 3.11 (1H), 5.25 (2H), 6.99 (1H), 7.10 (2H), 7.18-7.38 (4H), 7.61 (1H), 7.86 (1H), 8.00 (1H), 8.80 (1H).

(+)-5-{2-Hydroxy-3-[1-(2-fluoro-5-trifluoromethylphenyl)-cyclopropyl]-2-[(4-methylphenyl)ethinyl]propionylamino}phthalide 5a and (−)-5-{2-Hydroxy-3-[1-(2-fluoro-5-trifluoromethylphenyl)-cyclopropyl]-2-[(4-methylphenyl)ethiny]propionylamino}phthalide 5b The racemic mixture (109 mg) which was described in example 5 was separated by preparative chiral HPLC (column Chiralpak AD 250×10 mm) into the enantiomers 5a (41 mg) and 5b (28 mg).

5a: $[\alpha]^{D}_{20}$: +14.8° ($CHCl_3$, 1.07 g/100 ml; λ=589 nM)

5b: $[\alpha]^{D}_{20}$: −16.3° ($CHCl_3$, 1.13 g100 ml; λ=589 nM)

rac-5-{2-[(4-Acetoxyphenyl)ethinyl]-2-hydroxy-3-[1-(2-fluoro-5-trifluoromethylphenyl)-cyclopropyl]-propionylamino}phthalide 6

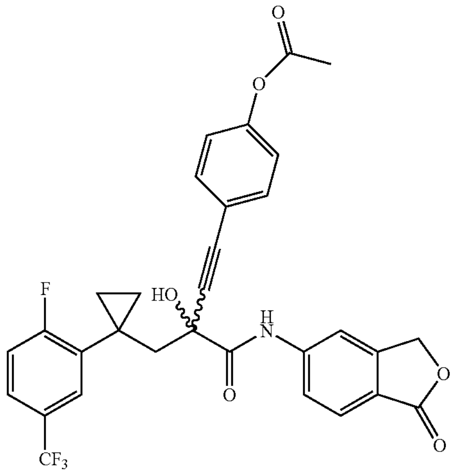

A suspension of the compound (104 mg) described under Example 1, triphenylphosphine (12.2 mg), copper iodide (8.9 mg), 4-iodophenyl acetate (92 mg), palladium acetate (5.3 mg) in THF (5 ml) and triethylamine (5 ml) was reacted for 1 hour in an ultrasound bath at 25° C. under argon. Then, it was poured into saturated, aqueous ammonium chloride solution. It was extracted with ethyl acetate and washed with water and saturated sodium chloride solution. The combined organic phases were dried on sodium sulfate. After column chromatography of the crude product on silica gel, 55 mg of product was obtained.

$^1$H-NMR (ppm, $CDCl_3$, 400 MHz): 0.88 (1H), 0.95-1.10 (3H), 2.29 (3H), 2.45 (1H), 2.63 (1H), 3.17 (1H), 5.29 (2H), 6.97-7.07 (3H), 7.28-7.37 (4H), 7.60 (1H), 7.84 (1H), 7.98 (1H), 8.80 (1H).

rac-5-{2-Hydroxy-2-[(4-hydroxyphenyl)ethinyl]-3-[1-(2-fluoro-5-trifluoromethylphenyl)-cyclopropyl]-propionylamino}phthalide 7

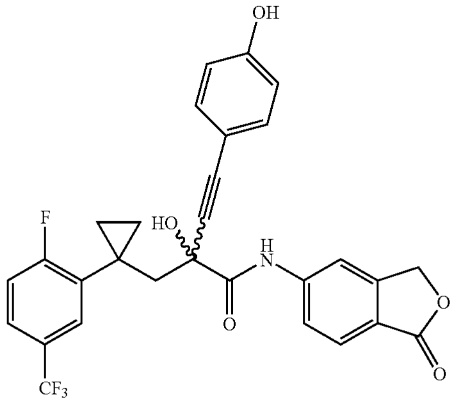

A solution of the compound described under 6 (45 mg) in 5 ml of methanol was mixed with sodium bicarbonate (130 mg). Stirring was continued for 2 more hours at 23° C. Then, the reaction mixture was diluted with ethyl acetate. Then, it was washed twice with saturated sodium chloride solution. After drying on sodium sulfate, the crude product was purified on silica gel by column chromatography. 38 mg of product was obtained.

$^1$H-NMR (ppm, $CDCl_3$, 300 MHz): 0.87 (1H), 0.92-1.11 (3H), 2.43 (1H), 2.64 (1H), 3.11 (1H), 5.27 (2H), 5.67 (1H), 6.73 (2H), 6.9.8 (1H), 7.14 (2H), 7.28-7.38 (2H), 7.60 (1H), 7.85 (1H), 7.97 (1H), 8.84 (1H).

rac-5-{2-[(4-Carboxyphenyl)ethinyl]-2-hydroxy-3-[1-(2-fluoro-5-trifluoromethylphenyl)-cyclopropyl]-propionylamino}phthalide 8

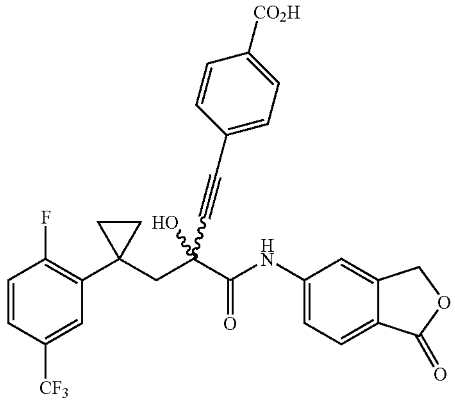

Analogously to Example 6, compound 8 was produced from the compound described under Example 1 and 4-iodobenzoic acid.

$^1$H-NMR (ppm, $CDCl_3$/MeOD (5%), 400 MHz): 0.82 (1H), 0.89-1.05 (3H), 2.37 (1H), 2.65 (1H), 5.24 (2H), 6.97 (1H), 7.35 (1H), 7.44 (2H), 7.50-7.65 (2H), 7.72 (1H), 7.80 (1H), 7.92 (2H).

rac-5-{2-Hydroxy-3-[1-(2-fluoro-5-trifluoromethylphenyl)-cyclopropyl]-2-(pentin-1-yl)-propionylamino}phthalide 9

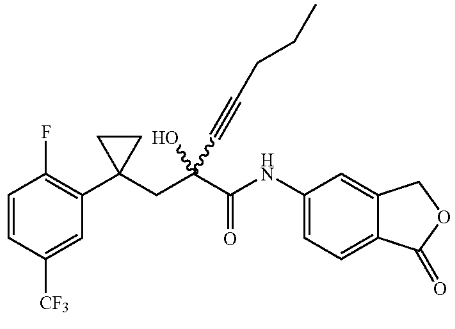

A solution that consists of 1-pentyne (0.94 ml) in THF (9 ml) was mixed at −78° C. with nBuLi (0.6 ml, 1.6 M in hexane). It was allowed to stir for 30 minutes at −78° C., and then a solution of 5-{3-[1-(2-fluoro-5-trifluoromethylphenyl)-cyclopropyl]-2-oxopropionylamino}phthalide (200 mg) in 3 ml of tetrahydrofuran was added. Then, it was allowed to come to 23° C. over about 3 hours, and it was stirred for 10 more hours at this temperature. Then, the reaction mixture was poured into ice-cold, saturated ammonium chloride solution. It was extracted with ethyl acetate. The combined organic phases were washed with saturated sodium chloride solution and dried on sodium sulfate. The crude product was chromatographed on silica gel. 130 mg of product was obtained.

$^1$H-NMR (ppm, $CDCl_3$, 400 MHz): 0.82 (1H), 0.92-1.07 (6H), 1.45 (2H), 2.08 (2H), 2.30 (1H), 2.53 (1H), 2.83 (1H), 5.27 (2H), 7.02 (1H), 7.29 (1H), 7.36 (1H), 7.57 (1H), 7.84 (1H), 7.96 (1H), 8.72 (1H).

(+)-5-{2-Hydroxy-3-[1-(2-fluoro-5-trifluoromethylphenyl)-cyclopropyl]-2-(pentin-1-yl)-propionylamino}phthalide 9a and (−)-5-{2-Hydroxy-3-[1-(2-fluoro-5-trifluoromethylphenyl)-cyclopropyl]-2-(pentin-1-yl)-propionylamino}phtlialide 9b The racemic mixture (120 mg) which was described in example 9 was separated by preparative chiral HPLC (column Chiralpak AD 250×10 mm) into the enantiomers 9a (46 mg) and 9b (47 mg).

9a: $[\alpha]^D_{20}$: +10.9° ($CHCl_3$, 1.01 g/100 ml; λ=589 nM)

9b: $[\alpha]^D_{20}$: −10.6° ($CHCl_3$, 1.08 g100 ml; λ=589 nM)

rac-5-{2-Hydroxy-3-[1-(2-fluoro-5-trifluoromethylphenyl)-cyclopropyl]-2-(hexin-1-yl)-propionylamino}phthalide 10

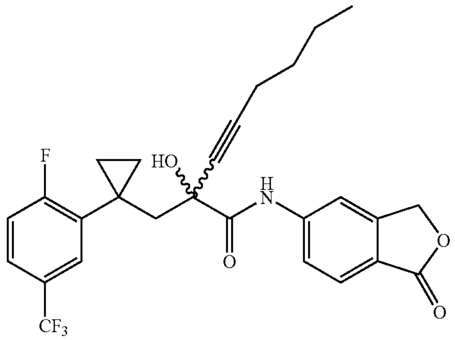

Compound 10 was synthesized analogously to Example 9.

$^1$H-NMR (ppm, $CDCl_3$, 400 MHz): 0.80-1.06 (7H), 1.30-1.50 (2H), 1.59 (2H), 2.10 (2H), 2.30 (1H), 2.52 (1H), 2.82 (1H), 5.28 (2H), 7.02 (1H), 7.30 (1H), 7.36 (1H), 7.57 (1H), 7.84 (1H), 7.95 (1H), 8.72 (1H).

rac-5-{2-Hydroxy-3-[1-(2-fluoro-5-trifluoromethylphenyl)-cyclopropyl]-2-[(4-hydroxy)butin-1-yl]-propionylamino}phthalide 11

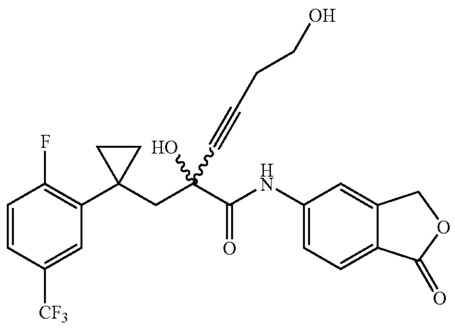

Stage A: Reaction of 4-(tert-butyldimethylsilyloxo)but-1-yne (175 mg), nBuLi (0.59 ml, 1.6 M in hexane) 5-{3-[1-(2-Fluoro-5-trifluoromethylphenyl)-cyclopropyl]-2-oxopropionylamino}-phthalide (200 mg) in tetrahydrofuran analogously to the process described under Example 9 yielded 165 mg of product.

Stage B: The product obtained under stage A (160 mg) was dissolved in 5 ml of tetrahydrofuran. At 0° C., 270 μl of a 1 molar solution of tetrabutylammonium fluoride in tetrahydrofuran was added and stirred for one hour at 0° C. and for another 2 hours at 23° C. Then, the reaction mixture was poured into saturated, aqueous sodium bicarbonate solution. It was extracted several times with ethyl acetate. The combined organic phases were washed with saturated sodium chloride solution and dried on sodium sulfate. After column chromatography on silica gel, 77 mg of product was obtained.

$^1$H-NMR (ppm, $CDCl_3$, 400 MHz): 0.83 (1H), 0.90-1.03 (3H), 2.20-2.40 (3H), 2.50 (1H), 3.39 (1H), 3.68 (2H), 5.25 (2H), 7.01 (1H), 7.32 (2H), 7.57 (1H), 7.82 (1H), 7.93 (1H), 8.91 (1H).

Analogously to Example 11, compounds 12 and 13 were produced from 5-{3-[1-(2-fluoro-5-trifluoromethylphenyl)-cyclopropyl]-2-oxopropionylamino}phthalide:

rac-5-{2-Hydroxy-3-[1-(2-fluoro-5-trifluoromethylphenyl)-cyclopropyl]-2-[(5-hydroxy)pentin-1-yl]-propionylamino}phthalide 12

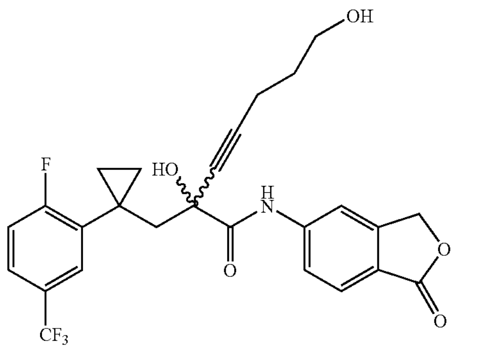

$^1$H-NMR (ppm, $CDCl_3$, 400 MHz): 0.83 (1H), 0.90-1.03 (3H), 1.70 (2H), 2.24 (2H), 2.33 (1H), 2.50 (1H), 3.09 (1H), 3.71 (2H), 5.26 (2H), 7.02 (1H), 7.35 (2H), 7.57 (1H), 7.83 (1H), 7.97 (1H), 8.82 (1H).

rac-5-{2-Hydroxy-3-[1-(2-fluoro-5-trifluoromethylphenyl)-cyclopropyl]-2-[(3-hydroxy)propin-1-yl]-propionylamino}phthalide 13

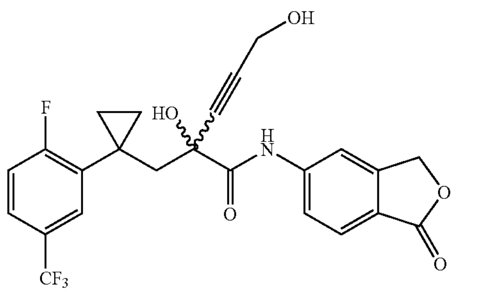

$^1$H-NMR (ppm, $CDC_3$, 400 MHz): 0.84 (1H), 0.90-1.03 (3H), 2.37 (1H), 2.52 (1H), 3.25 (1H), 4.17 (2H), 5.27 (2H), 7.02 (1H), 7.30-7.40 (2H), 7.58 (1H), 7.83 (1H), 7.91 (1H), 8.77 (1H).

(+)-5-{2-Hydroxy-3-[1-(2-fluoro-5-trifluoromethylphenyl)-cyclopropyl]-2-[(3-hydroxy)propin-1-yl]-propionylamino}phthalide 13a and (−)-5-{2-Hydroxy-3-[1-(2-fluoro-5-trifluoromethylphenyl)-cyclopropyl]-2-[(3-hydroxy)propin-1-yl]-propionylamino}phthalide 13b The racemic mixture (80 mg) which was described in example 13 was separated by preparative chiral HPLC (column Chiralpak AD 250×10 mm) into the enantiomers 13a (35 mg) and 13b (37 mg).

13a: $[\alpha]^D_{20}$: +28.3° ($CHCl_3$, 1.01 g/100 ml; λ=589 nM)

13b: $[\alpha]^D_{20}$: −29.3° ($CHCl_3$, 1.08 g100 ml; λ=589 nM)

rac-5-{2-Hydroxy-3-[1-(2-fluoro-5-trifluoromethylphenyl)-cyclopropyl]-2-[(4-hydroxy-3-methyl)butin-1-yl]-propionylamino}phthalide 14

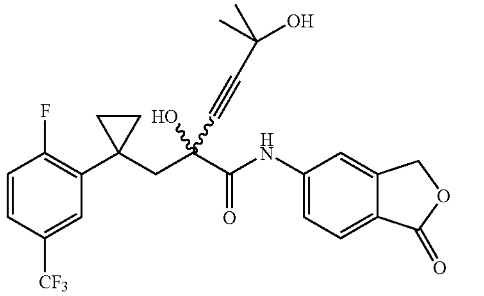

Stage A: Analogously to Example 11, 300 mg of 5-{3-[1-(2-fluoro-5-trifluoromethylphenyl)-cyclopropyl]-2-oxopropionylamino}phthalide and 282 mg of tert-butyl-(1,1-dimethylprop-2-ynyl-oxy)-dimethylsilane are reacted. 15 mg of product A is obtained.

Stage B: 70 mg of the compound that is obtained under A was dissolved in 1 ml of dichloromethane. 650 μl of trifluoroacetic acid (20% in dichloromethane) was added at 0° C., and it was stirred for 3.5 hours at 0° C. Then, it was evaporated to the dry state in a vacuum, and the residue was purified by column chromatography on silica gel. 27 mg of product was obtained.

$^1$H-NMR (ppm, $CDCl_3$, 400 MHz): 0.82 (1H), 0.90-1.00 (2H), 1.04 (1H), 1.47 (6H), 2.28 (1H), 2.58 (1H), 3.08 (1H), 5.27 (2H), 7.03 (1H), 7.30 (1H), 7.36 (1H), 7.59 (1H), 7.83 (1H), 7.91 (1H), 8.78 (1H).

rac-5-{2-Hydroxy-3-[1-(2-fluoro-5-trifluorometh-ylphenyl)-cyclopropyl]-2-(2-(tert-butylcarboxy) ethin-1-yl)-propionylamino}phthalide 15

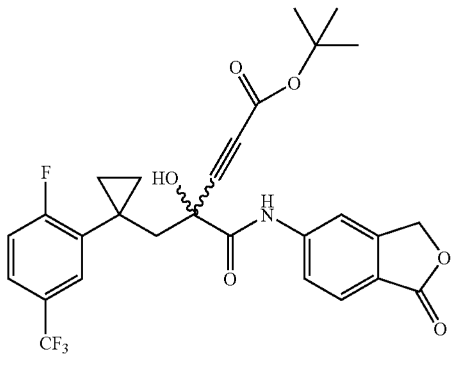

Compound 15 was synthesized analogously to Example 9.

$^1$H-NMR (ppm, $CDCl_3$, 400 MHz): 0.87 (1H), 0.93-1.05 (3H), 1.46 (9H), 2.42 (1H), 2.59 (1H), 3.39 (1H), 5.28 (2H), 7.03 (1H), 7.30-7.42 (2H), 7.57 (1H), 7.85 (1H), 7.92 (1H), 8.68 (1H).

rac-5-{2-Hydroxy-3-[1-(2-fluoro-5-trifluorometh-ylphenyl)-cyclopropyl]-2-(2-carboxyethin-1-yl)-propionylamino}phthalide 16

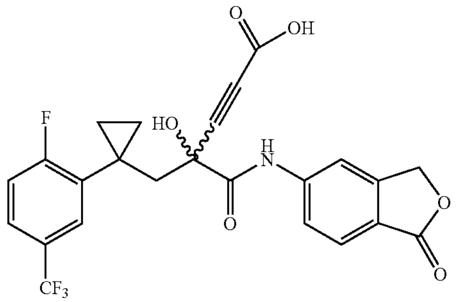

50 mg of the compound that is described under Example 15 was dissolved in 5 ml of dichloromethane. 100 μl of trifluoroacetic acid was added, and it was stirred for 12 more hours at 23° C. Then, it was evaporated to the dry state in a vacuum, and the residue was purified by column chromatography on silica gel. 36 mg of product was obtained.

$^1$H-NMR (ppm, DMSO-$D_6$, 300 MHz): 0.48 (1H), 0.78 (1H), 0.86 (1H), 1.09 (1H), 1.73 (1H), 2.89 (1H), 5.27 (2H), 6.62 (1H), 7.13 (1H), 7.31 (1H), 7.41 (1H), 7.53 (1H), 7.62 (1H), 7.68 (1H), 9.85 (1H).

Analogously to Example 3, compound 17 was produced from 5-{3-[1-phenyl-cyclopropyl]-2-oxopropionylamino}phthalide:

rac-5-{2-Hydroxy-3-[1-phenyl-cyclopropyl]-2-(phe-nyl-ethinyl)propionylamino}-phthalide 17

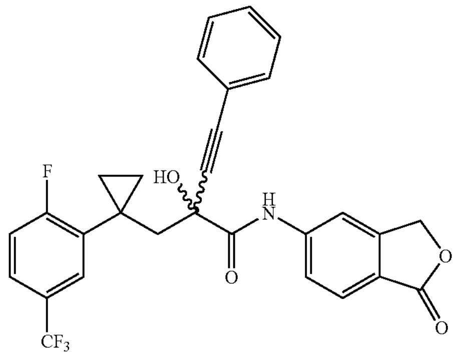

$^1$H-NMR (ppm, $CDCl_3$, 400 MHz): 0.78 (1H), 0.90 (1H), 1.10-1.21 (2H), 2.38 (1H), 2.72 (1H), 2.77 (1H), 5.28 (2H), 7.18 (1H), 7.25-7.42 (6H), 7.41-7.52 (4H), 7.82 (1H), 8.06 (1H), 8.79 (1H).

The entire disclosures of all applications, patents and publications, cited herein and of corresponding German application No. 102005030294.7, filed Jun. 24, 2005, and U.S. Provisional Application Ser. No. 60/693,404, filed Jun. 24, 2005 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I (I)

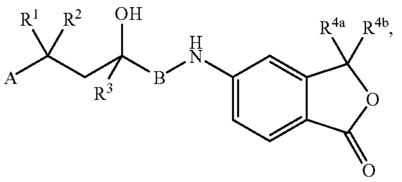

in which $R^1$ and $R^2$, independently of one another, mean a hydrogen atom, a straight or nonstraight, branched or unbranched $C_1$-$C_5$-alkyl group, or together with the C atom of the chain forming a ring with a total of 3-7 members, $R^3$ means a radical C≡C—$R^a$, wherein $R^a$ means a hydrogen or a $C_1$-$C_8$-alkyl, $C_2$-$C_8$-alkenyl, $C_2$-$C_8$-alkinyl, $C_3$-$C_{10}$-cycloalkyl, or heterocycloalkyl that optionally is substituted in one or more places, in the same way or differently, with K, or an aryl or heteroaryl that optionally is substituted in one or more places, in the same way or differently, with L, K is a cyano, halogen, hydroxy, nitro, —C(O)$R^b$, $CO_2R^b$, —O—$R^b$, —S—$R^b$, $SO_2NR^cR^d$, —C(O)—$NR^cR^d$, —OC(O)—$NR^cR^d$, or —C═$NOR^b$—$NR^cR^d$ or a $C_3$-$C_{10}$-cycloalkyl that optionally is substituted in one or more places, in the same way or differently, with M, heterocycloalkyl, or aryl or heteroaryl that optionally is substituted in one or more places with L, L means $C_1$-$C_8$-alkyl, $C_2$-$C_8$-alkenyl, $C_2$-$C_8$-alkinyl, $C_1$-$C_6$-perfluoroalkyl, $C_1$-$C_6$-perfluoroalkoxy, $C_1$-$C_6$-alkoxy-$C_1$-$C_6$-alkoxy, $(CH_2)_p$—$C_3$-$C_{10}$-cycloalkyl, $(CH_2)_p$-heterocycloalkyl, $(CH_2)_pCN$, $(CH_2)_pHal$, $(CH_2)_pNO_2$, $(CH_2)_p$—$C_6$-$C_{12}$-aryl, $(CH_2)_p$-heteroaryl, —$(CH_2)_pPO_3(R^b)_2$, —$(CH_2)_pNR^cR^d$, —$(CH_2)_pNR^eCOR^b$, —$(CH_2)_pNR^eCSR^b$, —$(CH_2)_pNR^eS(O)R^b$, —$(CH_2)_pNR^eS(O)_2R^b$, —$(CH_2)_pNR^eCONR^cR^d$, —$(CH_2)_pNR^eCOOR^b$, —$(CH_2)_pNR^eC(NH)NR^cR^d$, —$(CH_2)_pNR^eCSNR^cR^d$, —$(CH_2)_pNR^eS(O)NR^cR^d$, —$(CH_2)_pNR^eS(O)_2NR^cR^d$, —$(CH_2)_pCOR^b$, —$(CH_2)_pCSR^b$, —$(CH_2)_pS(O)R^b$, —$(CH_2)_pS(O)(NH)R^b$, —$(CH_2)_pS(O)_2R^b$, —$(CH_2)_pS(O)_2NR^cR^d$, —$(CH_2)_pSO_2OR^b$, —$(CH_2)_pCO_2R^b$, —$(CH_2)_pCONR^cR^d$, —$(CH_2)_pCSNR^cR^d$, —$(CH_2)_pOR^b$, —$(CH_2)_pSR^b$, —$(CH_2)_pCR^b(OH)$—$R^e$, —$(CH_2)_p$—C═NOR$^b$, —O—$(CH_2)_n$—O—, —O—$(CH_2)_n$—$CH_2$—, —O—CH═CH— or —$(CH_2)_{n+2}$—, wherein n=1 or 2, and the terminal oxygen atoms and/or carbon atoms are linked to directly adjacent ring-carbon atoms, M means $C_1$-$C_6$-alkyl or a group —COR$^b$, $CO_2R^b$, —O—$R^b$, or —NR$^c$R$^d$, wherein $R^b$ means a hydrogen or a $C_1$-$C_6$-alkyl, $C_2$-$C_8$-alkenyl, $C_2$-$C_8$-alkinyl, $C_3$-$C_{10}$-cycloalkyl, $C_6$-$C_{12}$-aryl or $C_1$-$C_3$-perfluoroalkyl and $R^c$ and $R^d$, independently of one another, mean a hydrogen, $C_1$-$C_6$-alkyl, $C_2$-$C_8$-alkenyl, $C_2$-$C_8$-alkinyl, $C_3$-$C_{10}$-cycloalkyl, $C_6$-$C_{12}$-aryl, C(O)$R^b$ or a hydroxy group, wherein if $R^c$ is a hydroxy group, $R^d$ can be only one hydrogen, a $C_1$-$C_6$-alkyl, $C_2$-$C_8$-alkenyl, $C_2$-$C_8$-alkinyl, $C_3$-$C_{10}$-cycloalkyl or $C_6$-$C_{12}$-aryl and vice versa, and $R^e$ means a hydrogen, $C_1$-$C_6$-alkyl, $C_2$-$C_8$-alkenyl, $C_2$-$C_8$-alkinyl, $C_3$-$C_{10}$-cycloalkyl or $C_6$-$C_{12}$-aryl, and p is a number from 0 to 6, $R^{4a}$ and $R^{4b}$, independently of one another, mean a hydrogen atom, a $C_1$-$C_4$-alkyl, a $C_2$-$C_4$-alkenyl or together with the ring-carbon atom forming a 3- to 6-membered ring, A means a monocyclic or bicyclic, carbocyclic or heterocyclic aromatic ring, which is optionally substituted in one or more places with $C_1$-$C_8$-alkyl, $C_2$-$C_8$-alkenyl, $C_2$-$C_8$-alkinyl, $C_1$-$C_6$-perfluoroalkyl, $C_1$-$C_6$-perfluoroalkoxy, $C_1$-$C_6$-alkoxy-$C_1$-$C_6$-alkyl, $C_1$-$C_6$-alkoxy-$C_1$-$C_6$-alkoxy, $(CH_2)_p$—$C_3$-$C_{10}$-cycloalkyl, $(CH_2)_p$-heterocycloalkyl, $(CH_2)_pCN$, $(CH_2)_pHal$, $(CH_2)_pNO_2$, $(CH_2)_p$—$C_6$-$C_{12}$-aryl, $(CH_2)_p$-heteroaryl, —$(CH_2)_pPO_3(R^b)_2$, —$(CH_2)_pNR^cR^d$, —$(CH_2)_pNR^eCOR^b$, —$(CH_2)_pNR^eCSR^b$, —$(CH_2)_pNR^eS(O)R^b$, —$(CH_2)_pNR^eS(O)_2R^b$, —$(CH_2)_pNR^eCONR^cR^d$, —$(CH_2)_pNR^eCOOR^b$, —$(CH_2)_pNR^eC(NH)NR^cR^d$, —$(CH_2)_pNR^eCSNR^cR^d$, —$(CH_2)_pNR^eS(O)NR^cR^d$, —$(CH_2)_pNR^eS(O)_2NR^cR^d$, —$(CH_2)_pCOR^b$, —$(CH_2)_pCSR^b$, —$(CH_2)_pS(O)R^b$, —$(CH_2)_pS(O)(NH)R^b$, —$(CH_2)_pS(O)_2R^b$, —$(CH_2)_pS(O)_2NR^cR^d$, —$(CH_2)_pSO_2OR^b$, —$(CH_2)_pCO_2R^b$, —$(CH_2)_pCONR^cR^d$, —$(CH_2)_pCSNR^cR^d$, —$(CH_2)_pOR^b$, —$(CH_2)_pSR^b$, —$(CH_2)_pCR^b(OH)$—$R^d$, —$(CH_2)_p$—C═NOR$^b$, —O—$(CH_2)_n$—O—, —O—$(CH_2)_n$—$CH_2$—, —O—CH═CH— or —$(CH_2)_{n+2}$—, wherein n=1 or 2, and the terminal oxygen atoms and/or carbon atoms are linked to directly adjacent ring-carbon atoms, and B means a carbonyl group, or a pharmaceutically acceptable salts thereof.

2. A compound according to claim 1, in which $R^1$ and $R^2$ mean a hydrogen atom, a methyl group or an ethyl group.

3. A compound according to claim 1, in which $R^1$ and $R^2$ together with the C atom of the chain form a ring with a total of 3 to 7 links.

4. A compound according to claim 1, in which $R^3$ means alkinyl, arylalkinyl, heteroarylalkinyl, cycloalkylalkinyl, or heterocycloalkylalkinyl.

5. A compound according to claim 1, in which $R^3$ means ethinyl, propinyl, butinyl, pentinyl, hexinyl, heptinyl, octinyl, hydroxypropinyl, hydroxybutinyl, 3-hydroxy-3-methylbutinyl, hydroxypentinyl, carboxypropinyl, t-butylcarboxypropinyl, phenylethinyl, (hydroxyphenyl)ethinyl, (methoxyphenyl)ethinyl, (dimethylaminophenyl)ethinyl, (methylphenyl)ethinyl, (cyanophenyl)ethinyl, (trifluoromethyl)ethinyl, (diphenyl)ethinyl, (nitrophenyl)ethinyl, (tert-butylphenyl)ethinyl, (acetylphenyl)ethinyl, (acetoxyphenyl)ethinyl, (carboxyphenyl)ethinyl or a benzylethinyl group.

6. A compound according to claim 1, in which A is an aromatic ring.

7. A compound according to claim 1, in which A is a phenyl or naphthyl radical.

8. A compound according to claim 7, in which A is an unsubstituted phenyl radical or a phenyl radical that is substituted in one or more places.

9. A compound according to claim 8, wherein the phenyl radical is substituted with one or two halogen atoms or a trifluoromethyl group.

10. A compound according to claim 9, in which the one or two halogen atoms are chlorine and/or fluorine.

11. A compound according to claim 1, in which A is an —O—$(CH_2)_n$—O— or —O—$(CH_2)_n$—$CH_2$-substituted phenyl ring, wherein the respectively directly adjacent ring-carbon atoms are linked.

12. A compound according to claim 1, in which $R^{4a}$ and $R^{4b}$, independently of one another, in each case are a hydrogen atom.

13. A compound according to claim 1, which is one of the following compounds

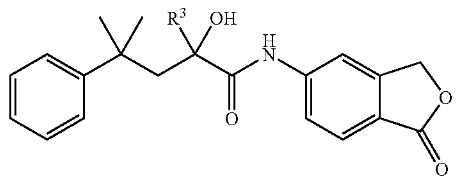

| No. | Racemic or Enantiomer | R3 |
|---|---|---|
| 1 | rac | 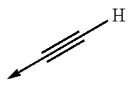 |
| 2 | + | |
| 3 | − | |
| 4 | rac | 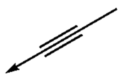 |
| 5 | + | |
| 6 | − | |

-continued
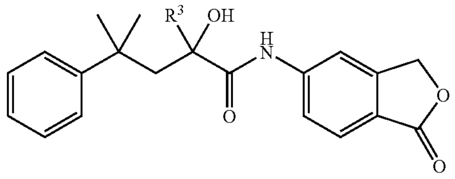
| No. | Racemic or Enantiomer | R3 |
|---|---|---|
| 7 | rac | 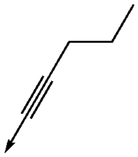 |
| 8 | + | |
| 9 | − | |
| 10 | rac | 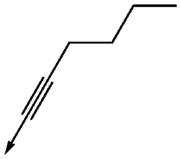 |
| 11 | + | |
| 12 | − | |
| 13 | rac | 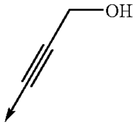 |
| 14 | + | |
| 15 | − | |
| 16 | rac | 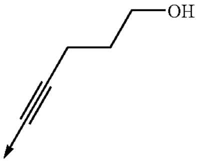 |
| 17 | + | |
| 18 | − | |
| 19 | rac | 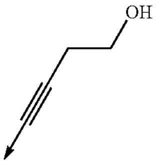 |
| 20 | + | |
| 21 | − | |
| 22 | rac | 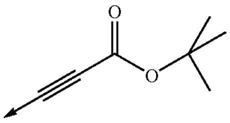 |
| 23 | + | |
| 24 | − | |
| 25 | rac | 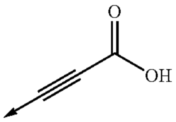 |
| 26 | + | |
| 27 | − | |
| 28 | rac | 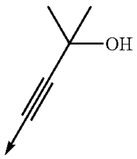 |
| 29 | + | |
| 30 | − | |
-continued
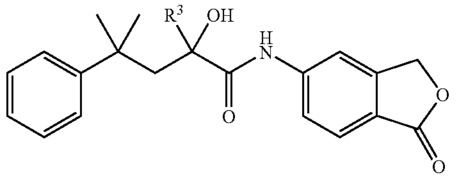
| No. | Racemic or Enantiomer | R3 |
|---|---|---|
| 31 | rac | 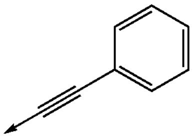 |
| 32 | + | |
| 33 | − | |
| 34 | rac | 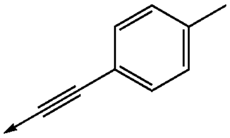 |
| 35 | + | |
| 36 | − | |
| 37 | rac | 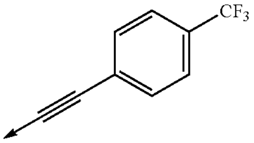 |
| 38 | + | |
| 39 | − | |
| 40 | rac | 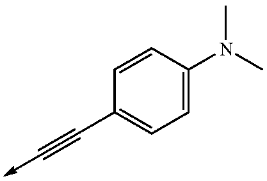 |
| 41 | + | |
| 42 | − | |
| 43 | rac | 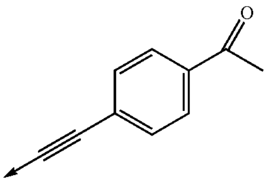 |
| 44 | + | |
| 45 | − | |
| 46 | rac | 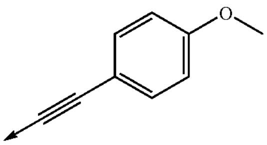 |
| 47 | + | |
| 48 | − | |
| 49 | rac | 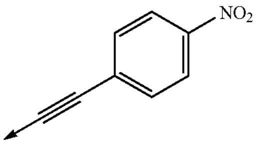 |
| 50 | + | |
| 51 | − | |
| 52 | rac | 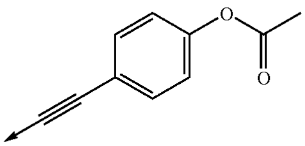 |
| 53 | + | |
| 54 | − | |

-continued
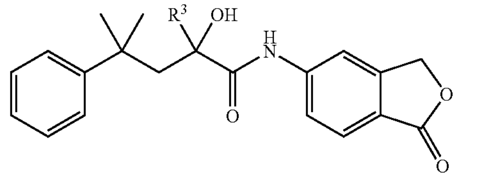
| No. | Racemic or Enantiomer | R3 |
|---|---|---|
| 55 | rac | 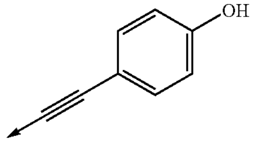 |
| 56 | + | |
| 57 | – | |
| 58 | rac | 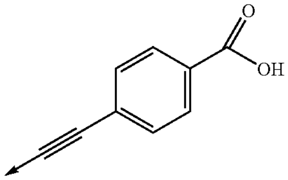 |
| 59 | + | |
| 60 | – | |
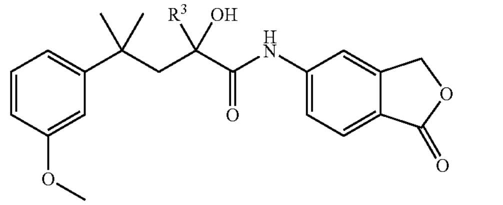
| No. | Racemic or Enantiomer | R3 |
|---|---|---|
| 61 | rac | 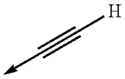 |
| 62 | + | |
| 63 | – | |
| 64 | rac | 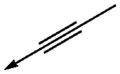 |
| 65 | + | |
| 66 | – | |
| 67 | rac | 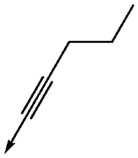 |
| 68 | + | |
| 69 | – | |
| 70 | rac | 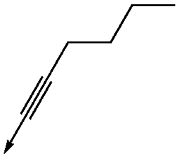 |
| 71 | + | |
| 72 | – | |
| 73 | rac | 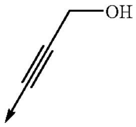 |
| 74 | + | |
| 75 | – | |
-continued
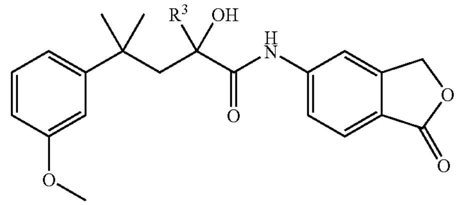
| No. | Racemic or Enantiomer | R3 |
|---|---|---|
| 76 | rac | 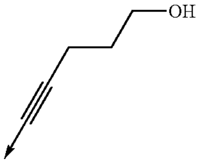 |
| 77 | + | |
| 78 | – | |
| 79 | rac | 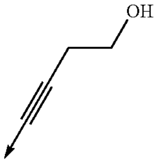 |
| 80 | + | |
| 81 | – | |
| 82 | rac | 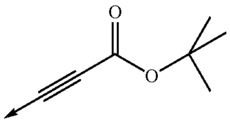 |
| 83 | + | |
| 84 | – | |
| 85 | rac | 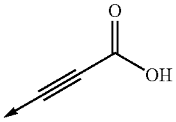 |
| 86 | + | |
| 87 | – | |
| 88 | rac | 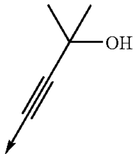 |
| 89 | + | |
| 90 | – | |
| 91 | rac | 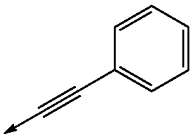 |
| 92 | + | |
| 93 | – | |
| 94 | rac | 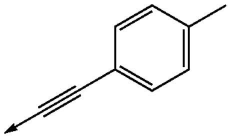 |
| 95 | + | |
| 96 | – | |
| 97 | rac | 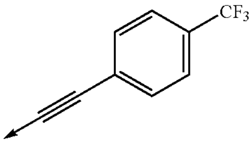 |
| 98 | + | |
| 99 | – | |

-continued
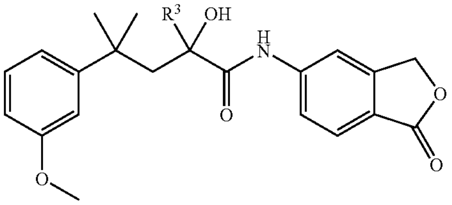
| No. | Racemic or Enantiomer | R3 |
|---|---|---|
| 100 | rac | 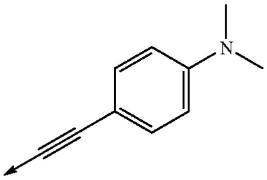 |
| 101 | + | |
| 102 | − | |
| 103 | rac | 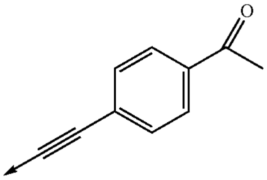 |
| 104 | + | |
| 105 | − | |
| 106 | rac | 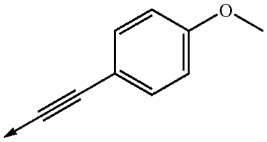 |
| 107 | + | |
| 108 | − | |
| 109 | rac | 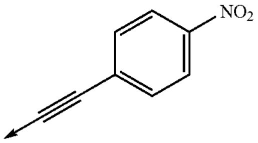 |
| 110 | + | |
| 111 | − | |
| 112 | rac | 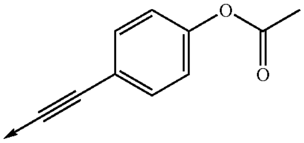 |
| 113 | + | |
| 114 | − | |
| 115 | rac | 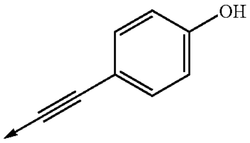 |
| 116 | + | |
| 117 | − | |
| 118 | rac | 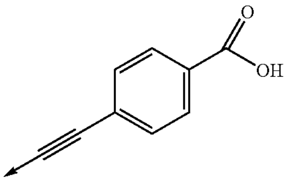 |
| 119 | + | |
| 120 | − | |
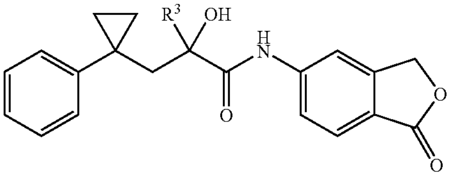
| No. | Racemic or Enantiomer | R3 |
|---|---|---|
| 121 | rac | 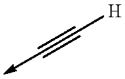 |
| 122 | + | |
| 123 | − | |
| 124 | rac | 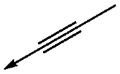 |
| 125 | + | |
| 126 | − | |
| 127 | rac | 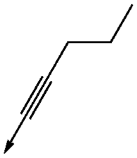 |
| 128 | + | |
| 129 | − | |
| 130 | rac | 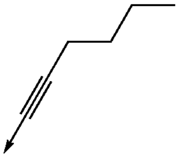 |
| 131 | + | |
| 132 | − | |
| 133 | rac | 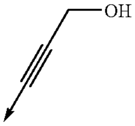 |
| 134 | + | |
| 135 | − | |
| 136 | rac | 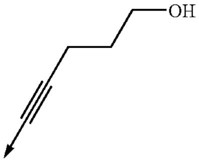 |
| 137 | + | |
| 138 | − | |
| 139 | rac | 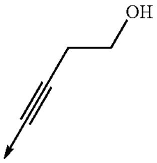 |
| 140 | + | |
| 141 | − | |
| 142 | rac | 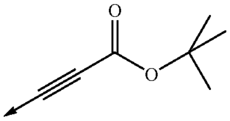 |
| 143 | + | |
| 144 | − | |
| 145 | rac | 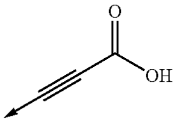 |
| 146 | + | |
| 147 | − | |

-continued
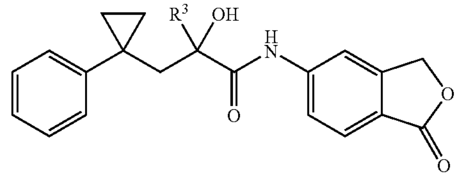
| No. | Racemic or Enantiomer | R3 |
|---|---|---|
| 148 | rac | 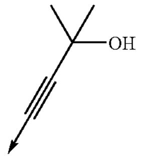 |
| 149 | + | |
| 150 | − | |
| 151 | rac | 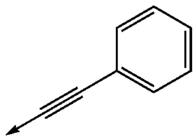 |
| 152 | + | |
| 153 | − | |
| 154 | rac | 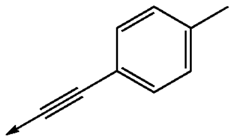 |
| 155 | + | |
| 156 | − | |
| 157 | rac | 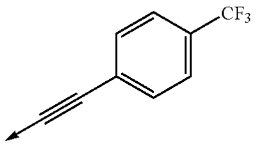 |
| 158 | + | |
| 159 | − | |
| 160 | rac | 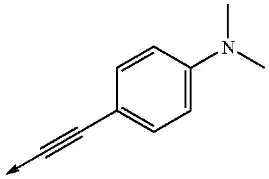 |
| 161 | + | |
| 162 | − | |
| 163 | rac | 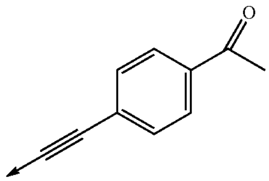 |
| 164 | + | |
| 165 | − | |
| 166 | rac | 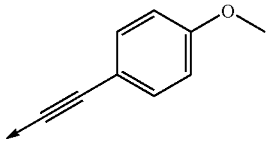 |
| 167 | + | |
| 168 | − | |
| 169 | rac | 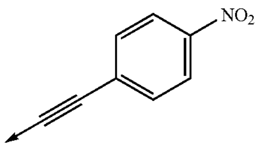 |
| 170 | + | |
| 171 | − | |
-continued
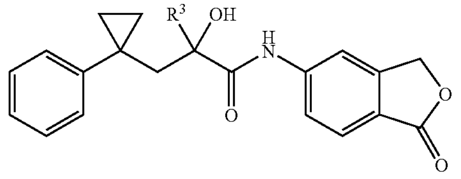
| No. | Racemic or Enantiomer | R3 |
|---|---|---|
| 172 | rac | 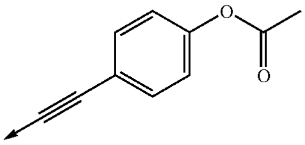 |
| 173 | + | |
| 174 | − | |
| 175 | rac | 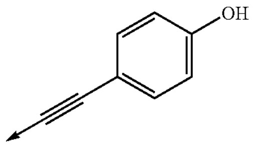 |
| 176 | + | |
| 177 | − | |
| 178 | rac | 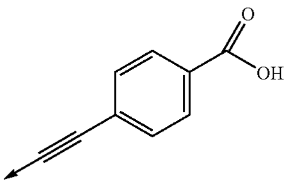 |
| 179 | + | |
| 180 | − | |
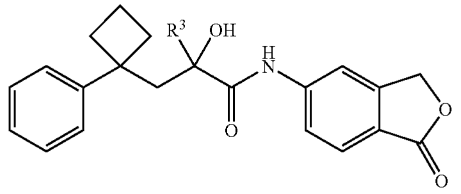
| No. | Racemic or Enantiomer | R3 |
|---|---|---|
| 181 | rac | 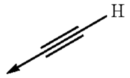 |
| 182 | + | |
| 183 | − | |
| 184 | rac | 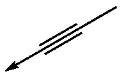 |
| 185 | + | |
| 186 | − | |
| 187 | rac | 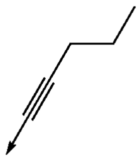 |
| 188 | + | |
| 189 | − | |

-continued
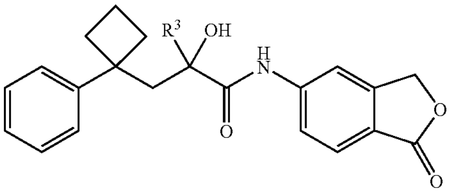
| No. | Racemic or Enantiomer | R3 |
| --- | --- | --- |
| 190 | rac | 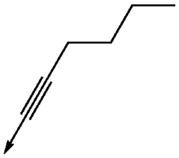 |
| 191 | + | |
| 192 | − | |
| 193 | rac | 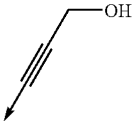 |
| 194 | + | |
| 195 | − | |
| 196 | rac | 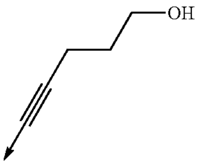 |
| 197 | + | |
| 198 | − | |
| 199 | rac | 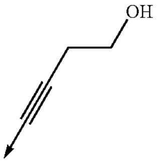 |
| 200 | + | |
| 201 | − | |
| 202 | rac | 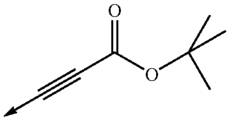 |
| 203 | + | |
| 204 | − | |
| 205 | rac | 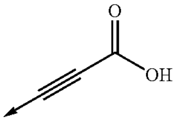 |
| 206 | + | |
| 207 | − | |
| 208 | rac | 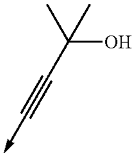 |
| 209 | + | |
| 210 | − | |
| 211 | rac | 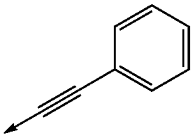 |
| 212 | + | |
| 213 | − | |
-continued
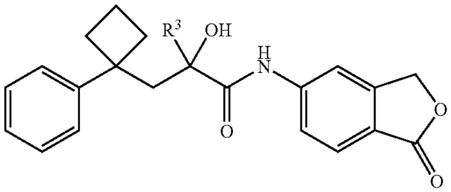
| No. | Racemic or Enantiomer | R3 |
| --- | --- | --- |
| 214 | rac | 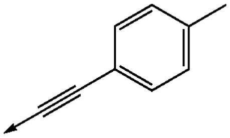 |
| 215 | + | |
| 216 | − | |
| 217 | rac | 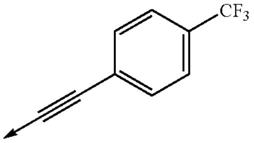 |
| 218 | + | |
| 219 | − | |
| 220 | rac | 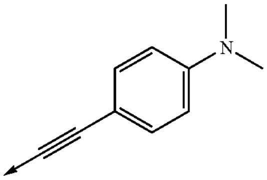 |
| 221 | + | |
| 222 | − | |
| 223 | rac | 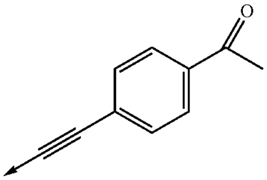 |
| 224 | + | |
| 225 | − | |
| 226 | rac | 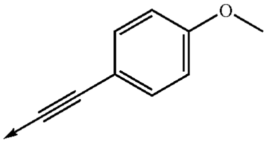 |
| 227 | + | |
| 228 | − | |
| 229 | rac | 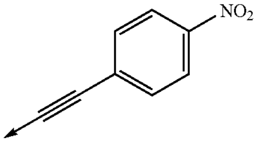 |
| 230 | + | |
| 231 | − | |
| 232 | rac | 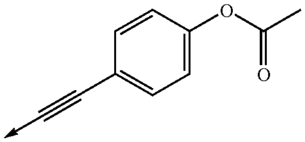 |
| 233 | + | |
| 234 | − | |
| 235 | rac | 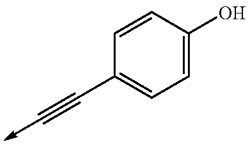 |
| 236 | + | |
| 237 | − | |

-continued
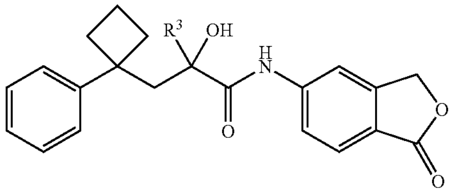
| No. | Racemic or Enantiomer | R3 |
| --- | --- | --- |
| 238 | rac | 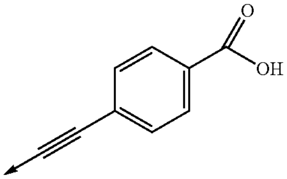 |
| 239 | + | |
| 240 | − | |
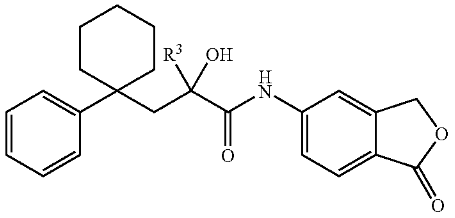
| No. | Racemic or Enantiomer | R3 |
| --- | --- | --- |
| 241 | rac | 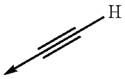 |
| 242 | + | |
| 243 | − | |
| 244 | rac | 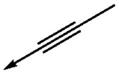 |
| 245 | + | |
| 246 | − | |
| 247 | rac | 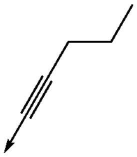 |
| 248 | + | |
| 249 | − | |
| 250 | rac | 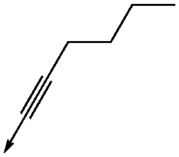 |
| 251 | + | |
| 252 | − | |
| 253 | rac | 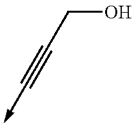 |
| 254 | + | |
| 255 | − | |
-continued
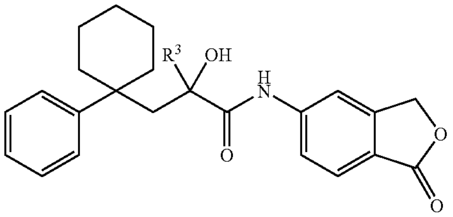
| No. | Racemic or Enantiomer | R3 |
| --- | --- | --- |
| 256 | rac | 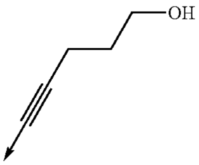 |
| 257 | + | |
| 258 | − | |
| 259 | rac | 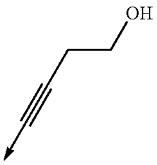 |
| 260 | + | |
| 261 | − | |
| 262 | rac | 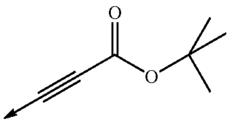 |
| 263 | + | |
| 264 | − | |
| 265 | rac | 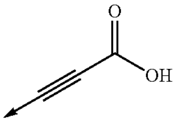 |
| 266 | + | |
| 267 | − | |
| 268 | rac | 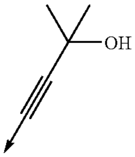 |
| 269 | + | |
| 270 | − | |
| 271 | rac | 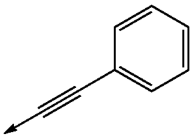 |
| 272 | + | |
| 273 | − | |
| 274 | rac | 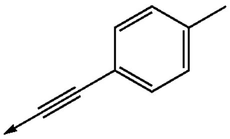 |
| 275 | + | |
| 276 | − | |
| 277 | rac | 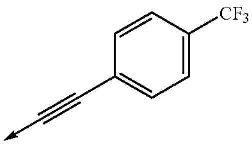 |
| 278 | + | |
| 279 | − | |

-continued
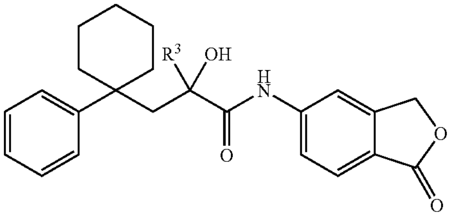
| No. | Racemic or Enantiomer | R3 |
|---|---|---|
| 280 | rac | 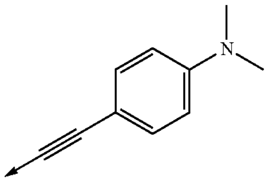 |
| 281 | + | |
| 282 | − | |
| 283 | rac | 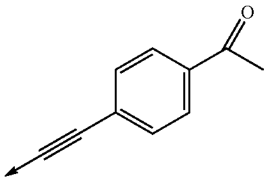 |
| 284 | + | |
| 285 | − | |
| 286 | rac | 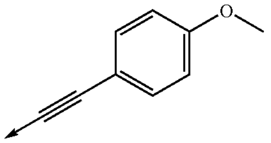 |
| 287 | + | |
| 288 | − | |
| 289 | rac | 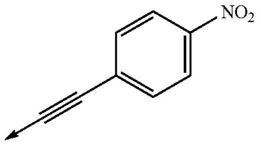 |
| 290 | + | |
| 291 | − | |
| 292 | rac | 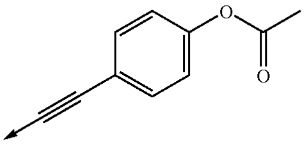 |
| 293 | + | |
| 294 | − | |
| 295 | rac | 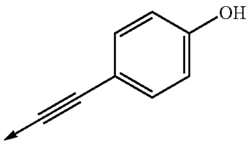 |
| 296 | + | |
| 297 | − | |
| 298 | rac | 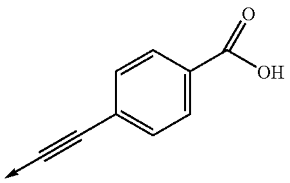 |
| 299 | + | |
| 300 | − | |
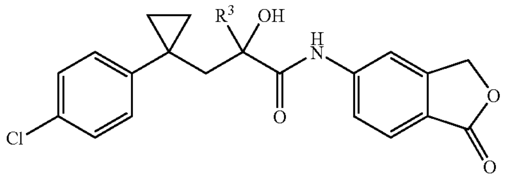
| No. | Racemic or Enantiomer | R3 |
|---|---|---|
| 301 | rac | 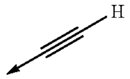 |
| 302 | + | |
| 303 | − | |
| 304 | rac | 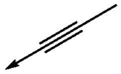 |
| 305 | + | |
| 306 | − | |
| 307 | rac | 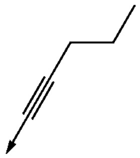 |
| 308 | + | |
| 309 | − | |
| 310 | rac | 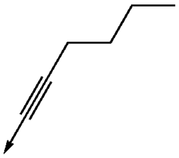 |
| 311 | + | |
| 312 | − | |
| 313 | rac | 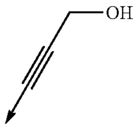 |
| 314 | + | |
| 315 | − | |
| 316 | rac | 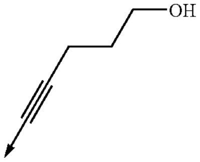 |
| 317 | + | |
| 318 | − | |
| 319 | rac | 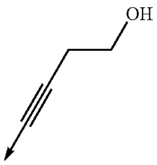 |
| 320 | + | |
| 321 | − | |
| 322 | rac | 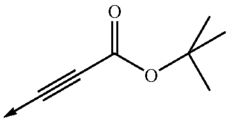 |
| 323 | + | |
| 324 | − | |
| 325 | rac | 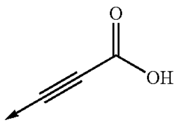 |
| 326 | + | |
| 327 | − | |

-continued

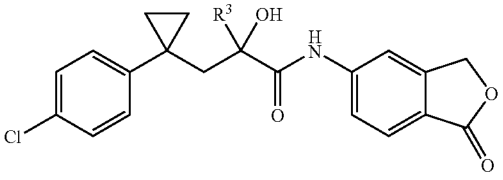

| No. | Racemic or Enantiomer | R3 |
|---|---|---|
| 328<br>329<br>330 | rac<br>+<br>− | 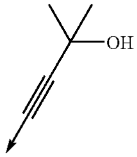 |
| 331<br>332<br>333 | rac<br>+<br>− | 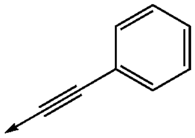 |
| 334<br>335<br>336 | rac<br>+<br>− | 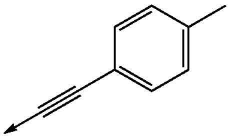 |
| 337<br>338<br>339 | rac<br>+<br>− | 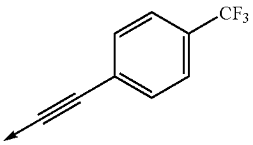 |
| 340<br>341<br>342 | rac<br>+<br>− | 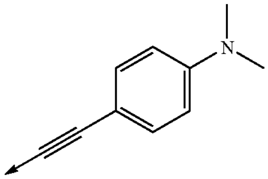 |
| 343<br>344<br>345 | rac<br>+<br>− | 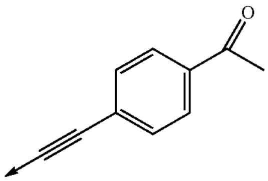 |
| 346<br>347<br>348 | rac<br>+<br>− | 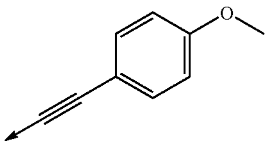 |
| 349<br>350<br>351 | rac<br>+<br>− | 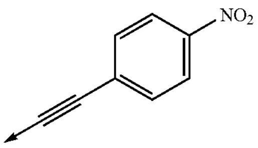 |

-continued

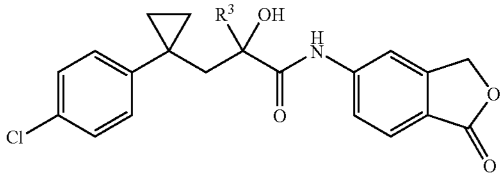

| No. | Racemic or Enantiomer | R3 |
|---|---|---|
| 352<br>353<br>354 | rac<br>+<br>− | 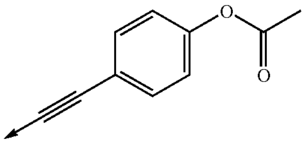 |
| 355<br>356<br>357 | rac<br>+<br>− | 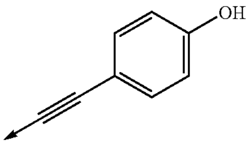 |
| 358<br>359<br>360 | rac<br>+<br>− | 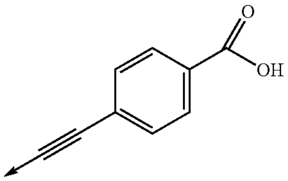 |

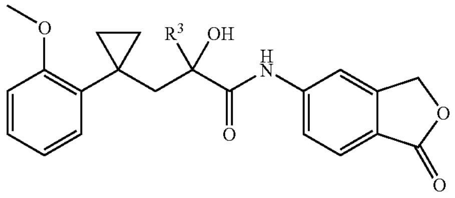

| No. | Racemic or Enantiomer | R3 |
|---|---|---|
| 361<br>362<br>363 | rac<br>+<br>− | 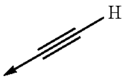 |
| 364<br>365<br>366 | rac<br>+<br>− | 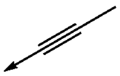 |
| 367<br>368<br>369 | rac<br>+<br>− | 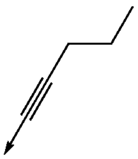 |

-continued
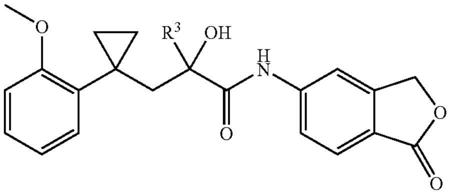
| No. | Racemic or Enantiomer | R3 |
|---|---|---|
| 370 | rac | 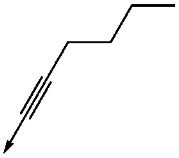 |
| 371 | + | |
| 372 | – | |
| 373 | rac | 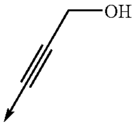 |
| 374 | + | |
| 375 | – | |
| 376 | rac | 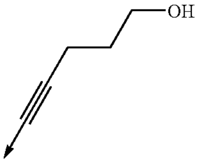 |
| 377 | + | |
| 378 | – | |
| 379 | rac | 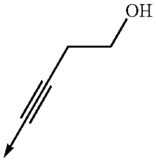 |
| 380 | + | |
| 381 | – | |
| 382 | rac | 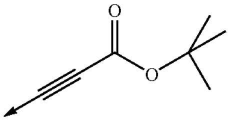 |
| 383 | + | |
| 384 | – | |
| 385 | rac | 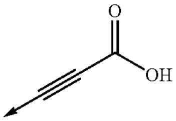 |
| 386 | + | |
| 387 | – | |
| 388 | rac | 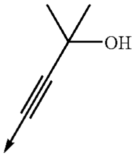 |
| 389 | + | |
| 390 | – | |
| 391 | rac | 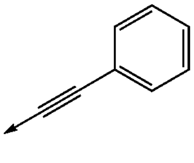 |
| 392 | + | |
| 393 | – | |
-continued
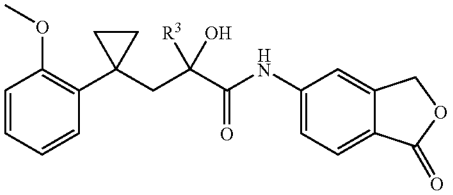
| No. | Racemic or Enantiomer | R3 |
|---|---|---|
| 394 | rac | 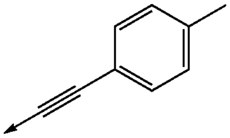 |
| 395 | + | |
| 396 | – | |
| 397 | rac | 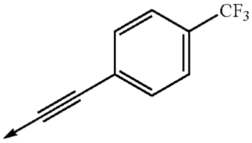 |
| 398 | + | |
| 399 | – | |
| 400 | rac | 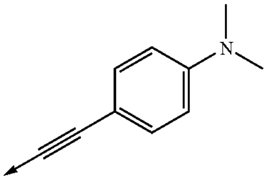 |
| 401 | + | |
| 402 | – | |
| 403 | rac | 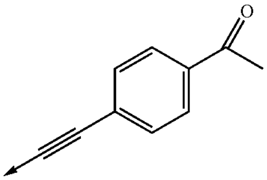 |
| 404 | + | |
| 405 | – | |
| 406 | rac | 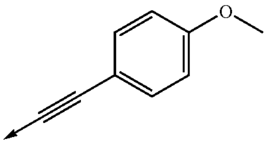 |
| 407 | + | |
| 408 | – | |
| 409 | rac | 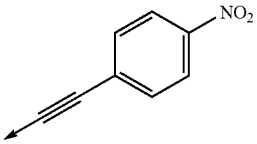 |
| 410 | + | |
| 411 | – | |
| 412 | rac | 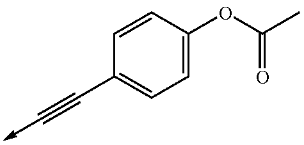 |
| 413 | + | |
| 414 | – | |
| 415 | rac | 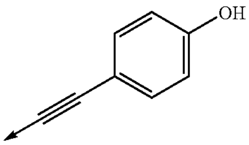 |
| 416 | + | |
| 417 | – | |

-continued
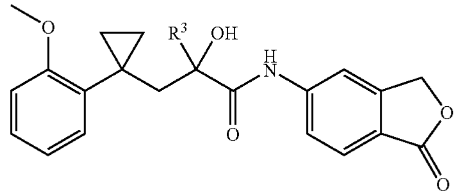
| No. | Racemic or Enantiomer | R3 |
|---|---|---|
| 418 | rac | 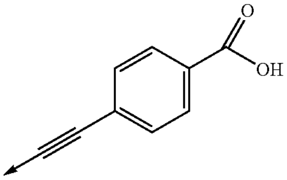 |
| 419 | + | |
| 420 | − | |
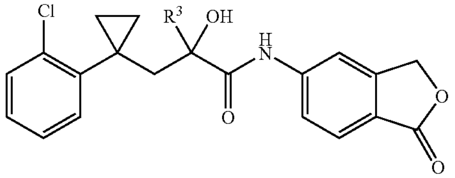
| No. | Racemic or Enantiomer | R3 |
|---|---|---|
| 421 | rac | 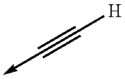 |
| 422 | + | |
| 423 | − | |
| 424 | rac | 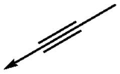 |
| 425 | + | |
| 426 | − | |
| 427 | rac | 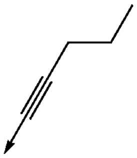 |
| 428 | + | |
| 429 | − | |
| 430 | rac | 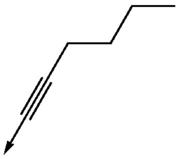 |
| 431 | + | |
| 432 | − | |
| 433 | rac | 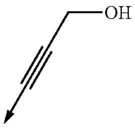 |
| 434 | + | |
| 435 | − | |
-continued
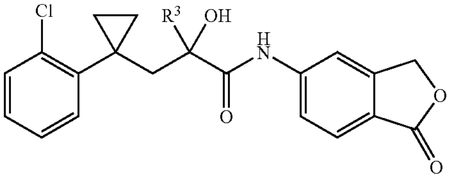
| No. | Racemic or Enantiomer | R3 |
|---|---|---|
| 436 | rac | 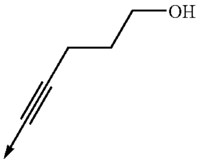 |
| 437 | + | |
| 438 | − | |
| 439 | rac | 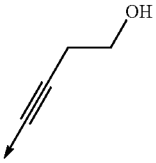 |
| 440 | + | |
| 441 | − | |
| 442 | rac | 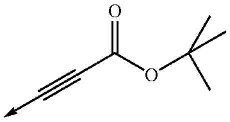 |
| 443 | + | |
| 444 | − | |
| 445 | rac | 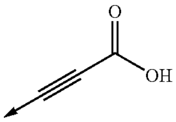 |
| 446 | + | |
| 447 | − | |
| 448 | rac | 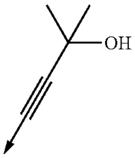 |
| 449 | + | |
| 450 | − | |
| 451 | rac | 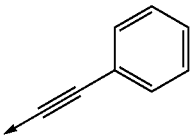 |
| 452 | + | |
| 453 | − | |
| 454 | rac | 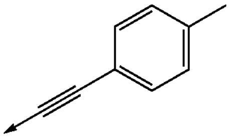 |
| 455 | + | |
| 456 | − | |
| 457 | rac | 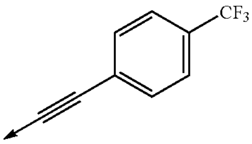 |
| 458 | + | |
| 459 | − | |

-continued
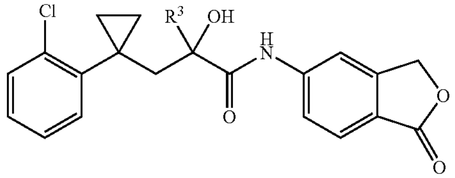
| No. | Racemic or Enantiomer | R3 |
|---|---|---|
| 460 | rac | 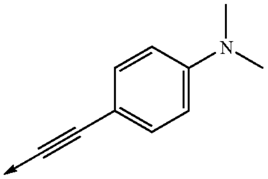 |
| 461 | + | |
| 462 | − | |
| 463 | rac | 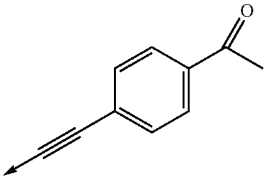 |
| 464 | + | |
| 465 | − | |
| 466 | rac | 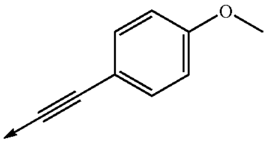 |
| 467 | + | |
| 468 | − | |
| 469 | rac | 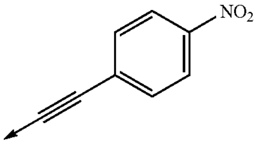 |
| 470 | + | |
| 471 | − | |
| 472 | rac | 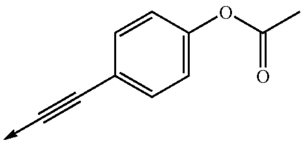 |
| 473 | + | |
| 474 | − | |
| 475 | rac | 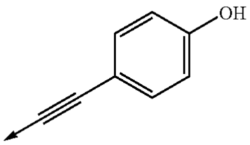 |
| 476 | + | |
| 477 | − | |
| 478 | rac | 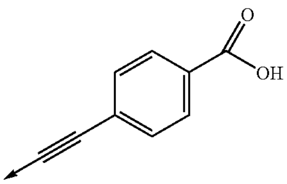 |
| 479 | + | |
| 480 | − | |
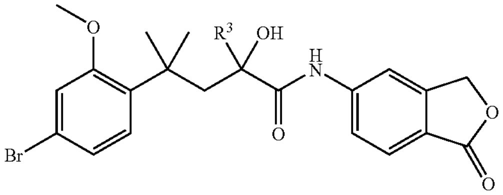
| No. | Racemic or Enantiomer | R3 |
|---|---|---|
| 481 | rac | 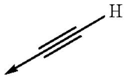 |
| 482 | + | |
| 483 | − | |
| 484 | rac | 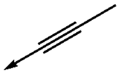 |
| 485 | + | |
| 486 | − | |
| 487 | rac | 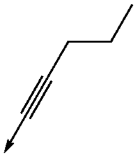 |
| 488 | + | |
| 489 | − | |
| 490 | rac | 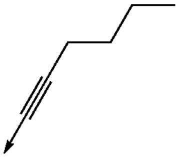 |
| 491 | + | |
| 492 | − | |
| 493 | rac | 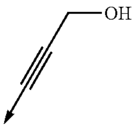 |
| 494 | + | |
| 495 | − | |
| 496 | rac | 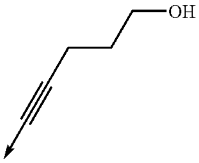 |
| 497 | + | |
| 498 | − | |
| 499 | rac | 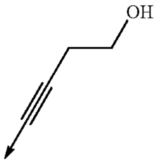 |
| 500 | + | |
| 501 | − | |
| 502 | rac | 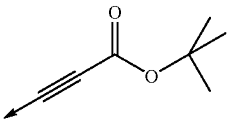 |
| 503 | + | |
| 504 | − | |
| 505 | rac | 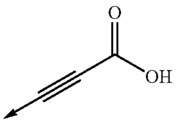 |
| 506 | + | |
| 507 | − | |

-continued
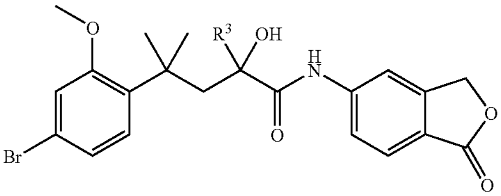
| No. | Racemic or Enantiomer | R3 |
|---|---|---|
| 508 | rac | 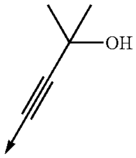 |
| 509 | + | |
| 510 | − | |
| 511 | rac | 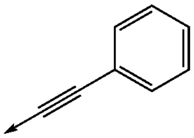 |
| 512 | + | |
| 513 | − | |
| 214 | rac | 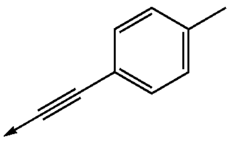 |
| 515 | + | |
| 516 | − | |
| 517 | rac | 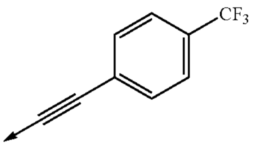 |
| 518 | + | |
| 519 | − | |
| 520 | rac | 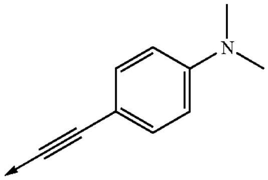 |
| 521 | + | |
| 522 | − | |
| 523 | rac | 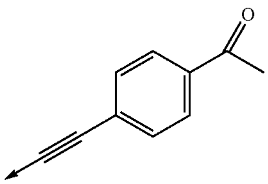 |
| 524 | + | |
| 525 | − | |
| 526 | rac | 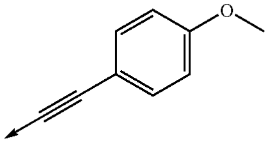 |
| 227 | + | |
| 528 | − | |
| 529 | rac | 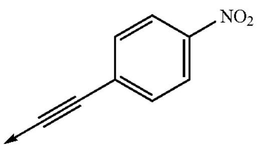 |
| 530 | + | |
| 531 | − | |
-continued
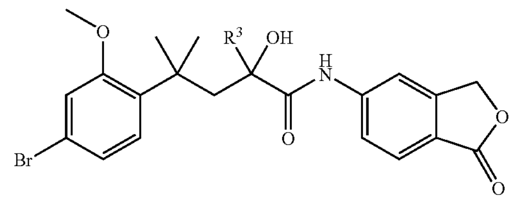
| No. | Racemic or Enantiomer | R3 |
|---|---|---|
| 532 | rac | 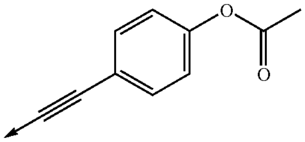 |
| 533 | + | |
| 534 | − | |
| 535 | rac | 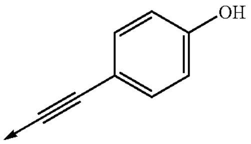 |
| 536 | + | |
| 537 | − | |
| 538 | rac | 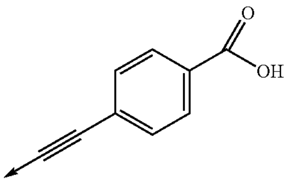 |
| 539 | + | |
| 540 | − | |
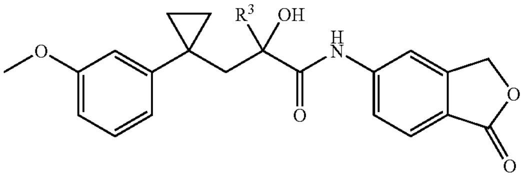
| No. | Racemic or Enantiomer | R3 |
|---|---|---|
| 541 | rac | 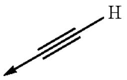 |
| 542 | + | |
| 543 | − | |
| 544 | rac | 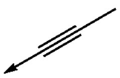 |
| 545 | + | |
| 546 | − | |
| 547 | rac | 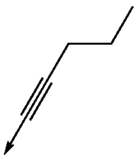 |
| 548 | + | |
| 549 | − | |

-continued
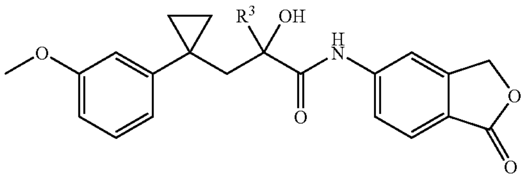
| No. | Racemic or Enantiomer | R3 |
|---|---|---|
| 550 | rac | 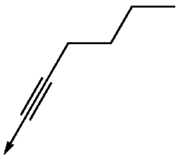 |
| 551 | + | |
| 552 | − | |
| 553 | rac | 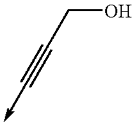 |
| 554 | + | |
| 555 | − | |
| 556 | rac | 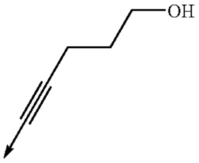 |
| 557 | + | |
| 558 | − | |
| 559 | rac | 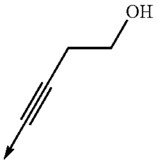 |
| 560 | + | |
| 561 | − | |
| 562 | rac | 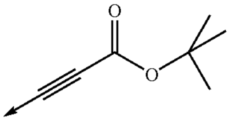 |
| 563 | + | |
| 564 | − | |
| 565 | rac | 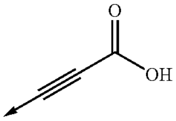 |
| 566 | + | |
| 567 | − | |
| 568 | rac | 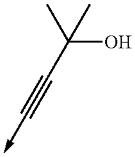 |
| 569 | + | |
| 570 | − | |
| 571 | rac | 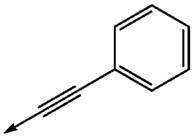 |
| 572 | + | |
| 573 | − | |
-continued
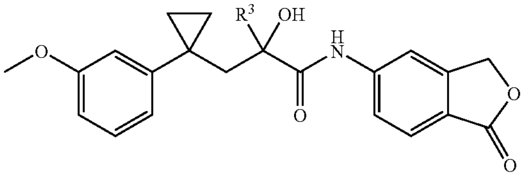
| No. | Racemic or Enantiomer | R3 |
|---|---|---|
| 574 | rac | 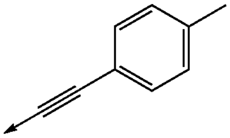 |
| 575 | + | |
| 576 | − | |
| 577 | rac | 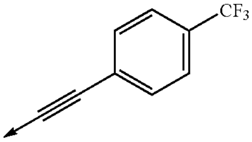 |
| 578 | + | |
| 579 | − | |
| 580 | rac | 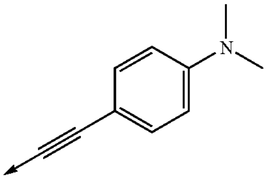 |
| 581 | + | |
| 582 | − | |
| 583 | rac | 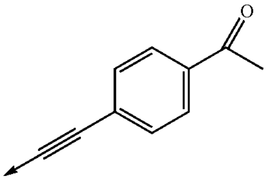 |
| 584 | + | |
| 585 | − | |
| 586 | rac | 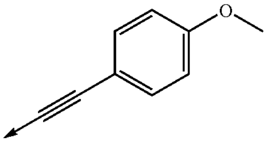 |
| 587 | + | |
| 588 | − | |
| 589 | rac | 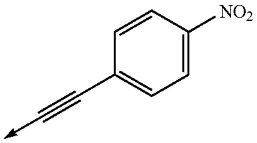 |
| 590 | + | |
| 591 | − | |
| 592 | rac | 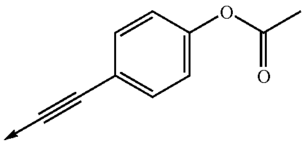 |
| 593 | + | |
| 594 | − | |
| 595 | rac | 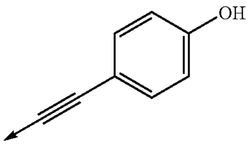 |
| 596 | + | |
| 597 | − | |

-continued
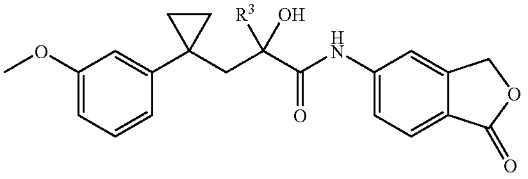
| No. | Racemic or Enantiomer | R3 |
|---|---|---|
| 598 | rac | 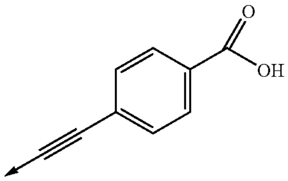 |
| 599 | + | |
| 600 | − | |
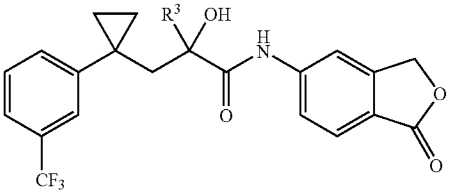
| No. | Racemic or Enantiomer | R3 |
|---|---|---|
| 601 | rac | 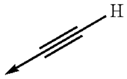 |
| 602 | + | |
| 603 | − | |
| 604 | rac | 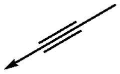 |
| 605 | + | |
| 606 | − | |
| 607 | rac | 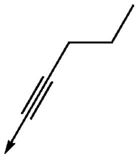 |
| 608 | + | |
| 609 | − | |
| 610 | rac | 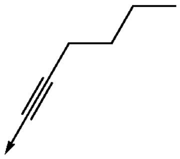 |
| 611 | + | |
| 612 | − | |
| 613 | rac | 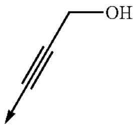 |
| 614 | + | |
| 615 | − | |
-continued
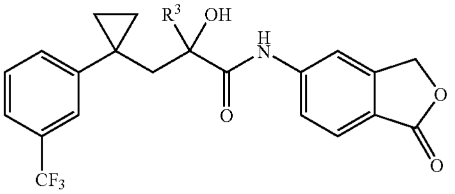
| No. | Racemic or Enantiomer | R3 |
|---|---|---|
| 616 | rac | 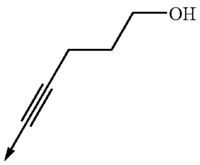 |
| 617 | + | |
| 618 | − | |
| 619 | rac | 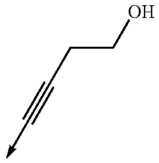 |
| 620 | + | |
| 621 | − | |
| 622 | rac | 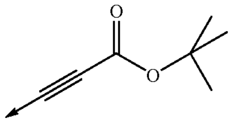 |
| 623 | + | |
| 624 | − | |
| 625 | rac | 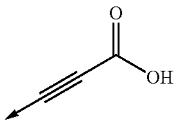 |
| 626 | + | |
| 627 | − | |
| 628 | rac | 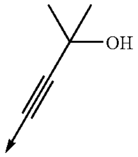 |
| 629 | + | |
| 630 | − | |
| 631 | rac | 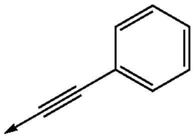 |
| 632 | + | |
| 633 | − | |
| 634 | rac | 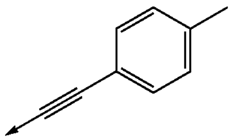 |
| 635 | + | |
| 636 | − | |
| 637 | rac | 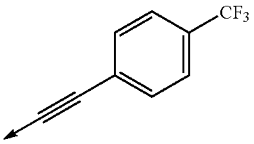 |
| 638 | + | |
| 639 | − | |

-continued
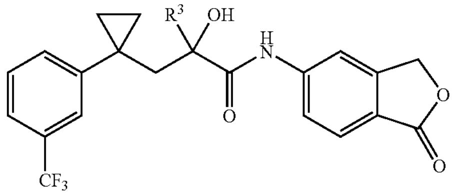
| No. | Racemic or Enantiomer | R3 |
|---|---|---|
| 640 | rac | 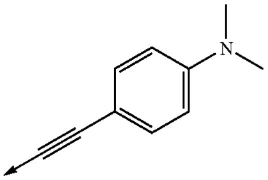 |
| 641 | + | |
| 642 | – | |
| 643 | rac | 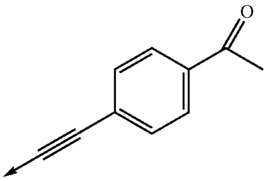 |
| 644 | + | |
| 645 | – | |
| 646 | rac | 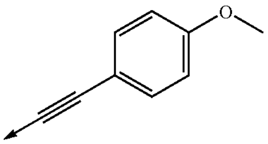 |
| 647 | + | |
| 648 | – | |
| 649 | rac | 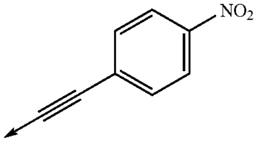 |
| 650 | + | |
| 651 | – | |
| 652 | rac | 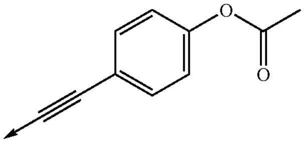 |
| 653 | + | |
| 654 | – | |
| 655 | rac | 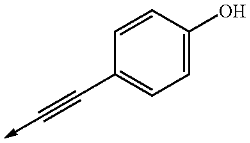 |
| 656 | + | |
| 657 | – | |
| 658 | rac | 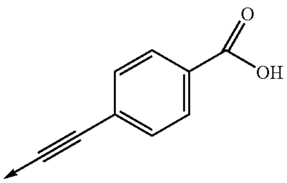 |
| 659 | + | |
| 660 | – | |
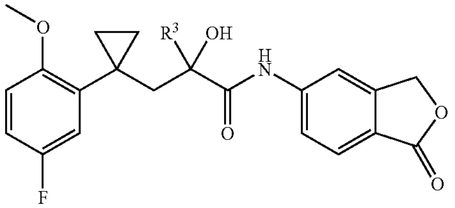
| No. | Racemic or Enantiomer | R3 |
|---|---|---|
| 661 | rac | 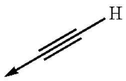 |
| 662 | + | |
| 663 | – | |
| 664 | rac | 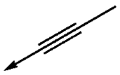 |
| 665 | + | |
| 666 | – | |
| 667 | rac | 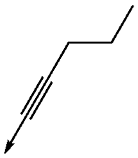 |
| 668 | + | |
| 669 | – | |
| 670 | rac | 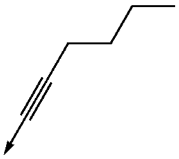 |
| 671 | + | |
| 672 | – | |
| 673 | rac | 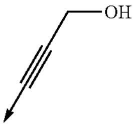 |
| 674 | + | |
| 675 | – | |
| 676 | rac | 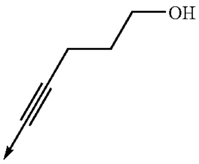 |
| 677 | + | |
| 678 | – | |
| 679 | rac | 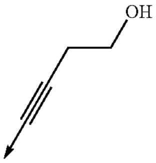 |
| 680 | + | |
| 681 | – | |
| 682 | rac | 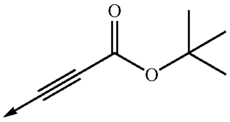 |
| 683 | + | |
| 684 | – | |
| 685 | rac | 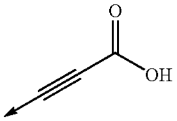 |
| 686 | + | |
| 687 | – | |

-continued
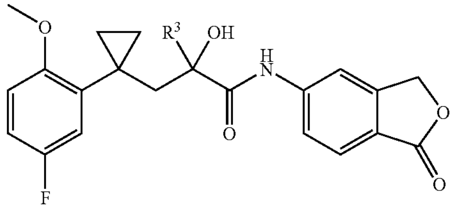
| No. | Racemic or Enantiomer | R3 |
|---|---|---|
| 688 | rac | 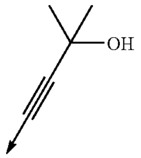 |
| 689 | + | |
| 690 | − | |
| 691 | rac | 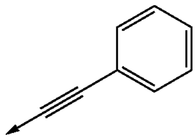 |
| 692 | + | |
| 693 | − | |
| 694 | rac | 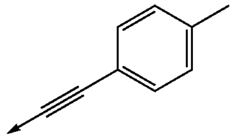 |
| 695 | + | |
| 696 | − | |
| 697 | rac | 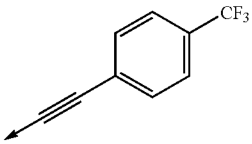 |
| 698 | + | |
| 699 | − | |
| 700 | rac | 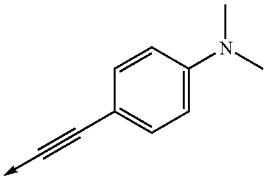 |
| 701 | + | |
| 702 | − | |
| 703 | rac | 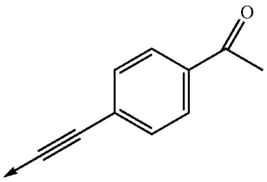 |
| 704 | + | |
| 705 | − | |
| 706 | rac | 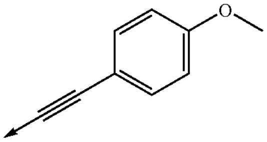 |
| 707 | + | |
| 708 | − | |
| 709 | rac | 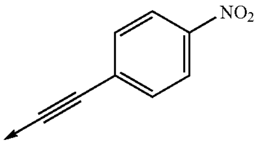 |
| 710 | + | |
| 711 | − | |
-continued
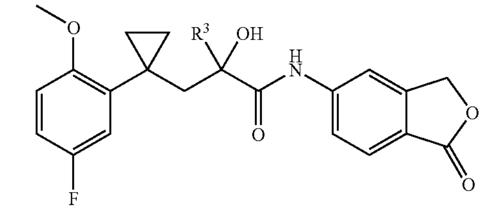
| No. | Racemic or Enantiomer | R3 |
|---|---|---|
| 712 | rac | 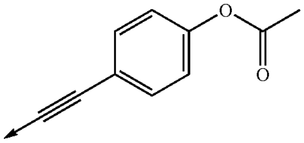 |
| 713 | + | |
| 714 | − | |
| 715 | rac | 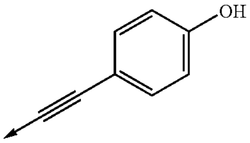 |
| 716 | + | |
| 717 | − | |
| 718 | rac | 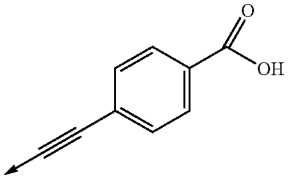 |
| 719 | + | |
| 720 | − | |
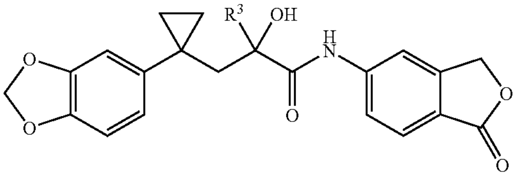
| No. | Racemic or Enantiomer | R3 |
|---|---|---|
| 721 | rac | 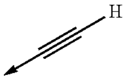 |
| 722 | + | |
| 723 | − | |
| 724 | rac | 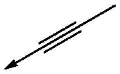 |
| 725 | + | |
| 726 | − | |
| 727 | rac | 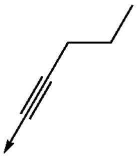 |
| 728 | + | |
| 729 | − | |

-continued
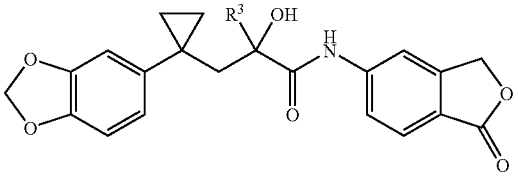
| No. | Racemic or Enantiomer | R3 |
|---|---|---|
| 730 | rac | 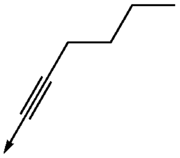 |
| 731 | + | |
| 732 | − | |
| 733 | rac | 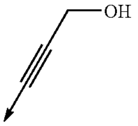 |
| 734 | + | |
| 735 | − | |
| 736 | rac | 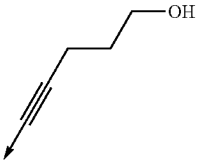 |
| 737 | + | |
| 738 | − | |
| 739 | rac | 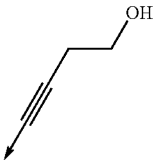 |
| 740 | + | |
| 741 | − | |
| 742 | rac | 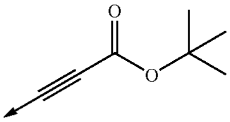 |
| 743 | + | |
| 744 | − | |
| 745 | rac | 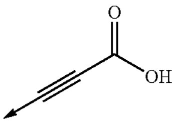 |
| 746 | + | |
| 747 | − | |
| 748 | rac | 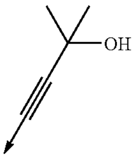 |
| 749 | + | |
| 750 | − | |
| 751 | rac | 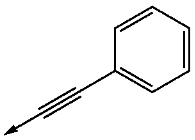 |
| 752 | + | |
| 753 | − | |
-continued
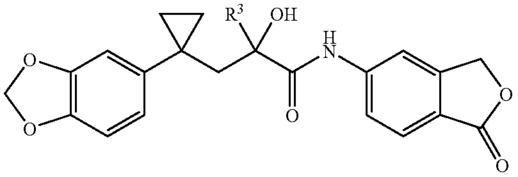
| No. | Racemic or Enantiomer | R3 |
|---|---|---|
| 754 | rac | 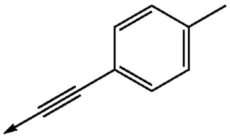 |
| 755 | + | |
| 756 | − | |
| 757 | rac | 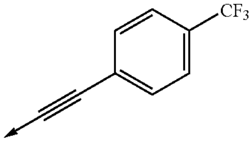 |
| 758 | + | |
| 759 | − | |
| 760 | rac | 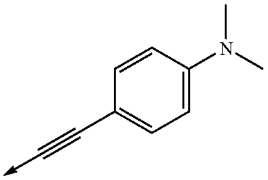 |
| 761 | + | |
| 762 | − | |
| 763 | rac | 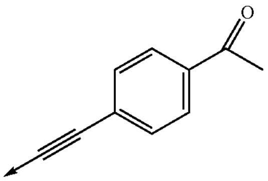 |
| 764 | + | |
| 765 | − | |
| 766 | rac | 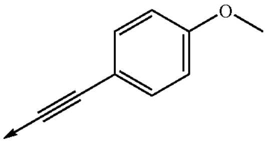 |
| 767 | + | |
| 768 | − | |
| 769 | rac | 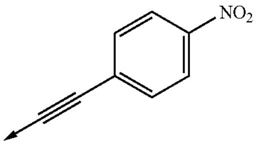 |
| 770 | + | |
| 771 | − | |
| 772 | rac | 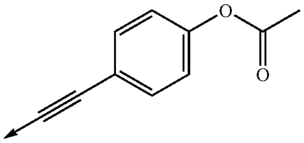 |
| 773 | + | |
| 774 | − | |
| 775 | rac | 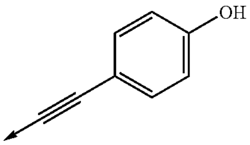 |
| 776 | + | |
| 777 | − | |

-continued
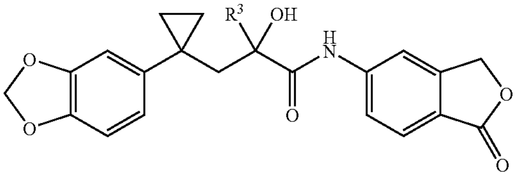
| No. | Racemic or Enantiomer | R3 |
|---|---|---|
| 778 | rac | 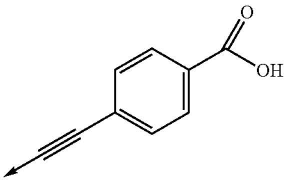 |
| 779 | + | |
| 780 | − | |
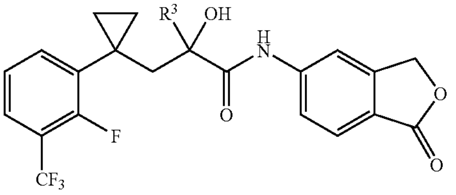
| No. | Racemic or Enantiomer | R3 |
|---|---|---|
| 781 | rac | 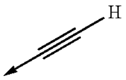 |
| 782 | + | |
| 783 | − | |
| 784 | rac | 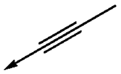 |
| 785 | + | |
| 786 | − | |
| 787 | rac | 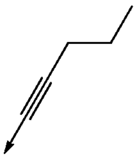 |
| 788 | + | |
| 789 | − | |
| 790 | rac | 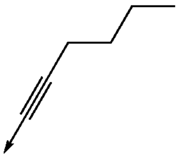 |
| 791 | + | |
| 792 | − | |
| 793 | rac | 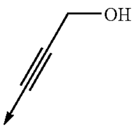 |
| 794 | + | |
| 795 | − | |
-continued
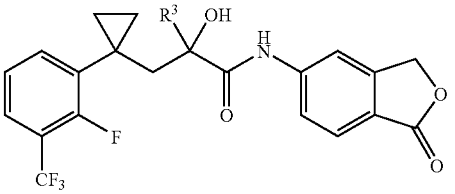
| No. | Racemic or Enantiomer | R3 |
|---|---|---|
| 796 | rac | 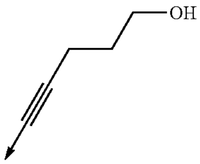 |
| 797 | + | |
| 798 | − | |
| 799 | rac | 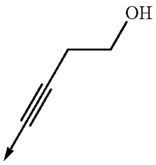 |
| 800 | + | |
| 801 | − | |
| 802 | rac | 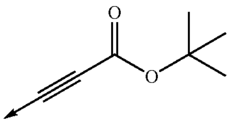 |
| 803 | + | |
| 804 | − | |
| 805 | rac | 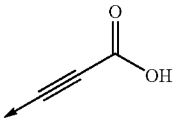 |
| 806 | + | |
| 807 | − | |
| 808 | rac | 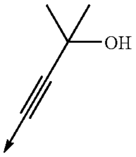 |
| 809 | + | |
| 810 | − | |
| 811 | rac | 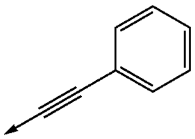 |
| 812 | + | |
| 813 | − | |
| 814 | rac | 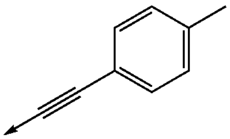 |
| 815 | + | |
| 816 | − | |
| 817 | rac | 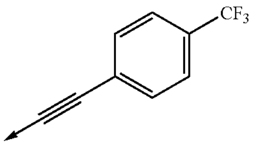 |
| 818 | + | |
| 819 | − | |

-continued
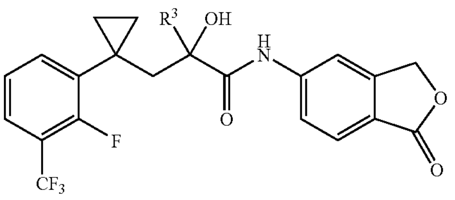
| No. | Racemic or Enantiomer | R3 |
|---|---|---|
| 820 | rac | 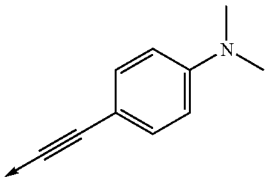 |
| 821 | + | |
| 822 | − | |
| 823 | rac | 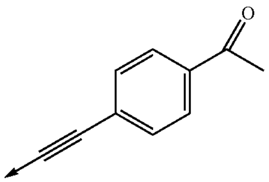 |
| 824 | + | |
| 825 | − | |
| 826 | rac | 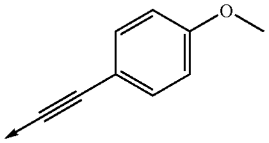 |
| 827 | + | |
| 828 | − | |
| 829 | rac | 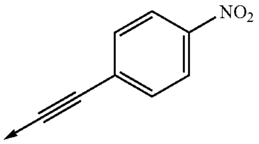 |
| 830 | + | |
| 831 | − | |
| 832 | rac | 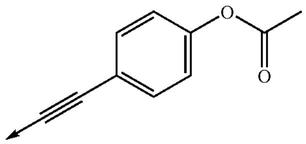 |
| 833 | + | |
| 834 | − | |
| 835 | rac | 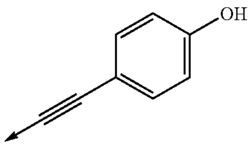 |
| 836 | + | |
| 837 | − | |
| 838 | rac | 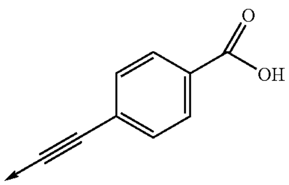 |
| 839 | + | |
| 840 | − | |
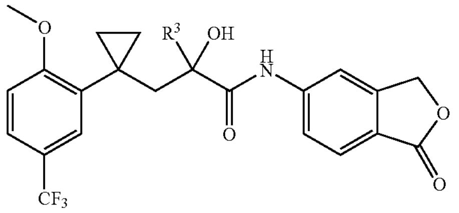
| No. | Racemic or Enantiomer | R3 |
|---|---|---|
| 841 | rac | 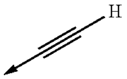 |
| 842 | + | |
| 843 | − | |
| 844 | rac | 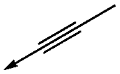 |
| 845 | + | |
| 846 | − | |
| 847 | rac | 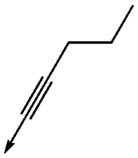 |
| 848 | + | |
| 849 | − | |
| 850 | rac | 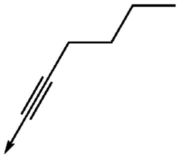 |
| 851 | + | |
| 852 | − | |
| 853 | rac | 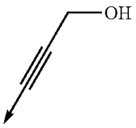 |
| 854 | + | |
| 855 | − | |
| 856 | rac | 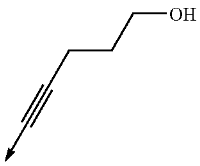 |
| 857 | + | |
| 858 | − | |
| 859 | rac | 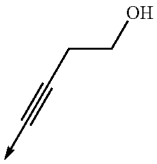 |
| 860 | + | |
| 861 | − | |
| 862 | rac | 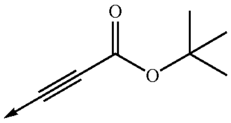 |
| 863 | + | |
| 864 | − | |
| 865 | rac | 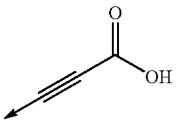 |
| 866 | + | |
| 867 | − | |

-continued
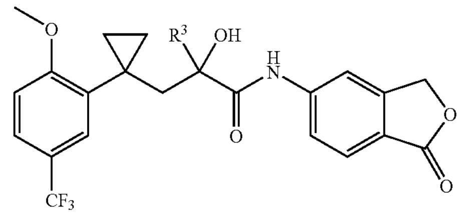
| No. | Racemic or Enantiomer | R3 |
|---|---|---|
| 868 | rac | 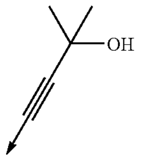 |
| 869 | + | |
| 870 | − | |
| 871 | rac | 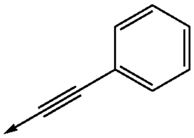 |
| 872 | + | |
| 873 | − | |
| 874 | rac | 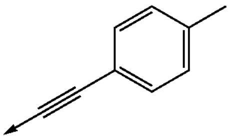 |
| 875 | + | |
| 876 | − | |
| 877 | rac | 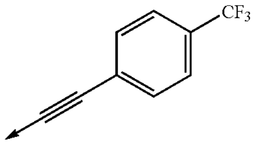 |
| 878 | + | |
| 879 | − | |
| 880 | rac | 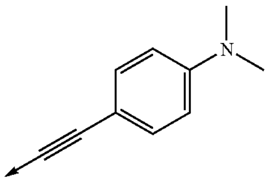 |
| 881 | + | |
| 882 | − | |
| 883 | rac | 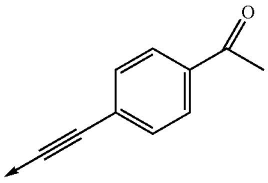 |
| 884 | + | |
| 885 | − | |
| 886 | rac | 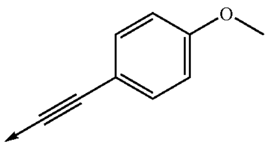 |
| 887 | + | |
| 888 | − | |
| 889 | rac | 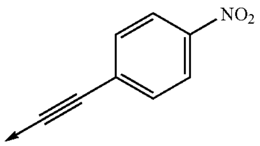 |
| 890 | + | |
| 891 | − | |
-continued
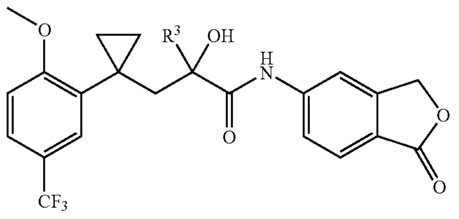
| No. | Racemic or Enantiomer | R3 |
|---|---|---|
| 892 | rac | 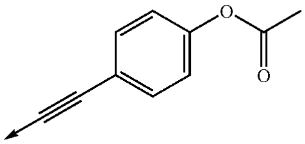 |
| 893 | + | |
| 894 | − | |
| 895 | rac | 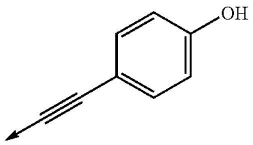 |
| 896 | + | |
| 897 | − | |
| 898 | rac | 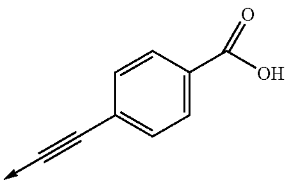 |
| 899 | + | |
| 900 | − | |
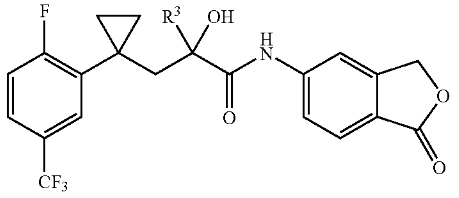
| No. | Racemic or Enantiomer | R3 |
|---|---|---|
| 901 | rac | 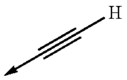 |
| 902 | + | |
| 903 | − | |
| 904 | rac | 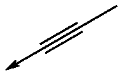 |
| 905 | + | |
| 906 | − | |
| 907 | rac | 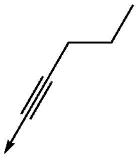 |
| 908 | + | |
| 909 | − | |

-continued

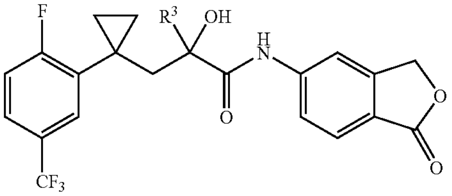

| No. | Racemic or Enantiomer | R3 |
|---|---|---|
| 910<br>911<br>912 | rac<br>+<br>– | 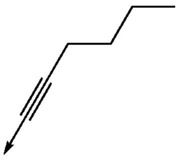 |
| 913<br>914<br>915 | rac<br>+<br>– | 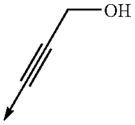 |
| 916<br>917<br>918 | rac<br>+<br>– | 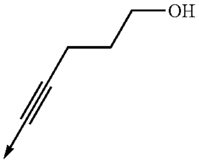 |
| 919<br>920<br>921 | rac<br>+<br>– | 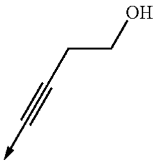 |
| 922<br>923<br>924 | rac<br>+<br>– | 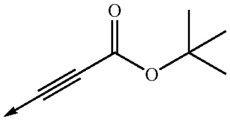 |
| 925<br>926<br>927 | rac<br>+<br>– | 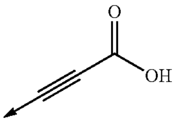 |
| 928<br>929<br>930 | rac<br>+<br>– | 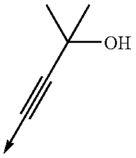 |
| 931<br>932<br>933 | rac<br>+<br>– | 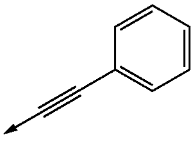 |

-continued

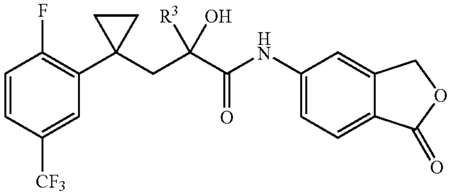

| No. | Racemic or Enantiomer | R3 |
|---|---|---|
| 934<br>935<br>936 | rac<br>+<br>– | 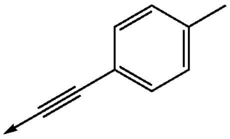 |
| 937<br>938<br>939 | rac<br>+<br>– | 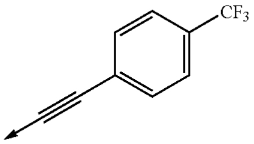 |
| 940<br>941<br>942 | rac<br>+<br>– | 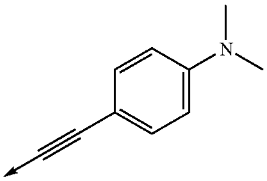 |
| 943<br>944<br>945 | rac<br>+<br>– | 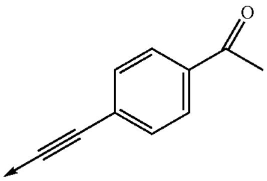 |
| 946<br>947<br>948 | rac<br>+<br>– | 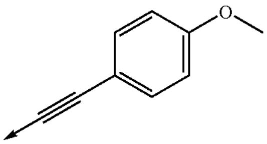 |
| 949<br>950<br>951 | rac<br>+<br>– | 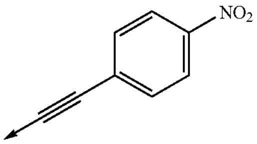 |
| 952<br>953<br>954 | rac<br>+<br>– | 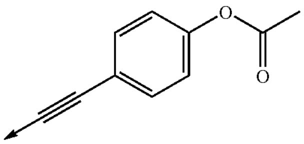 |
| 955<br>956<br>957 | rac<br>+<br>– | 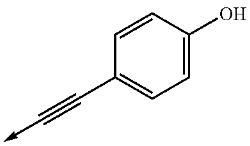 |

-continued
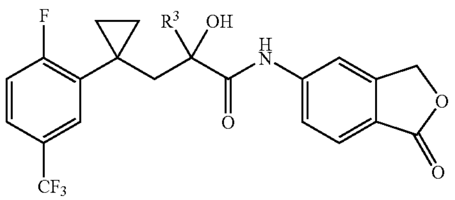
| No. | Racemic or Enantiomer | R3 |
|---|---|---|
| 958 | rac | 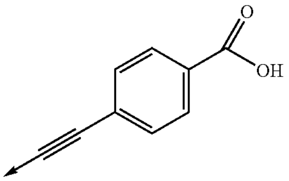 |
| 959 | + | |
| 960 | − | |
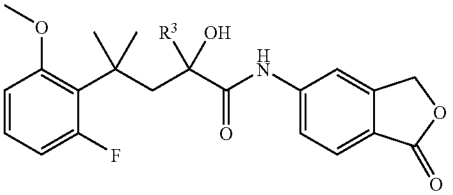
| No. | Racemic or Enantiomer | R3 |
|---|---|---|
| 961 | rac | 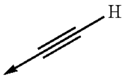 |
| 962 | + | |
| 963 | − | |
| 964 | rac | 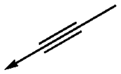 |
| 965 | + | |
| 966 | − | |
| 967 | rac | 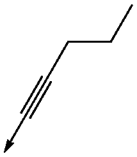 |
| 968 | + | |
| 969 | − | |
| 970 | rac | 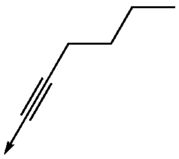 |
| 971 | + | |
| 972 | − | |
| 973 | rac | 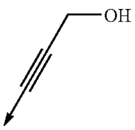 |
| 974 | + | |
| 975 | − | |
-continued
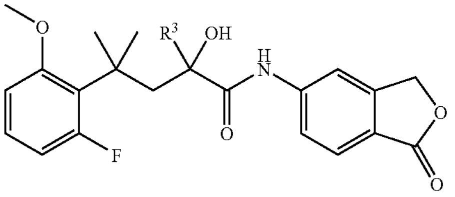
| No. | Racemic or Enantiomer | R3 |
|---|---|---|
| 976 | rac | 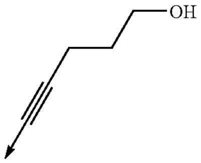 |
| 977 | + | |
| 978 | − | |
| 979 | rac | 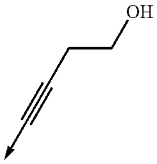 |
| 980 | + | |
| 981 | − | |
| 982 | rac | 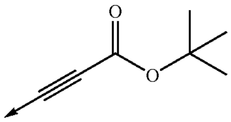 |
| 983 | + | |
| 984 | − | |
| 985 | rac | 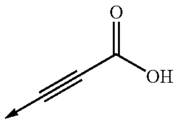 |
| 986 | + | |
| 987 | − | |
| 988 | rac | 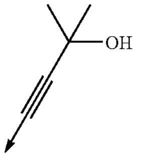 |
| 989 | + | |
| 990 | − | |
| 991 | rac | 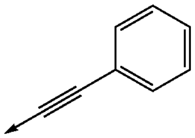 |
| 992 | + | |
| 993 | − | |
| 994 | rac | 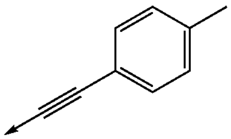 |
| 995 | + | |
| 996 | − | |
| 997 | rac | 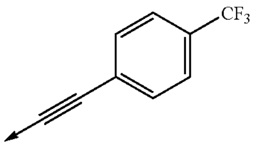 |
| 998 | + | |
| 999 | − | |

-continued
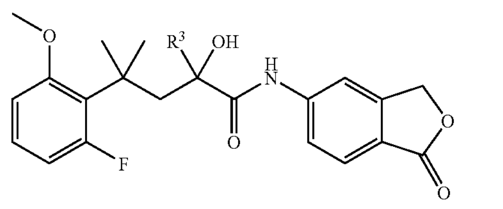
| No. | Racemic or Enantiomer | R3 |
|---|---|---|
| 1000 | rac | 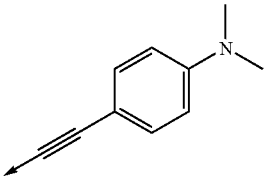 |
| 1001 | + | |
| 1002 | − | |
| 1003 | rac | 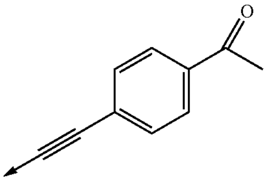 |
| 1004 | + | |
| 1005 | − | |
| 1006 | rac | 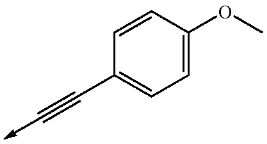 |
| 1007 | + | |
| 1008 | − | |
| 1009 | rac | 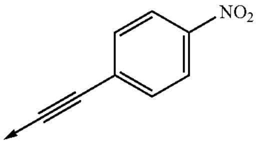 |
| 1010 | + | |
| 1011 | − | |
| 1012 | rac | 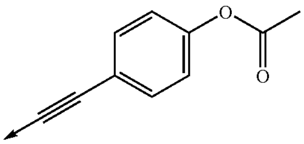 |
| 1013 | + | |
| 1014 | − | |
| 1015 | rac | 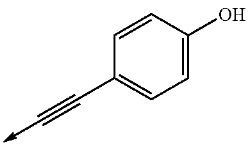 |
| 1016 | + | |
| 1017 | − | |
| 1018 | rac | 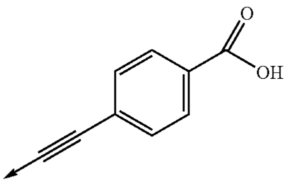 |
| 1019 | + | |
| 1020 | − | |
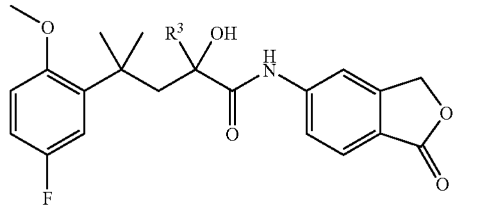
| No. | Racemic or Enantiomer | R3 |
|---|---|---|
| 1021 | rac | 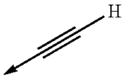 |
| 1022 | + | |
| 1023 | − | |
| 1024 | rac | 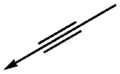 |
| 1025 | + | |
| 1026 | − | |
| 1027 | rac | 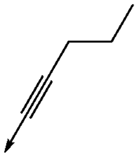 |
| 1028 | + | |
| 1029 | − | |
| 1030 | rac | 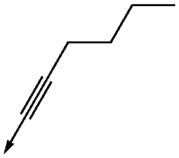 |
| 1031 | + | |
| 1032 | − | |
| 1033 | rac | 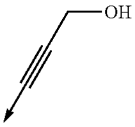 |
| 1034 | + | |
| 1035 | − | |
| 1036 | rac | 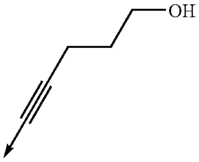 |
| 1037 | + | |
| 1038 | − | |
| 1039 | rac | 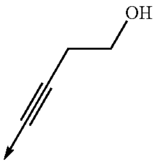 |
| 1040 | + | |
| 1041 | − | |
| 1042 | rac | 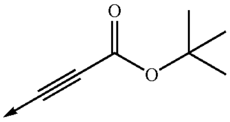 |
| 1043 | + | |
| 1044 | − | |
| 1045 | rac | 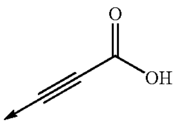 |
| 1046 | + | |
| 1047 | − | |

-continued
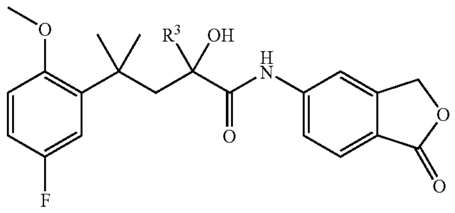
| No. | Racemic or Enantiomer | R3 |
|---|---|---|
| 1048 | rac | 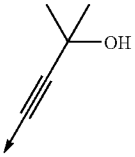 |
| 1049 | + | |
| 1050 | − | |
| 1051 | rac | 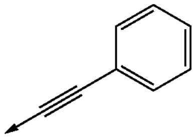 |
| 1052 | + | |
| 1053 | − | |
| 1054 | rac | 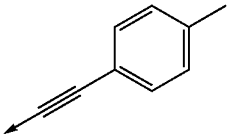 |
| 1055 | + | |
| 1056 | − | |
| 1057 | rac | 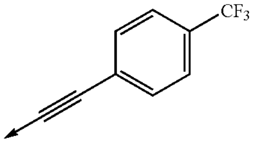 |
| 1058 | + | |
| 1059 | − | |
| 1060 | rac | 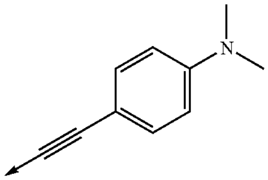 |
| 1061 | + | |
| 1062 | − | |
| 1063 | rac | 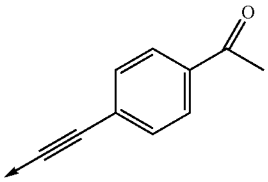 |
| 1064 | + | |
| 1065 | − | |
| 1066 | rac | 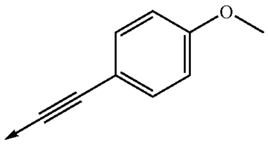 |
| 1067 | + | |
| 1068 | − | |
| 1069 | rac | 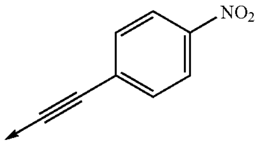 |
| 1070 | + | |
| 1071 | − | |
-continued
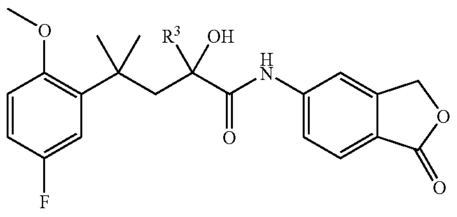
| No. | Racemic or Enantiomer | R3 |
|---|---|---|
| 1072 | rac | 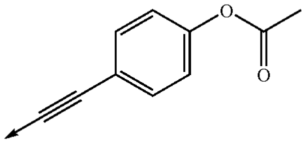 |
| 1073 | + | |
| 1074 | − | |
| 1075 | rac | 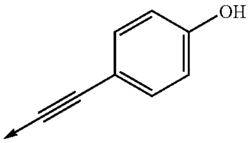 |
| 1076 | + | |
| 1077 | − | |
| 1078 | rac | 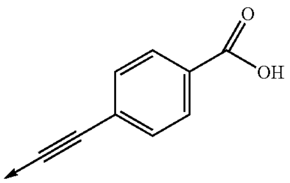 |
| 1079 | + | |
| 1080 | − | |
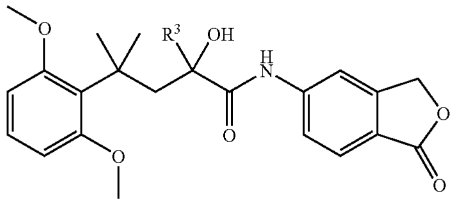
| No. | Racemic or Enantiomer | R3 |
|---|---|---|
| 1081 | rac | 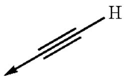 |
| 1082 | + | |
| 1083 | − | |
| 1084 | rac | 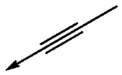 |
| 1085 | + | |
| 1086 | − | |
| 1087 | rac | 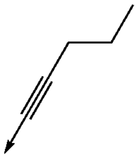 |
| 1088 | + | |
| 1089 | − | |

-continued
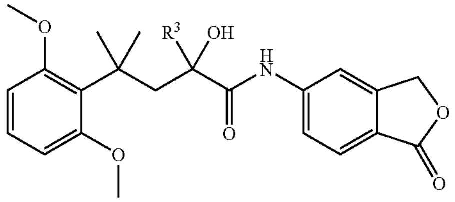
| No. | Racemic or Enantiomer | R3 |
|---|---|---|
| 1090 | rac | 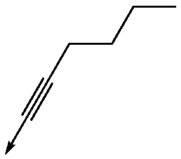 |
| 1091 | + | |
| 1092 | − | |
| 1093 | rac | 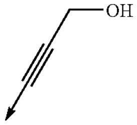 |
| 1094 | + | |
| 1095 | − | |
| 1096 | rac | 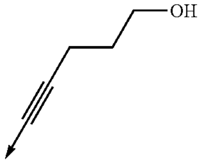 |
| 1097 | + | |
| 1098 | − | |
| 1099 | rac | 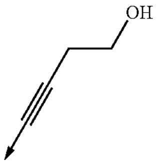 |
| 1100 | + | |
| 1101 | − | |
| 1102 | rac | 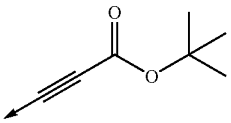 |
| 1103 | + | |
| 1104 | − | |
| 1105 | rac | 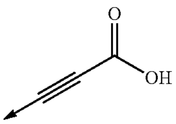 |
| 1106 | + | |
| 1107 | − | |
| 1108 | rac | 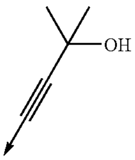 |
| 1109 | + | |
| 1110 | − | |
| 1111 | rac | 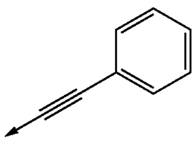 |
| 1112 | + | |
| 1113 | − | |
-continued
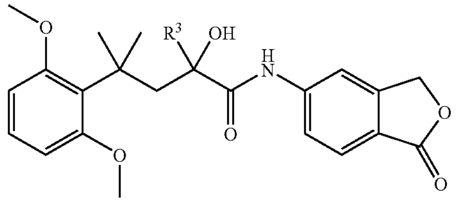
| No. | Racemic or Enantiomer | R3 |
|---|---|---|
| 1114 | rac | 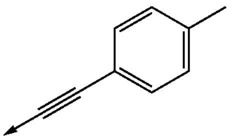 |
| 1115 | + | |
| 1116 | − | |
| 1117 | rac | 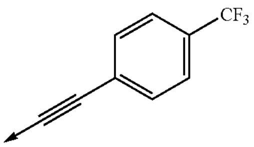 |
| 1118 | + | |
| 1119 | − | |
| 1120 | rac | 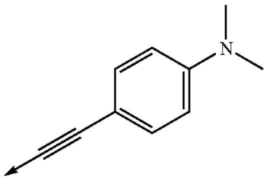 |
| 1121 | + | |
| 1122 | − | |
| 1123 | rac | 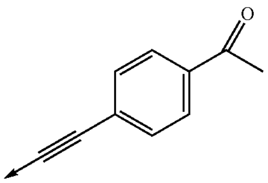 |
| 1124 | + | |
| 1125 | − | |
| 1126 | rac | 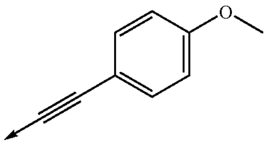 |
| 1127 | + | |
| 1128 | − | |
| 1129 | rac | 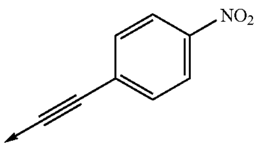 |
| 1130 | + | |
| 1131 | − | |
| 1132 | rac | 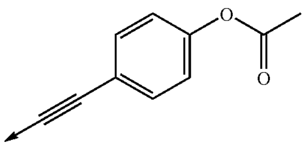 |
| 1133 | + | |
| 1134 | − | |
| 1135 | rac | 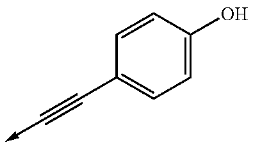 |
| 1136 | + | |
| 1137 | − | |

-continued

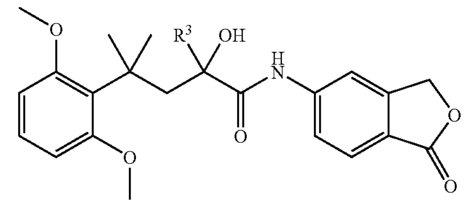

| No. | Racemic or Enantiomer | R3 |
|---|---|---|
| 1138<br>1139<br>1140 | rac<br>+<br>− | 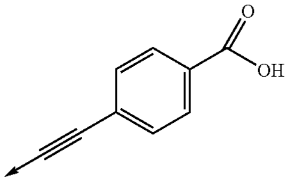 |

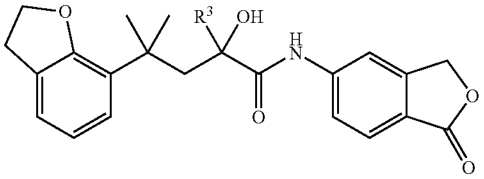

| No. | Racemic or Enantiomer | R3 |
|---|---|---|
| 1141<br>1142<br>1143 | rac<br>+<br>− | 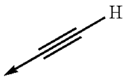 |
| 1144<br>1145<br>1146 | rac<br>+<br>− | 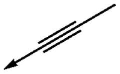 |
| 1147<br>1148<br>1149 | rac<br>+<br>− | 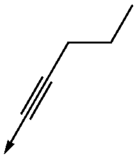 |
| 1150<br>1151<br>1152 | rac<br>+<br>− | 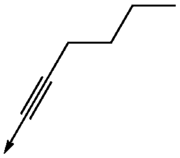 |
| 1153<br>1154<br>1155 | rac<br>+<br>− | 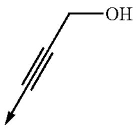 |

-continued

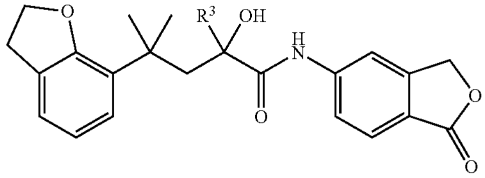

| No. | Racemic or Enantiomer | R3 |
|---|---|---|
| 1156<br>1157<br>1158 | rac<br>+<br>− | 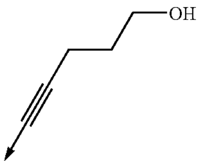 |
| 1159<br>1160<br>1161 | rac<br>+<br>− | 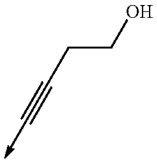 |
| 1162<br>1163<br>1164 | rac<br>+<br>− | 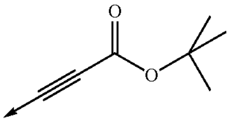 |
| 1165<br>1166<br>1167 | rac<br>+<br>− | 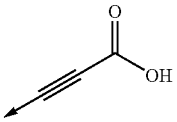 |
| 1168<br>1169<br>1170 | rac<br>+<br>− | 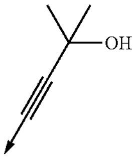 |
| 1171<br>1172<br>1173 | rac<br>+<br>− | 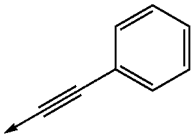 |
| 1174<br>1175<br>1176 | rac<br>+<br>− | 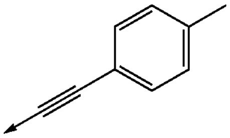 |
| 1177<br>1178<br>1179 | rac<br>+<br>− | 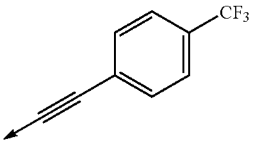 |

-continued
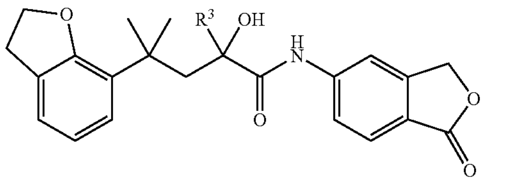
| No. | Racemic or Enantiomer | R3 |
|---|---|---|
| 1180 | rac | 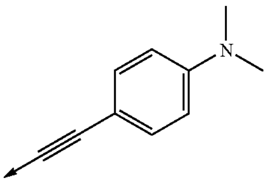 |
| 1181 | + | |
| 1182 | − | |
| 1183 | rac | 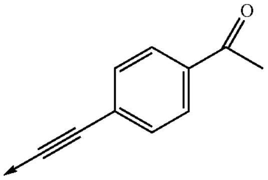 |
| 1184 | + | |
| 1185 | − | |
| 1186 | rac | 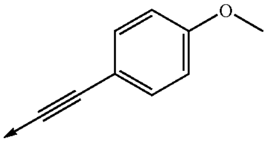 |
| 1187 | + | |
| 1188 | − | |
| 1189 | rac | 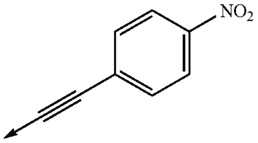 |
| 1190 | + | |
| 1191 | − | |
| 1192 | rac | 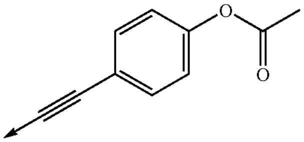 |
| 1193 | + | |
| 1194 | − | |
| 1195 | rac | 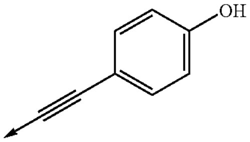 |
| 1196 | + | |
| 1197 | − | |
| 1198 | rac | 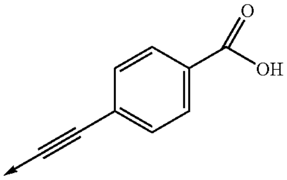 |
| 1199 | + | |
| 1200 | − | |
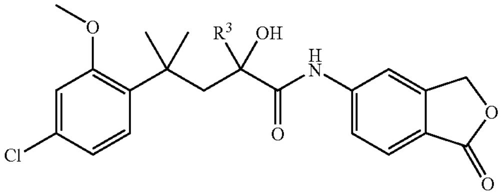
| No. | Racemic or Enantiomer | R3 |
|---|---|---|
| 1201 | rac | 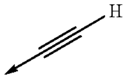 |
| 1202 | + | |
| 1203 | − | |
| 1204 | rac | 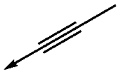 |
| 1205 | + | |
| 1206 | − | |
| 1207 | rac | 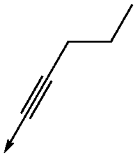 |
| 1208 | + | |
| 1209 | − | |
| 1210 | rac | 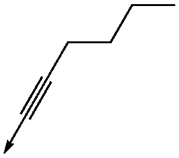 |
| 1211 | + | |
| 1212 | − | |
| 1213 | rac | 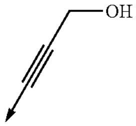 |
| 1214 | + | |
| 1215 | − | |
| 1216 | rac | 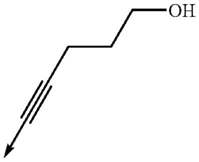 |
| 1217 | + | |
| 1218 | − | |
| 1219 | rac | 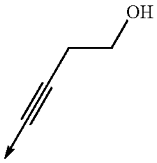 |
| 1220 | + | |
| 1221 | − | |
| 1222 | rac | 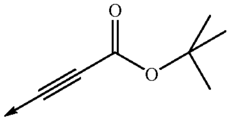 |
| 1223 | + | |
| 1224 | − | |
| 1225 | rac | 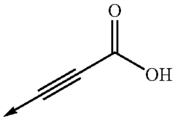 |
| 1226 | + | |
| 1227 | − | |

-continued
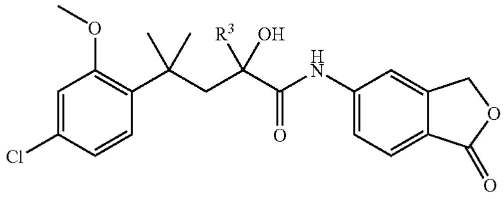
| No. | Racemic or Enantiomer | R3 |
|---|---|---|
| 1228 | rac | 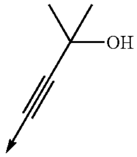 |
| 1229 | + | |
| 1230 | − | |
| 1231 | rac | 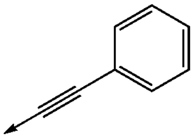 |
| 1232 | + | |
| 1233 | − | |
| 1234 | rac | 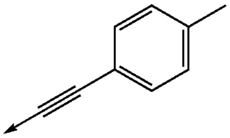 |
| 1235 | + | |
| 1236 | − | |
| 1237 | rac | 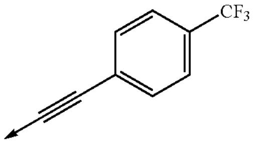 |
| 1238 | + | |
| 1239 | − | |
| 1240 | rac | 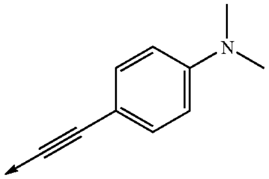 |
| 1241 | + | |
| 1242 | − | |
| 1243 | rac | 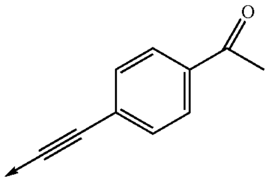 |
| 1244 | + | |
| 1245 | − | |
| 1246 | rac | 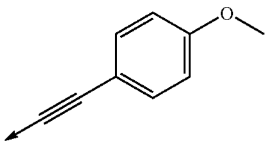 |
| 1247 | + | |
| 1248 | − | |
| 1249 | rac | 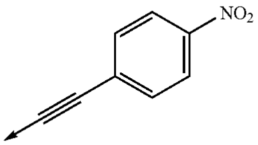 |
| 1250 | + | |
| 1251 | − | |
-continued
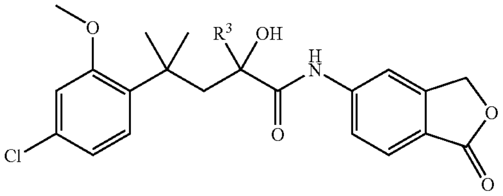
| No. | Racemic or Enantiomer | R3 |
|---|---|---|
| 1252 | rac | 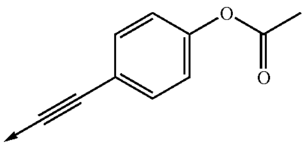 |
| 1253 | + | |
| 1254 | − | |
| 1255 | rac | 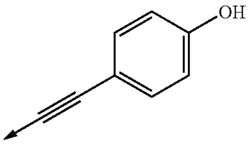 |
| 1256 | + | |
| 1257 | − | |
| 1258 | rac | 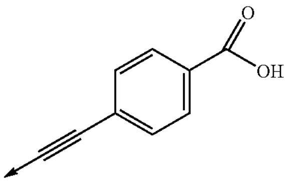 |
| 1259 | + | |
| 1260 | − | |
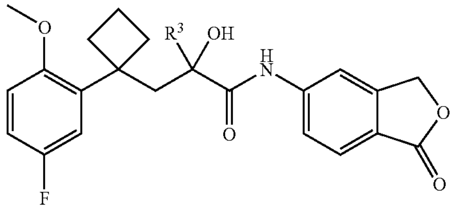
| No. | Racemic or Enantiomer | R3 |
|---|---|---|
| 1261 | rac | 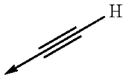 |
| 1262 | + | |
| 1263 | − | |
| 1264 | rac | 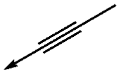 |
| 1265 | + | |
| 1266 | − | |
| 1267 | rac | 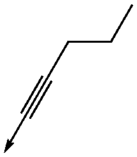 |
| 1268 | + | |
| 1269 | − | |

-continued
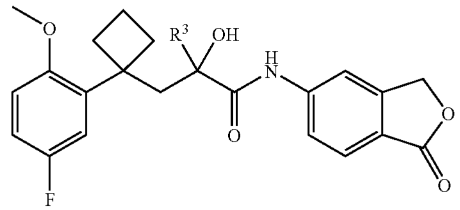
| No. | Racemic or Enantiomer | R3 |
|---|---|---|
| 1270 | rac | 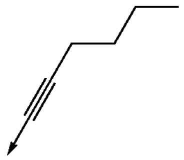 |
| 1271 | + | |
| 1272 | – | |
| 1273 | rac | 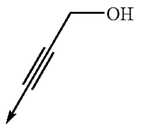 |
| 1274 | + | |
| 1275 | – | |
| 1276 | rac | 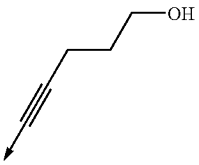 |
| 1277 | + | |
| 1278 | – | |
| 1279 | rac | 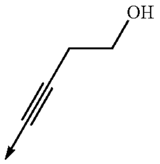 |
| 1280 | + | |
| 1281 | – | |
| 1282 | rac | 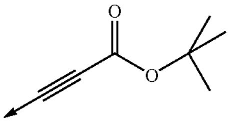 |
| 1283 | + | |
| 1284 | – | |
| 1285 | rac | 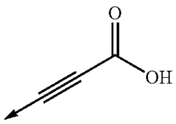 |
| 1286 | + | |
| 1287 | – | |
| 1288 | rac | 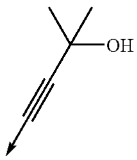 |
| 1289 | + | |
| 1290 | – | |
| 1291 | rac | 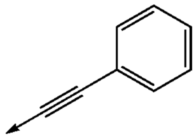 |
| 1292 | + | |
| 1293 | – | |
-continued
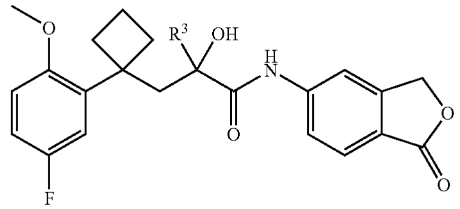
| No. | Racemic or Enantiomer | R3 |
|---|---|---|
| 1294 | rac | 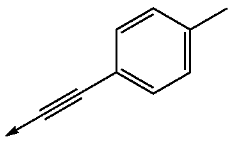 |
| 1295 | + | |
| 1296 | – | |
| 1297 | rac | 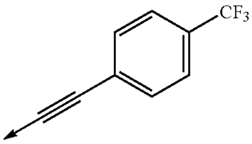 |
| 1298 | + | |
| 1299 | – | |
| 1300 | rac | 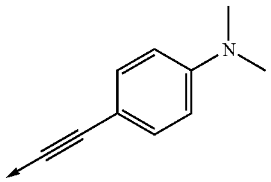 |
| 1301 | + | |
| 1302 | – | |
| 1303 | rac | 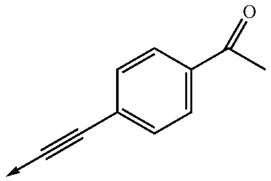 |
| 1304 | + | |
| 1305 | – | |
| 1306 | rac | 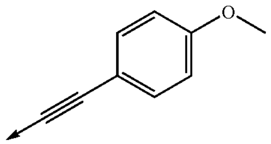 |
| 1307 | + | |
| 1308 | – | |
| 1309 | rac | 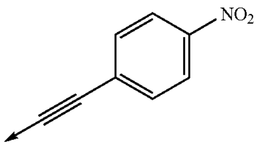 |
| 1310 | + | |
| 1311 | – | |
| 1312 | rac | 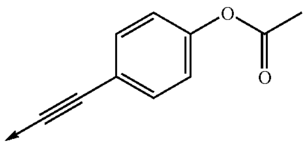 |
| 1313 | + | |
| 1314 | – | |
| 1315 | rac | 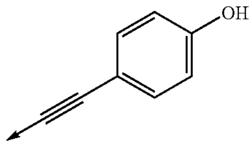 |
| 1316 | + | |
| 1317 | – | |

-continued
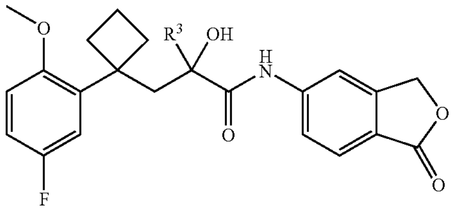
| No. | Racemic or Enantiomer | R3 |
|---|---|---|
| 1318 | rac | 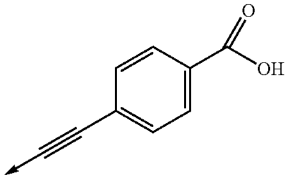 |
| 1319 | + | |
| 1320 | − | |
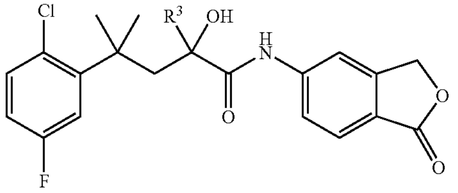
| No. | Racemic or Enantiomer | R3 |
|---|---|---|
| 1321 | rac | 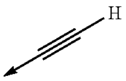 |
| 1322 | + | |
| 1323 | − | |
| 1324 | rac | 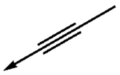 |
| 1325 | + | |
| 1326 | − | |
| 1327 | rac | 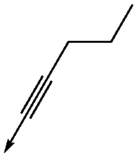 |
| 1328 | + | |
| 1329 | − | |
| 1330 | rac | 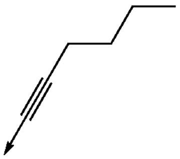 |
| 1331 | + | |
| 1332 | − | |
| 1333 | rac | 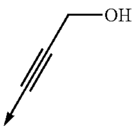 |
| 1334 | + | |
| 1335 | − | |
-continued
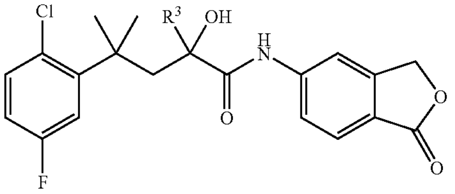
| No. | Racemic or Enantiomer | R3 |
|---|---|---|
| 1336 | rac | 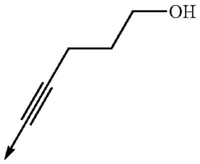 |
| 1337 | + | |
| 1338 | − | |
| 1339 | rac | 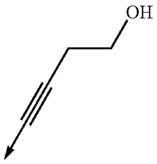 |
| 1340 | + | |
| 1341 | − | |
| 1342 | rac | 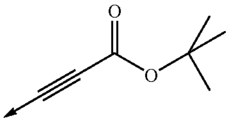 |
| 1343 | + | |
| 1344 | − | |
| 1345 | rac | 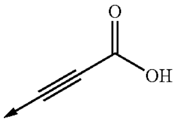 |
| 1346 | + | |
| 1347 | − | |
| 1348 | rac | 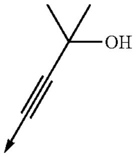 |
| 1349 | + | |
| 1350 | − | |
| 1351 | rac | 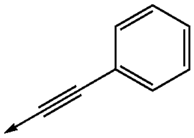 |
| 1352 | + | |
| 1353 | − | |
| 1354 | rac | 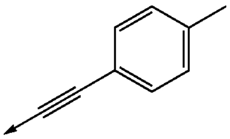 |
| 1355 | + | |
| 1356 | − | |
| 1357 | rac | 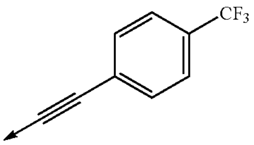 |
| 1358 | + | |
| 1359 | − | |

-continued
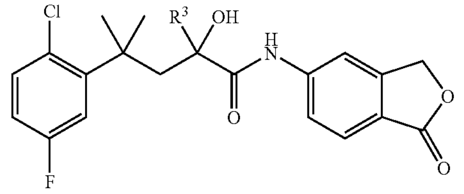
| No. | Racemic or Enantiomer | R3 |
|---|---|---|
| 1360 | rac | 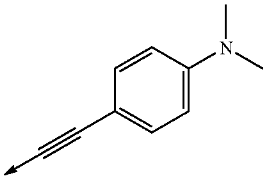 |
| 1361 | + | |
| 1362 | − | |
| 1363 | rac | 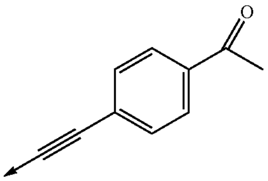 |
| 1364 | + | |
| 1365 | − | |
| 1366 | rac | 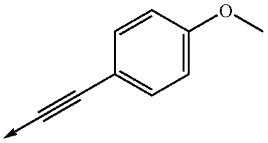 |
| 1367 | + | |
| 1368 | − | |
| 1369 | rac | 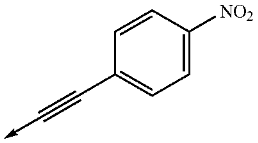 |
| 1370 | + | |
| 1371 | − | |
| 1372 | rac | 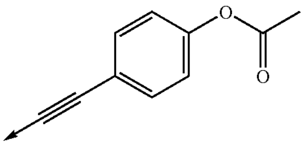 |
| 1373 | + | |
| 1374 | − | |
| 1375 | rac | 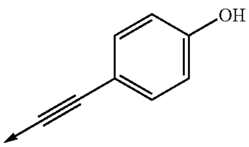 |
| 1376 | + | |
| 1377 | − | |
| 1378 | rac | 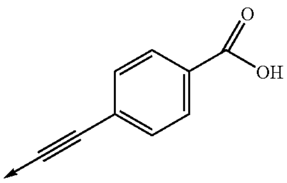 |
| 1379 | + | |
| 1380 | − | |
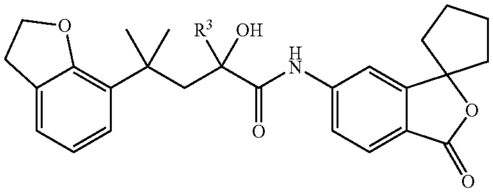
| No. | Racemic or Enantiomer | R3 |
|---|---|---|
| 1381 | rac | 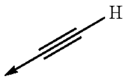 |
| 1382 | + | |
| 1383 | − | |
| 1384 | rac | 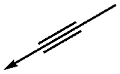 |
| 1385 | + | |
| 1386 | − | |
| 1387 | rac | 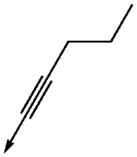 |
| 1388 | + | |
| 1389 | − | |
| 1390 | rac | 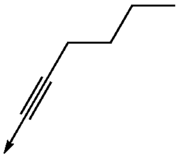 |
| 1391 | + | |
| 1392 | − | |
| 1393 | rac | 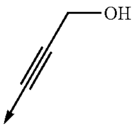 |
| 1394 | + | |
| 1395 | − | |
| 1396 | rac | 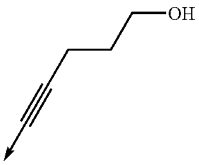 |
| 1397 | + | |
| 1398 | − | |
| 1399 | rac | 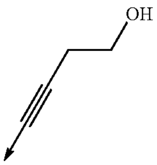 |
| 1400 | + | |
| 1401 | − | |
| 1402 | rac | 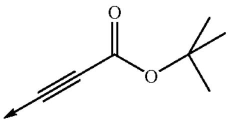 |
| 1403 | + | |
| 1404 | − | |
| 1405 | rac | 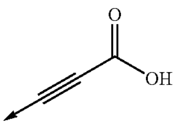 |
| 1406 | + | |
| 1407 | − | |

-continued
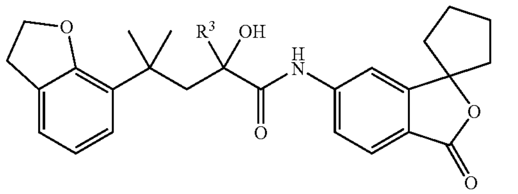
| No. | Racemic or Enantiomer | R3 |
|---|---|---|
| 1408 | rac | 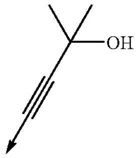 |
| 1409 | + | |
| 1410 | − | |
| 1411 | rac | 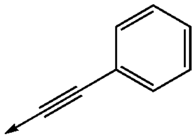 |
| 1412 | + | |
| 1413 | − | |
| 1414 | rac | 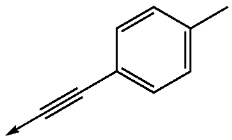 |
| 1415 | + | |
| 1416 | − | |
| 1417 | rac | 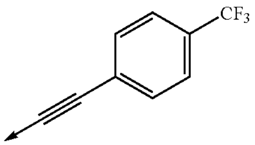 |
| 1418 | + | |
| 1419 | − | |
| 1420 | rac | 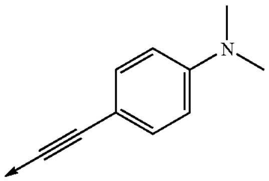 |
| 1421 | + | |
| 1422 | − | |
| 1423 | rac | 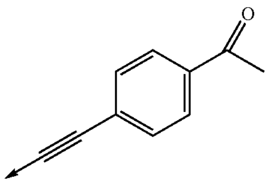 |
| 1424 | + | |
| 1425 | − | |
| 1426 | rac | 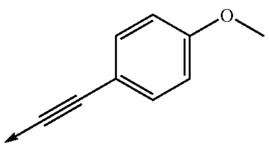 |
| 1427 | + | |
| 1428 | − | |
| 1429 | rac | 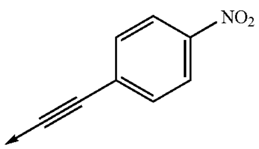 |
| 1430 | + | |
| 1431 | − | |
-continued
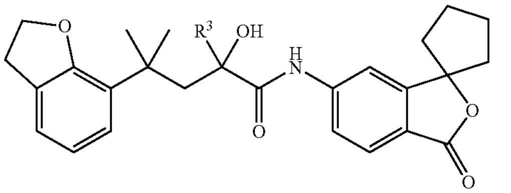
| No. | Racemic or Enantiomer | R3 |
|---|---|---|
| 1432 | rac | 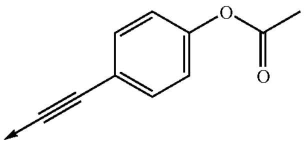 |
| 1433 | + | |
| 1434 | − | |
| 1435 | rac | 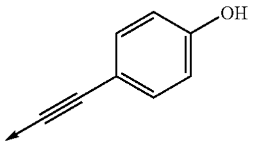 |
| 1436 | + | |
| 1437 | − | |
| 1438 | rac | 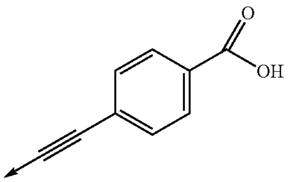 |
| 1439 | + | |
| 1440 | − | |
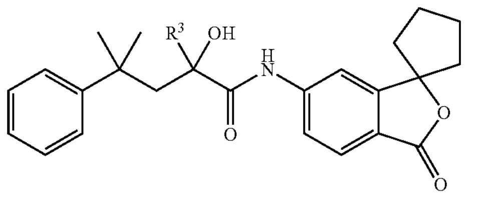
| No. | Racemic or Enantiomer | R3 |
|---|---|---|
| 1441 | rac | 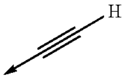 |
| 1442 | + | |
| 1443 | − | |
| 1444 | rac | 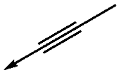 |
| 1445 | + | |
| 1446 | − | |
| 1447 | rac | 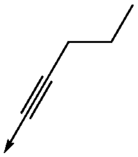 |
| 1448 | + | |
| 1449 | − | |

-continued
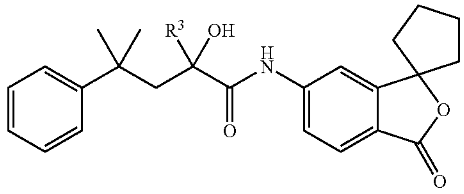
| No. | Racemic or Enantiomer | R3 |
|---|---|---|
| 1450 | rac | 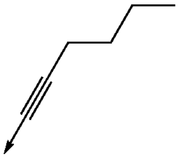 |
| 1451 | + | |
| 1452 | − | |
| 1453 | rac | 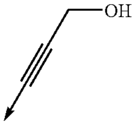 |
| 1454 | + | |
| 1455 | − | |
| 1456 | rac | 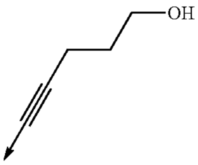 |
| 1457 | + | |
| 1458 | − | |
| 1459 | rac | 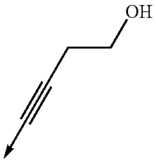 |
| 1460 | + | |
| 1461 | − | |
| 1462 | rac | 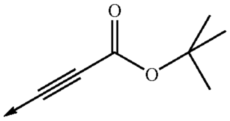 |
| 1463 | + | |
| 1464 | − | |
| 1465 | rac | 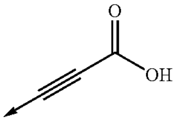 |
| 1466 | + | |
| 1467 | − | |
| 1468 | rac | 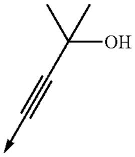 |
| 1469 | + | |
| 1470 | − | |
| 1471 | rac | 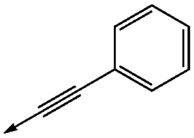 |
| 1472 | + | |
| 1473 | − | |
-continued
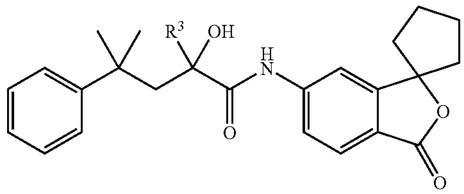
| No. | Racemic or Enantiomer | R3 |
|---|---|---|
| 1474 | rac | 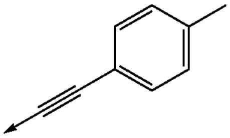 |
| 1475 | + | |
| 1476 | − | |
| 1477 | rac | 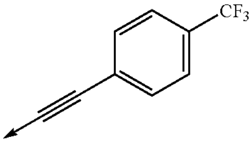 |
| 1478 | + | |
| 1479 | − | |
| 1480 | rac | 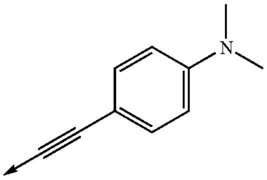 |
| 1481 | + | |
| 1482 | − | |
| 1483 | rac | 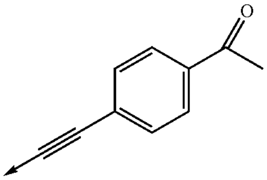 |
| 1484 | + | |
| 1485 | − | |
| 1486 | rac | 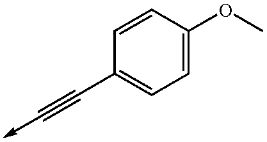 |
| 1487 | + | |
| 1488 | − | |
| 1489 | rac | 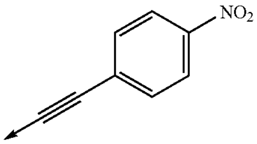 |
| 1490 | + | |
| 1491 | − | |
| 1492 | rac | 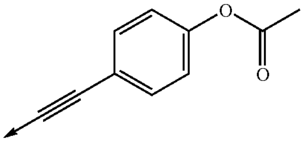 |
| 1493 | + | |
| 1494 | − | |
| 1495 | rac | 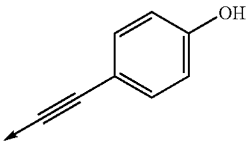 |
| 1496 | + | |
| 1497 | − | |

-continued
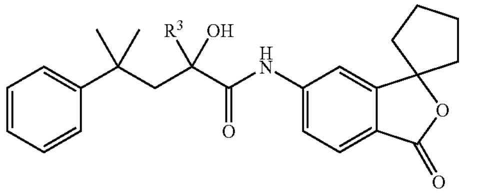
| No. | Racemic or Enantiomer | R3 |
| --- | --- | --- |
| 1498 | rac | 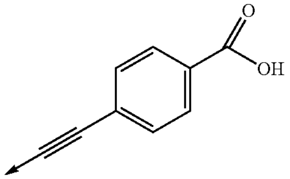 |
| 1499 | + | |
| 1500 | − | |
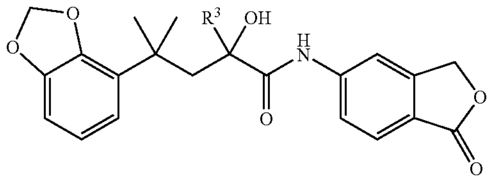
| No. | Racemic or Enantiomer | R3 |
| --- | --- | --- |
| 1501 | rac | 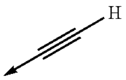 |
| 1502 | + | |
| 1503 | − | |
| 1504 | rac | 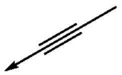 |
| 1505 | + | |
| 1506 | − | |
| 1507 | rac | 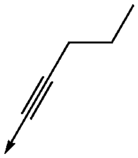 |
| 1508 | + | |
| 1509 | − | |
| 1510 | rac | 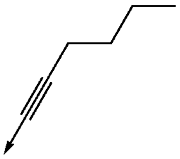 |
| 1511 | + | |
| 1512 | − | |
| 1513 | rac | 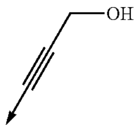 |
| 1514 | + | |
| 1515 | − | |
-continued
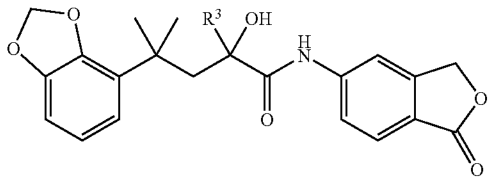
| No. | Racemic or Enantiomer | R3 |
| --- | --- | --- |
| 1516 | rac | 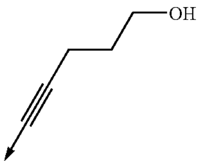 |
| 1517 | + | |
| 1518 | − | |
| 1519 | rac | 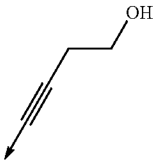 |
| 1520 | + | |
| 1521 | − | |
| 1522 | rac | 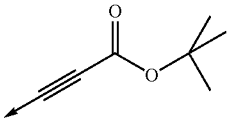 |
| 1523 | + | |
| 1524 | − | |
| 1525 | rac | 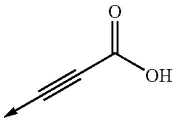 |
| 1526 | + | |
| 1527 | − | |
| 1528 | rac | 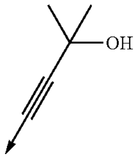 |
| 1529 | + | |
| 1530 | − | |
| 1531 | rac | 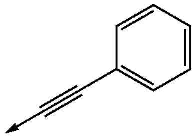 |
| 1532 | + | |
| 1533 | − | |
| 1534 | rac | 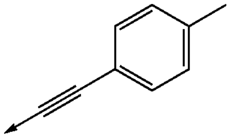 |
| 1535 | + | |
| 1536 | − | |
| 1537 | rac | 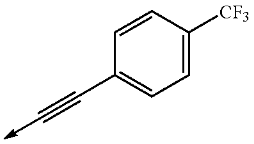 |
| 1538 | + | |
| 1539 | − | |

-continued
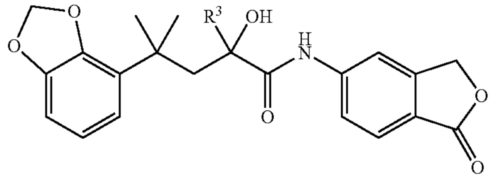
| No. | Racemic or Enantiomer | R3 |
|---|---|---|
| 1540 | rac | 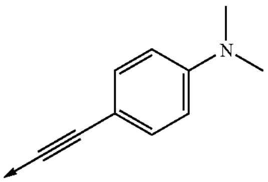 |
| 1541 | + | |
| 1542 | − | |
| 1543 | rac | 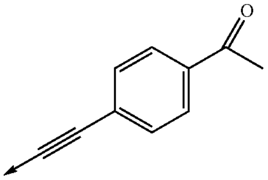 |
| 1544 | + | |
| 1545 | − | |
| 1546 | rac | 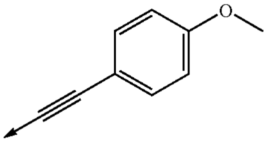 |
| 1547 | + | |
| 1548 | − | |
| 1549 | rac | 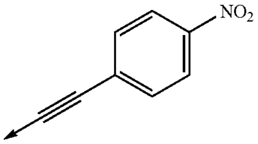 |
| 1550 | + | |
| 1551 | − | |
| 1552 | rac | 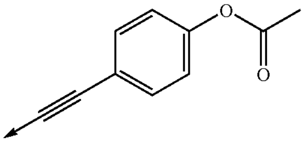 |
| 1553 | + | |
| 1554 | − | |
| 1555 | rac | 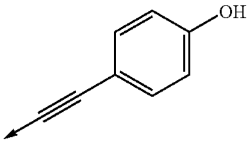 |
| 1556 | + | |
| 1557 | − | |
| 1558 | rac | 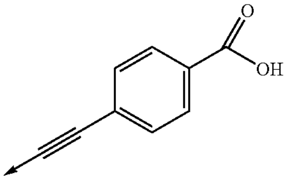 |
| 1559 | + | |
| 1560 | − | |
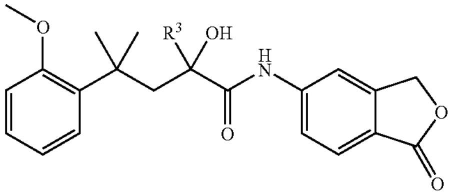
| No. | Racemic or Enantiomer | R3 |
|---|---|---|
| 1561 | rac | 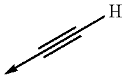 |
| 1562 | + | |
| 1563 | − | |
| 1564 | rac | 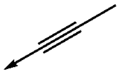 |
| 1565 | + | |
| 1566 | − | |
| 1567 | rac | 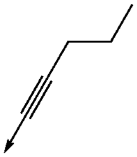 |
| 1568 | + | |
| 1569 | − | |
| 1570 | rac | 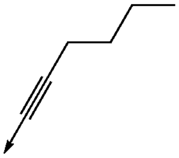 |
| 1571 | + | |
| 1572 | − | |
| 1573 | rac | 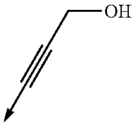 |
| 1574 | + | |
| 1575 | − | |
| 1576 | rac | 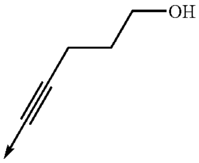 |
| 1577 | + | |
| 1578 | − | |
| 1579 | rac | 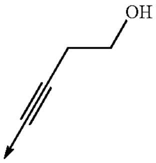 |
| 1580 | + | |
| 1581 | − | |
| 1582 | rac | 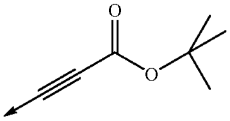 |
| 1583 | + | |
| 1584 | − | |
| 1585 | rac | 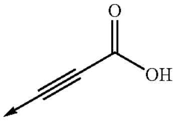 |
| 1586 | + | |
| 1587 | − | |

-continued

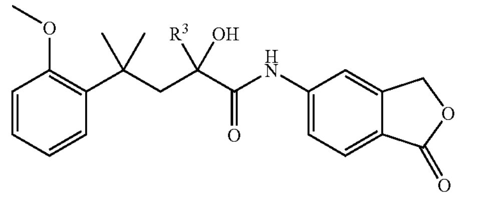

| No. | Racemic or Enantiomer | R3 |
|---|---|---|
| 1588<br>1589<br>1590 | rac<br>+<br>– | 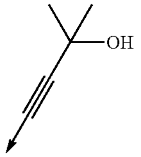 |
| 1591<br>1592<br>1593 | rac<br>+<br>– | 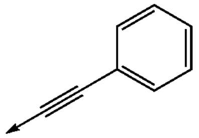 |
| 1594<br>1595<br>1596 | rac<br>+<br>– | 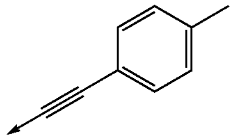 |
| 1597<br>1598<br>1599 | rac<br>+<br>– | 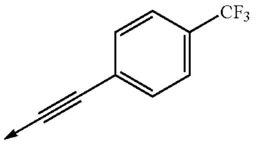 |
| 1600<br>1601<br>1602 | rac<br>+<br>– | 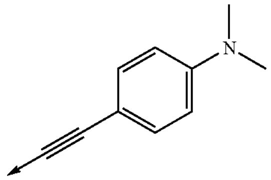 |
| 1603<br>1604<br>1605 | rac<br>+<br>– | 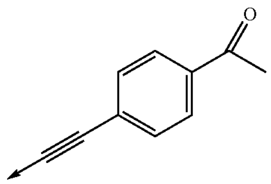 |
| 1606<br>1607<br>1608 | rac<br>+<br>– | 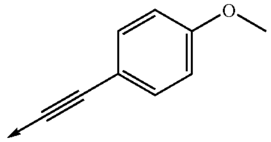 |
| 1609<br>1610<br>1611 | rac<br>+<br>– | 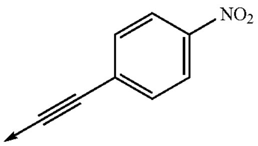 |

-continued

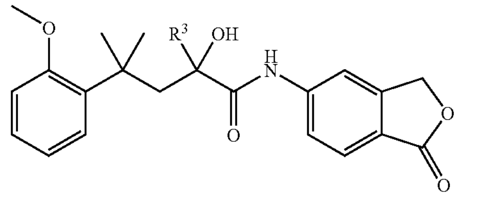

| No. | Racemic or Enantiomer | R3 |
|---|---|---|
| 1612<br>1613<br>1614 | rac<br>+<br>– | 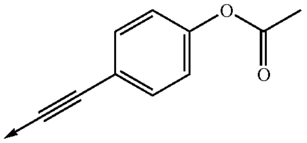 |
| 1615<br>1616<br>1617 | rac<br>+<br>– | 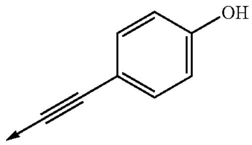 |
| 1618<br>1619<br>1620 | rac<br>+<br>– | 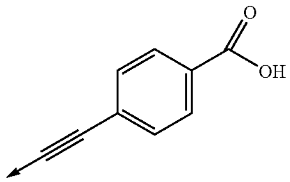 |

14. A compound according to claim 8, in which A is an unsubstituted phenyl radical.

15. A pharmaceutical composition comprising a compound according to claim 1 and one or more pharmaceutically acceptable carriers, adjuvants and/or vehicles.

16. A pharmaceutical composition comprising a compound according to claim 13 and one or more pharmaceutically acceptable carriers, adjuvants and/or vehicles.

17. A compound according to claim 13, which is one of the compounds from compounds numbers 1-120, 481-540, 961-1140, 1201-1260, 1321-1380, and 1561-1620.

18. A compound according to claim 13, which is one of the compounds from compounds numbers 121-480, 541-720, 781-960 and 1261-1320.

19. A compound according to claim 13, which is one of the compounds from compounds numbers 721-780.

20. A compound according to claim 13, which is one of the compounds from compounds numbers 1141-1200.

21. A compound according to claim 13, which is one of the compounds from compounds numbers 1381-1440.

22. A compound according to claim 13, which is one of the compounds from compounds numbers 1441-1500.

23. A compound according to claim 13, which is one of the compounds from compounds numbers 1501-1560.

24. A compound according to claim 13, which is one of the compounds from compounds numbers 1-60.

25. A compound according to claim 13, which is one of the compounds from compounds numbers 121-300.

26. A compound according to claim 13, which is one of the compounds from compounds numbers 1441-1500.

* * * * *

UNITED STATES PATENT AND TRADEMARK OFFICE

CERTIFICATE OF CORRECTION

PATENT NO. : 7,408,060 B2
APPLICATION NO. : 11/473336
DATED : August 5, 2008
INVENTOR(S) : Norbert Schmees It is certified that error appears in the above-identified patent and that said Letters Patent is hereby corrected as shown below:

Column 94, line 6 Claim 1 reads “salts” should read --salt--

Signed and Sealed this

Fourth Day of November, 2008

JON W. DUDAS
*Director of the United States Patent and Trademark Office*